(12) United States Patent
Cohen et al.

(10) Patent No.: US 7,642,240 B2
(45) Date of Patent: Jan. 5, 2010

(54) BIOCONJUGATES COMPRISING SULFATED POLYSACCHARIDES AND THEIR USES

(75) Inventors: Smader Cohen, Beer Sheva (IL); Inbar Freeman, Doar Na Ha'negev (IL)

(73) Assignee: Ben-Gurion University of the Negev Research and Development Authority, Beer Sheva (IL)

( * ) Notice: Subject to any disclaimer, the term of this patent is extended or adjusted under 35 U.S.C. 154(b) by 113 days.

(21) Appl. No.: 11/649,844

(22) Filed: Jan. 5, 2007

(65) Prior Publication Data

US 2007/0110814 A1 May 17, 2007

Related U.S. Application Data

(63) Continuation-in-part of application No. 11/374,279, filed on Oct. 11, 2005.

(51) Int. Cl.
*A61K 38/00* (2006.01)
*C07K 14/00* (2006.01)
(52) U.S. Cl. .................. 514/12; 530/350; 977/773
(58) Field of Classification Search ............ None
See application file for complete search history.

(56) References Cited

U.S. PATENT DOCUMENTS 4,178,361 A * 12/1979 Cohen et al. ............ 424/487

2007/0081976 A1 * 4/2007 Cohen et al. ............ 424/85.6

FOREIGN PATENT DOCUMENTS

| EP | 1886696 A1 | 2/2008 |
| WO | 8912464 A1 | 12/1989 |
| WO | 9921588 A1 | 5/1999 |
| WO | 0064481 A1 | 11/2000 |
| WO | 0166164 A1 | 9/2001 |

OTHER PUBLICATIONS

Paredes et al., "Mechanisms responsible for catalysis of the inhbition of Factor Xa or Thrombin by Antithrombin using a covalent Antithrombin-Heparin complex", The Journal of Biological Chemistry 278: 23398-23409 (2003).*
Web link to Wikipedia: en.wikipedia.org/wiki/iduronic_acid downloaded Sep. 4, 2007.*
Schroeder-Tefft et al., Collagen and heparin matrices for growth factor delivery, Journal of Controlled Release, 48:29-31 (1997).

* cited by examiner

*Primary Examiner*—Anand U Desai
(74) *Attorney, Agent, or Firm*—Browdy and Neimark, PLLC

(57) ABSTRACT

The present invention provides bioconjugates comprising a sulfated polysaccharide such as alginate sulfate and hyaluronan sulfate and at least one bioactive polypeptide capable of binding a sulfate group of said sulfated polysaccharide. The bioactive polypeptide can be a heparin-binding polypeptide and/or a positively-charged polypeptide. Also, provided are delivery systems and methods for sustained release of said bioactive polypeptide(s) using said bioconjugates.

21 Claims, 33 Drawing Sheets

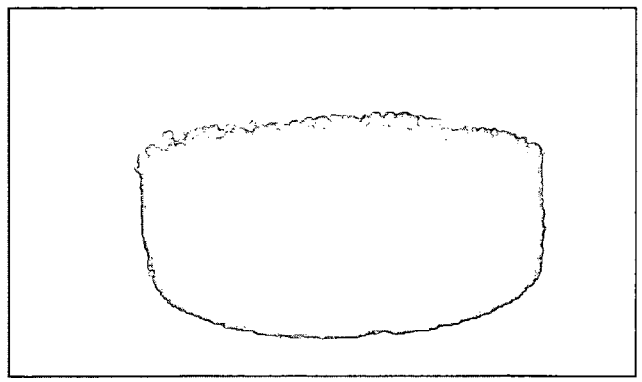
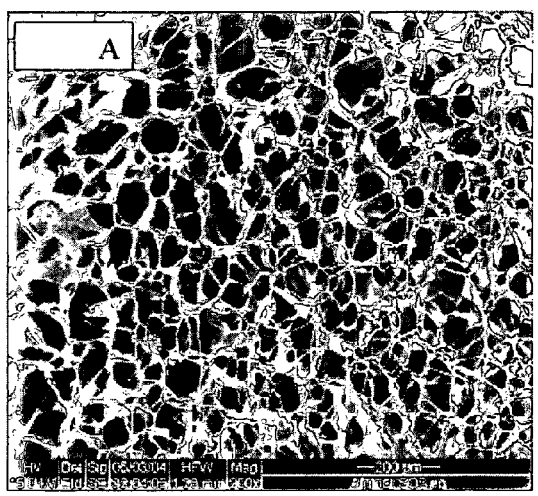 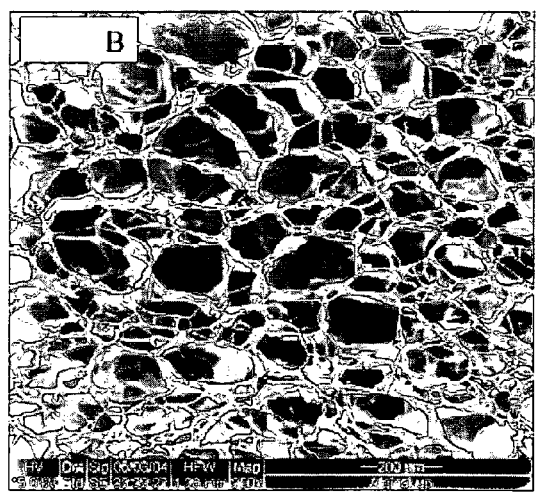
Fig. 18A						Fig. 18B

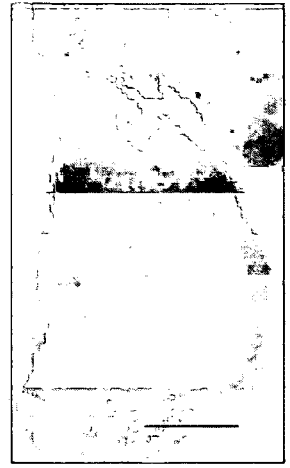
Fig. 19A
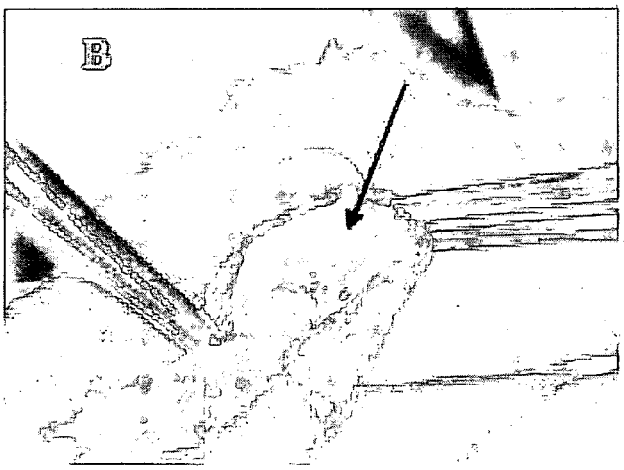
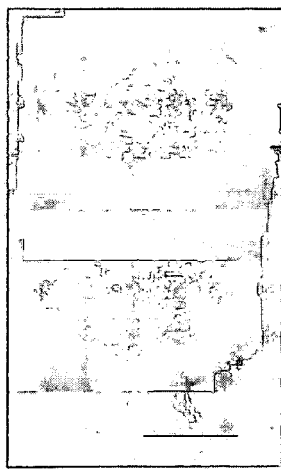
Fig. 19B
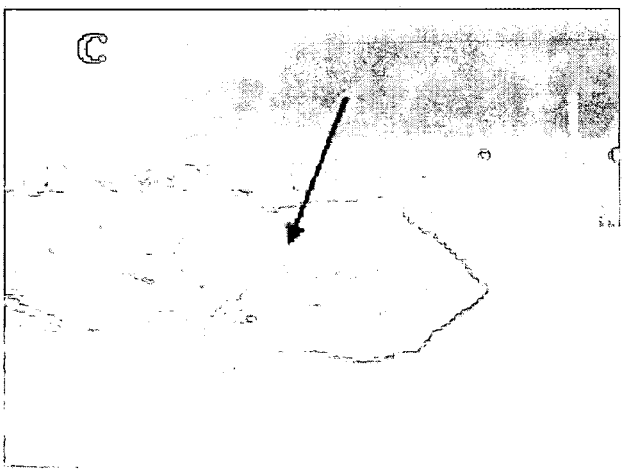
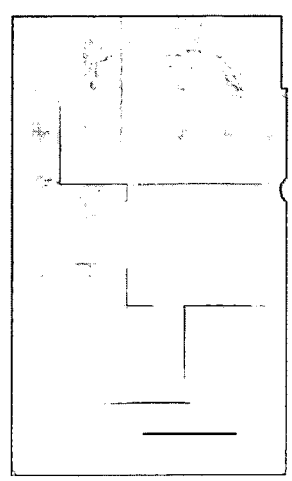
Fig. 19C

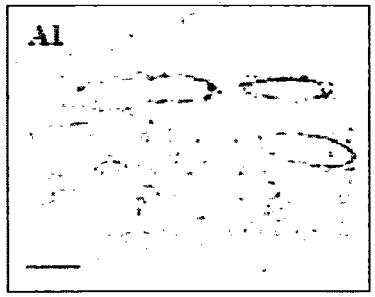 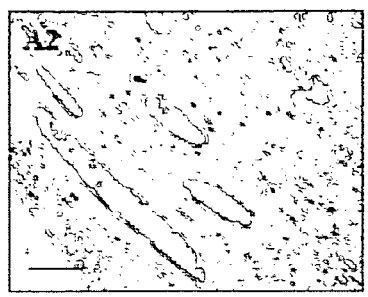 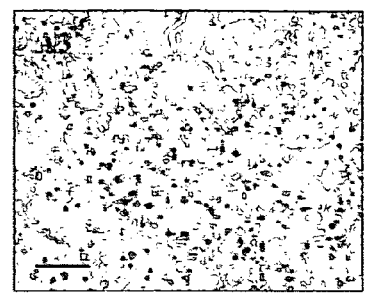
Fig. 25 A1　　　　Fig. 25 A2　　　　Fig. 25 A3
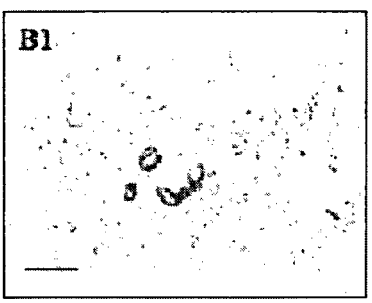 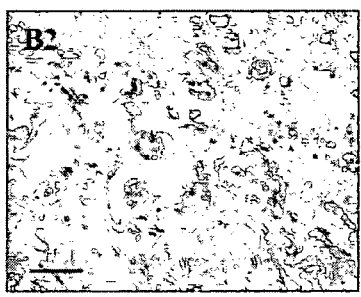 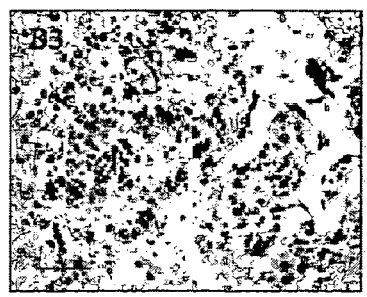
Fig. 25 B1　　　　Fig. 25 B2　　　　Fig. 25 B3
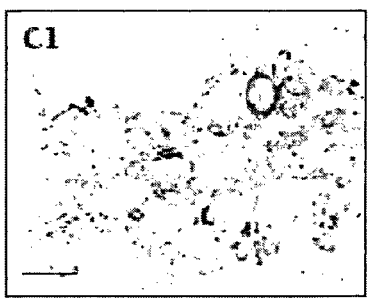 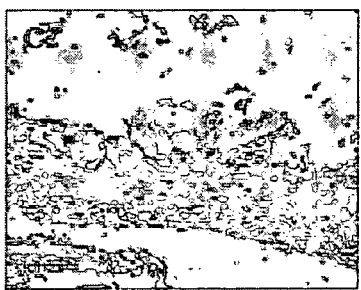 
Fig. 25 C1　　　　Fig. 25 C2　　　　Fig. 25 C3

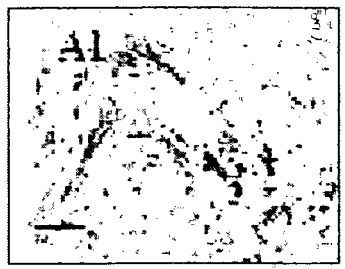
Fig. 29 A1
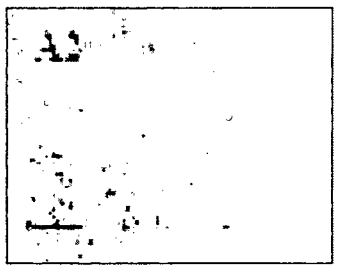
Fig. 29 A2
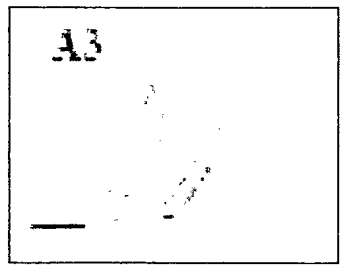
Fig. 29 A3
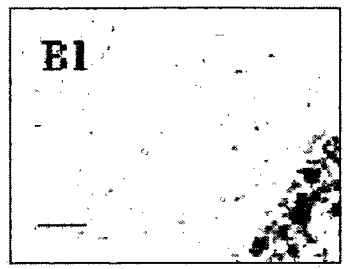
Fig. 29 B1
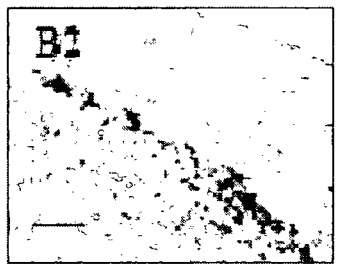
Fig. 29 B2
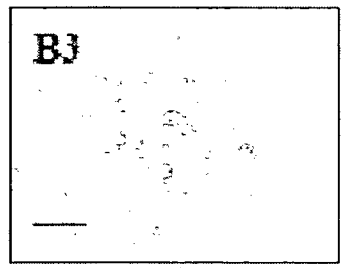
Fig. 29 B3
Fig. 29 C1
Fig. 29 C2
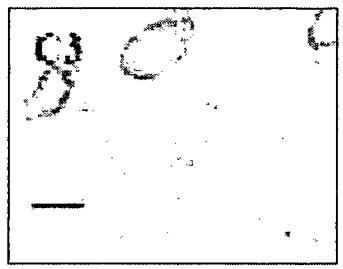
Fig. 29 C3
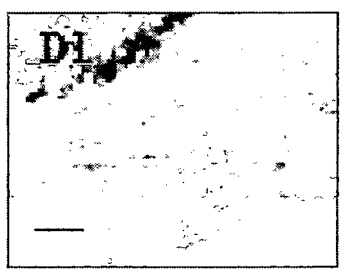
Fig. 29 D1
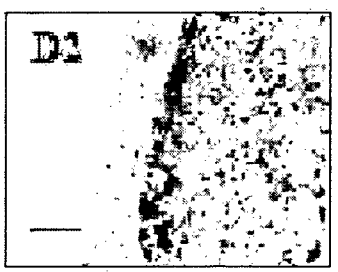
Fig. 29 D2
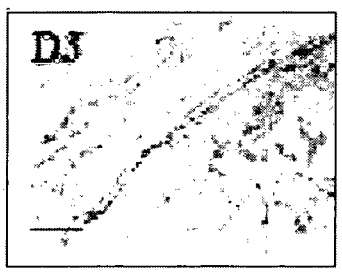
Fig. 29 D3
Fig. 29 E1
Fig. 29 E2
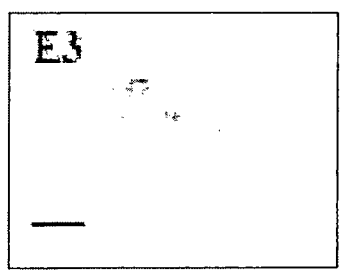
Fig. 29 E3

  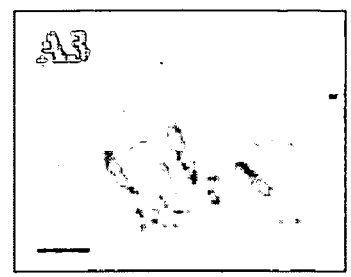
Fig. 30 A1    Fig. 30 A2    Fig. 30 A3
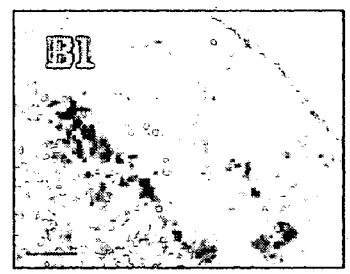 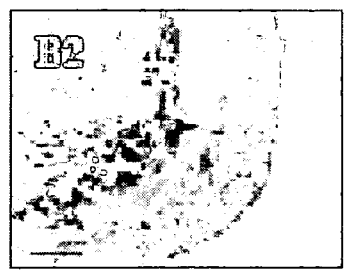 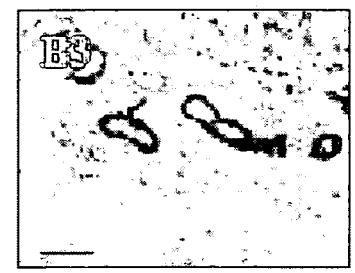
Fig. 30 B1    Fig. 30 B2    Fig. 30 B3
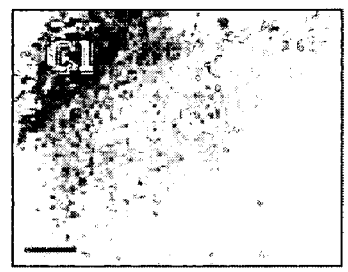  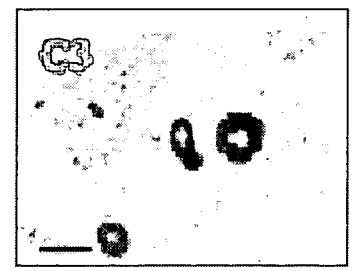
Fig. 30 C1    Fig. 30 C2    Fig. 30 C3
  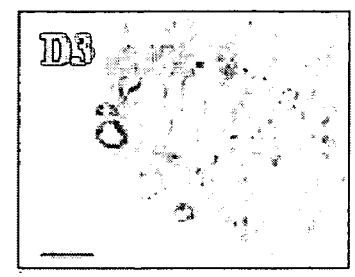
Fig. 30 D1    Fig. 30 D2    Fig. 30D3
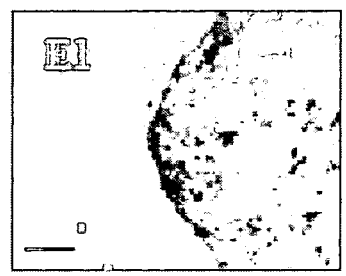  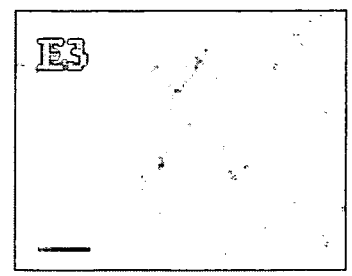
Fig. 30 E1    Fig. 30 E2    Fig. 30 E3

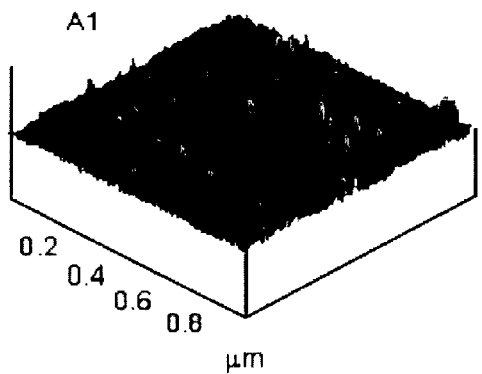
Fig. 35A1
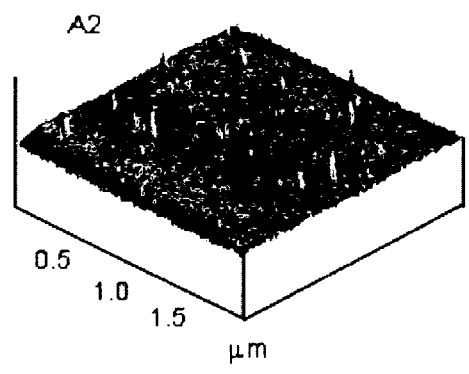
Fig. 35A2
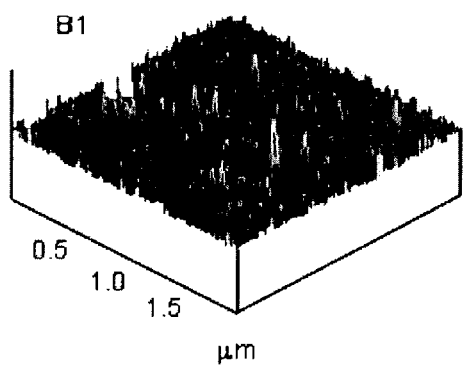
Fig. 35B1
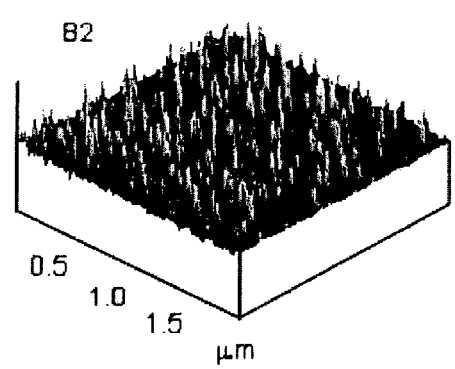
Fig. 35B2
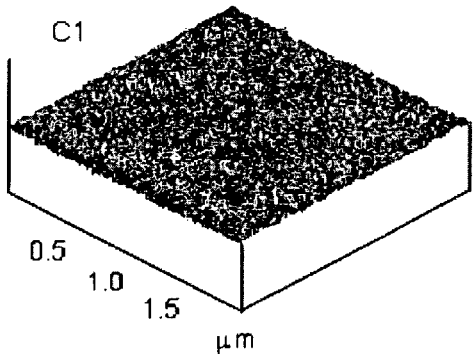
Fig. 35C1
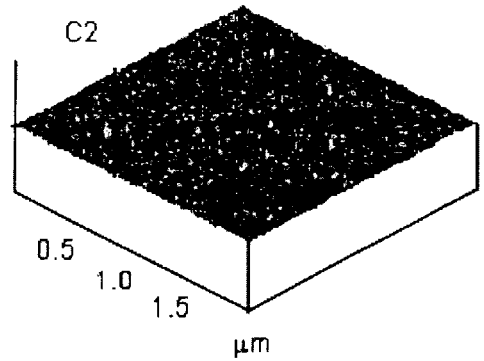
Fig. 35C2

BIOCONJUGATES COMPRISING SULFATED POLYSACCHARIDES AND THEIR USES

This application is a Continuation-in-Part of U.S. application Ser. No. 11/374,279, filed Oct. 11, 2005, the contents of which are hereby incorporated by reference.

FIELD OF THE INVENTION

The present invention relates to sulfated polysaccharides, particularly to polysaccharides containing uronic acid residues, more particularly to alginate sulfate and hyaluronan sulfate, to bioconjugates comprising them as delivery systems for sustained release of bioactive polypeptides and to pharmaceutical compositions comprising said sulfated polysaccharides or said bioconjugates comprising them and bioactive polypeptides.

Abbreviations: AP: amyloid P; ApoE: apolipoprotein E; AT III: antithrombin III; C1 INH: C1 esterase inhibitor; CS: circumsporozoite; CXCL4: CXC chemokine ligand 4; CypA: cyclophilin A; EGF: epidermal growth factor; FGF: fibroblast growth factors; FTIR: Fourier-transformed infrared spectroscopy; HA: hyaluronan, hyaluronic acid; HB-GAM: heparin-binding growth-associated molecule; HGF: hepatocyte growth factor; HIV-1: immunodeficiency virus type-1; HSV: herpes simplex virus; IGF: insulin-like growth factor; IL-6: interleukin-6; IL-8: interleukin-8; MCP-1: monocyte chemoattractant protein-1; MIP-1: macrophage inflammatory peptide-1; RANTES: regulated on activation, normal T expressed and secreted; SDF-1: stromal cell-derived factor-1; SLP1: serine protease inhibitor; SPR: surface plasmon resonance; TPO: thrombopoietin; TSR: thrombospondin type I repeat; VCP: Vaccinia virus complement control protein; VEGF: vascular endothelial growth factor.

BACKGROUND OF THE INVENTION

Controlled-release dosage forms are designed to reduce drug-dosing frequency and to reduce fluctuation in plasma drug concentration, providing a more uniform therapeutic effect. Less frequent dosing is more convenient and may improve patient compliance. These dosage forms are suitable for drugs that otherwise require frequent dosing because elimination half-life and duration of effect are short.

Man-made controlled release dosage forms, such as hydrogels and solid polymeric microspheres, usually rely on drug release mechanisms that are based on passive diffusion, polymer degradation or passive diffusion coupled with polymer degradation. Examples of these systems include polyester microspheres or alginate hydrogels.

On the other hand, nature's way of devising controlled release dosage forms is based on principles of biological specificity. A known example to this is the biomolecular interactions between heparin/heparan sulfate and heparin-binding peptides, e.g. growth factors. These interactions form a depot for growth factor storage in the tissues. Upon tissue injury, the growth factors are released and induce processes associated with wound healing.

For years, we and others have been investigating the use of alginate hydrogels for the controlled delivery of drugs and as scaffolds for tissue engineering.

Alginate is a polysaccharide derived from brown seaweed. It is an anionic polysaccharide composed of uronic acids (guluronic (G) and mannuronic (M) acids) that undergoes gelation in the presence of bivalent cations, such as $Ca^{2+}$ and $Ba^{2+}$. In the pharmaceutical/medicinal fields, it is used successfully as encapsulation material, mostly for cells (bacterial, plant and mammalian cells). For molecules, it is much less effective, and even macromolecules in size of 250 kDa are rapidly released from alginate hydrogel systems. In particular, biological molecules of interest such as cytokines, growth factors, with sizes ranging between 5 to 100 kDa, are rapidly released.

Thus, there is a need for modification/s in polysaccharides such as alginate for their use in the controlled delivery of drugs. Recently, the inventors disclosed in an abstract that alginate sulfate interacts with basic fibroblast growth factor (bFGF) and delivers bFGF in a controlled manner (Freeman et al., 2004).

SUMMARY OF THE INVENTION

It has now been found according to the present invention that a bioconjugate comprising a sulfated polysaccharide, such as alginate sulfate and hyaluronan sulfate, and at least one bioactive peptide capable of binding a sulfate group of said sulfated polysaccharide, can direct the sustained release of said at least one bioactive peptide from said bioconjugate.

Thus, the present invention relates, in one aspect, to a bioconjugate comprising a sulfated polysaccharide and at least one bioactive polypeptide capable of binding a sulfate group of said sulfated polysaccharide.

The present invention further relates to a pharmaceutical composition comprising a bioconjugate of the invention and a pharmaceutically acceptable carrier, suitable as a delivery system for sustained release of the at least one bioactive polypeptide and for treatment of diseases or disorders that can be treated with said at least one bioactive polypeptide.

In another aspect, the present invention relates to pharmaceutical compositions comprising sulfated polysaccharides and a pharmaceutically acceptable carrier, for treatment or inhibition of a disease or disorder caused by, or associated with, the activity of at least one bioactive polypeptide capable of binding a sulfate group of said sulfated polysaccharide.

Also provided is a method for treatment of a disease or disorder caused by, or associated with, the activity of at least one bioactive polypeptide capable of binding a sulfate group of a sulfated polysaccharide, which comprises administering to said patient an effective amount of sulfated alginate, sulfated hyaluronan, or both.

The SPR sensorgram presents the affinity profile as a function of bFGF concentrations (Table 2).

Figure 4A:
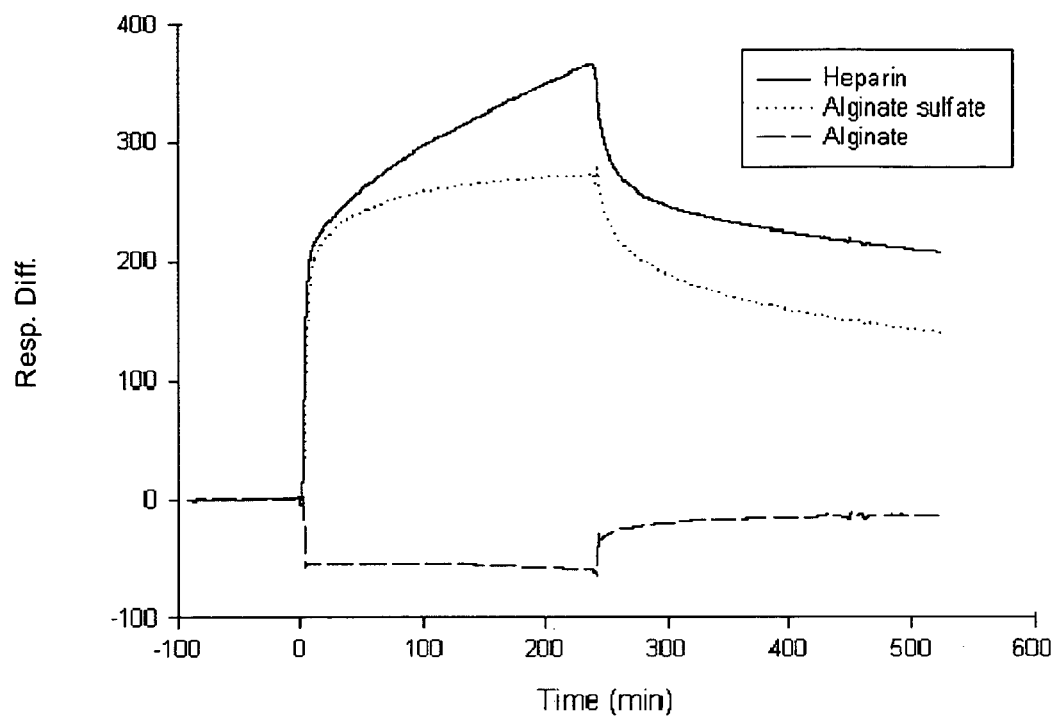
Figure 4B:
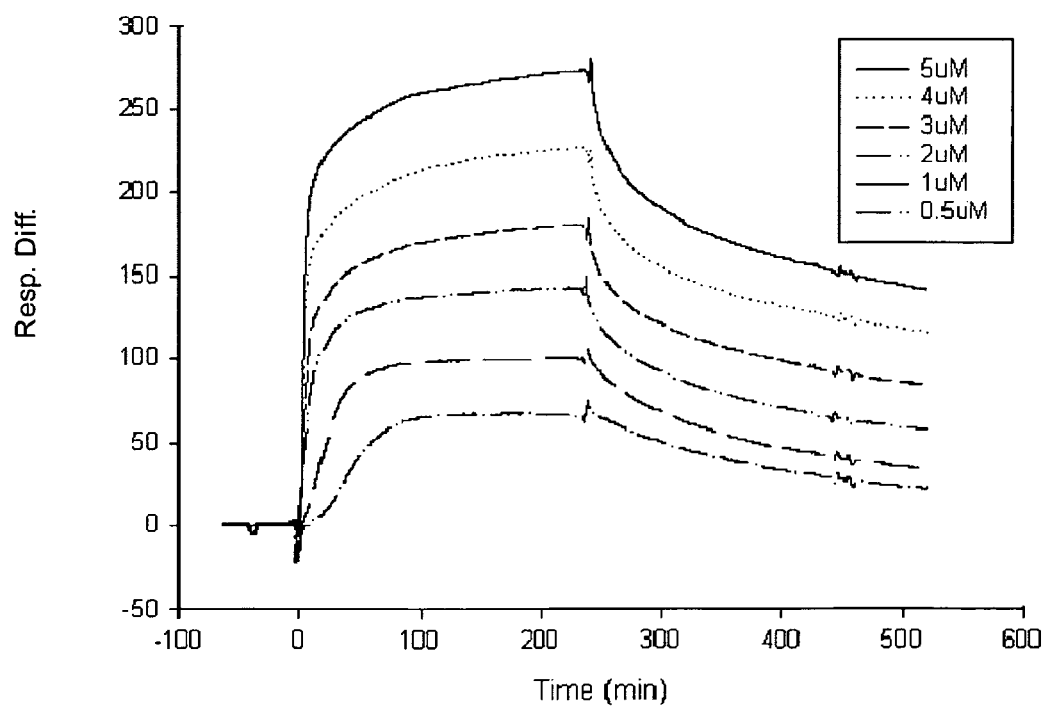
Figure 5A:
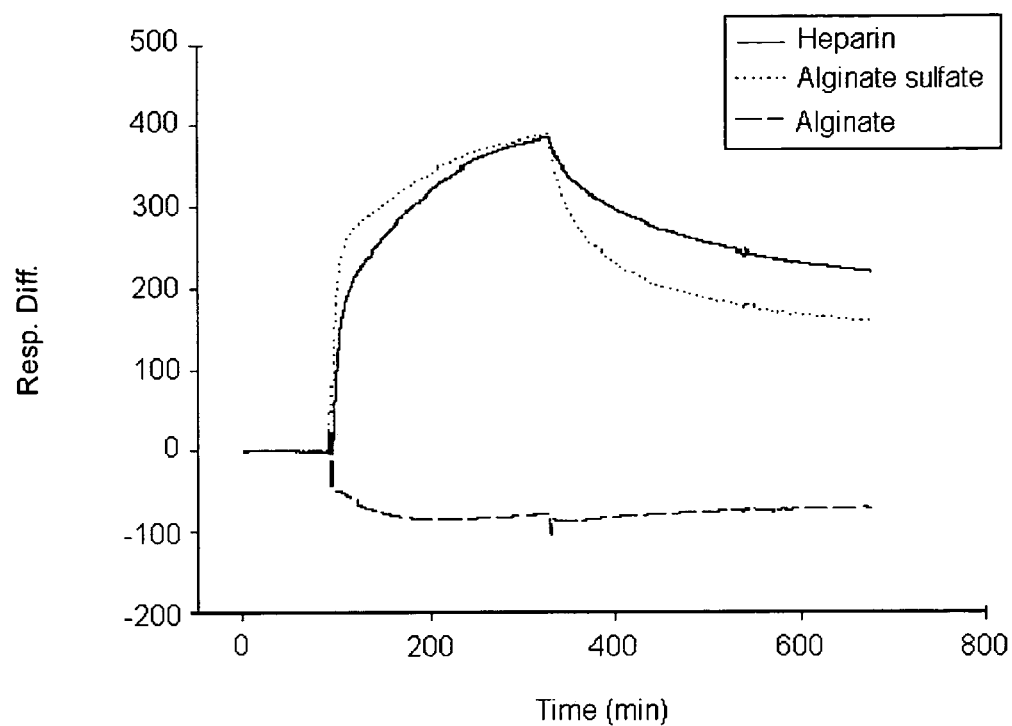
Figure 5B:
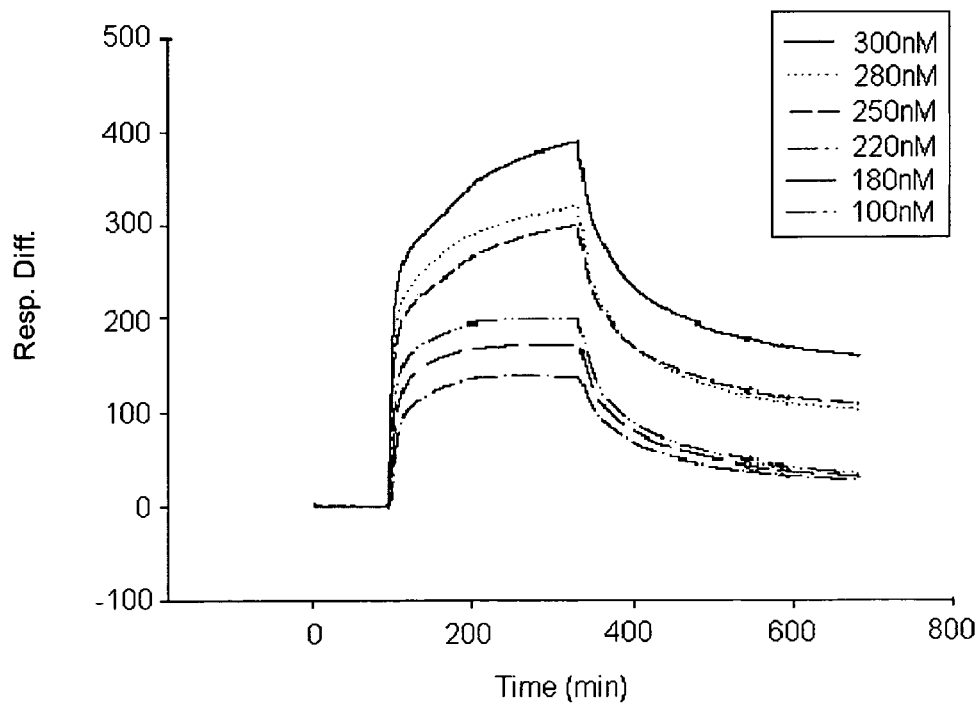

FIGS. 4A-4B show SPR sensorgrams of VEGF binding to alginate sulfate, over a range of peptide concentrations. (4A) VEGF (5 µM) binding to heparin, alginate sulfate and alginate immobilized on sensor chip SA. Binding was specific for heparin and alginate sulfate while no interactions with immobilized biotinylated alginate were seen. (4B) VEGF was injected over immobilized alginate sulfate on sensor chip SA. The SPR sensorgram presents the affinity profile as a function of VEGF concentrations FIGS. 5A-5B show SPR sensorgrams of TGFβ1 binding to alginate sulfate, over a range of peptide concentrations. (5A) TGFβ1 (300 nM) binding to heparin, alginate sulfate and alginate immobilized on sensor chip SA. Binding was specific for heparin and alginate sulfate while no interactions with immobilized biotinylated alginate were seen. (5B) TGFβ1 was injected over immobilized alginate sulfate on sensor chip SA. The SPR sensorgram presents the affinity profile as a function of TGFβ1 concentrations.

Figure 6A:
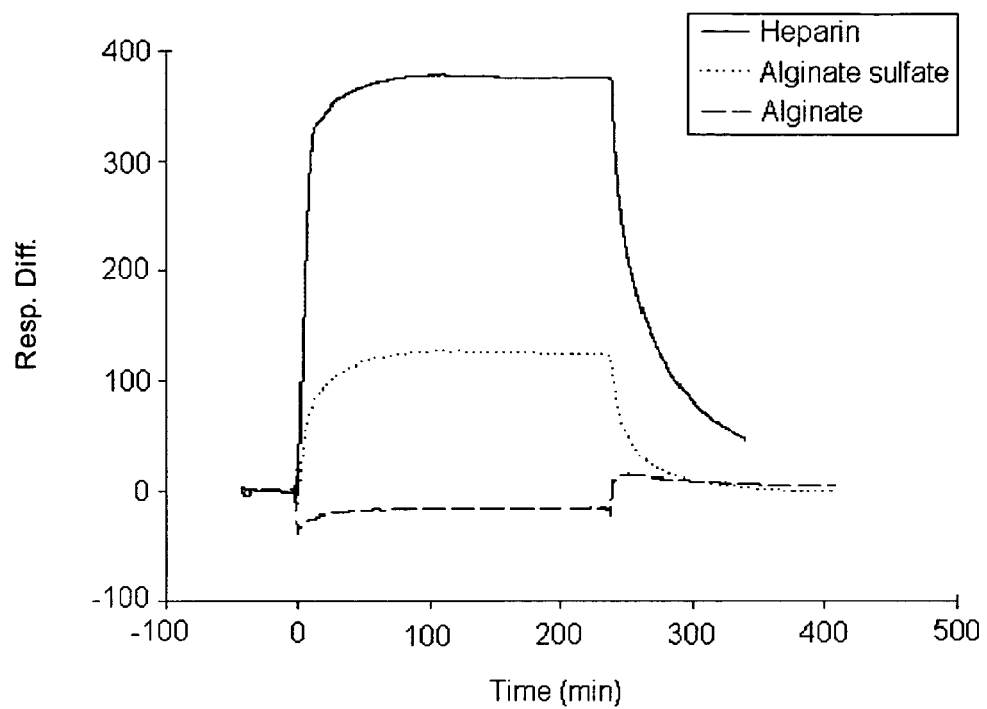
Figure 6B:
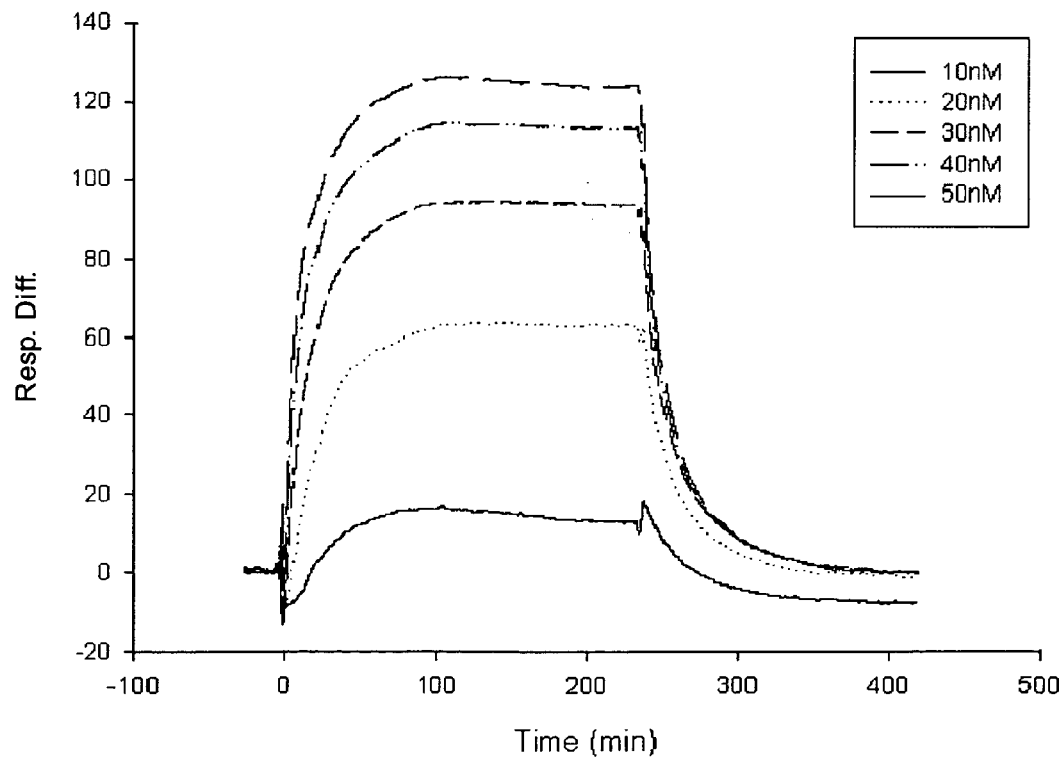
Figure 7A:
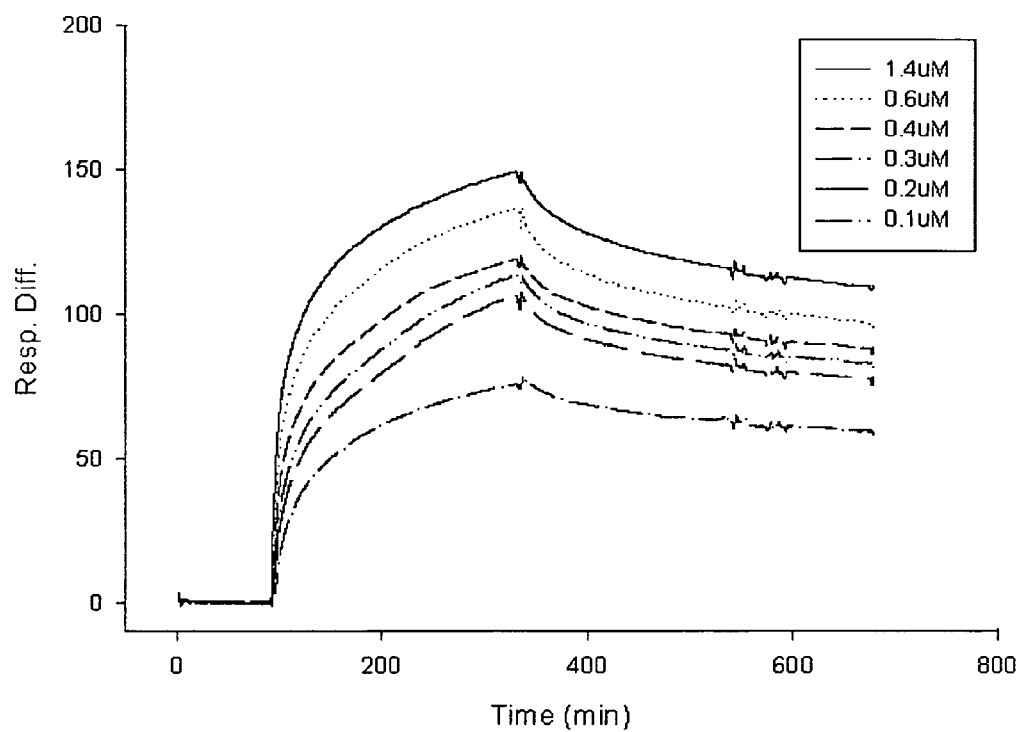
Figure 7B:
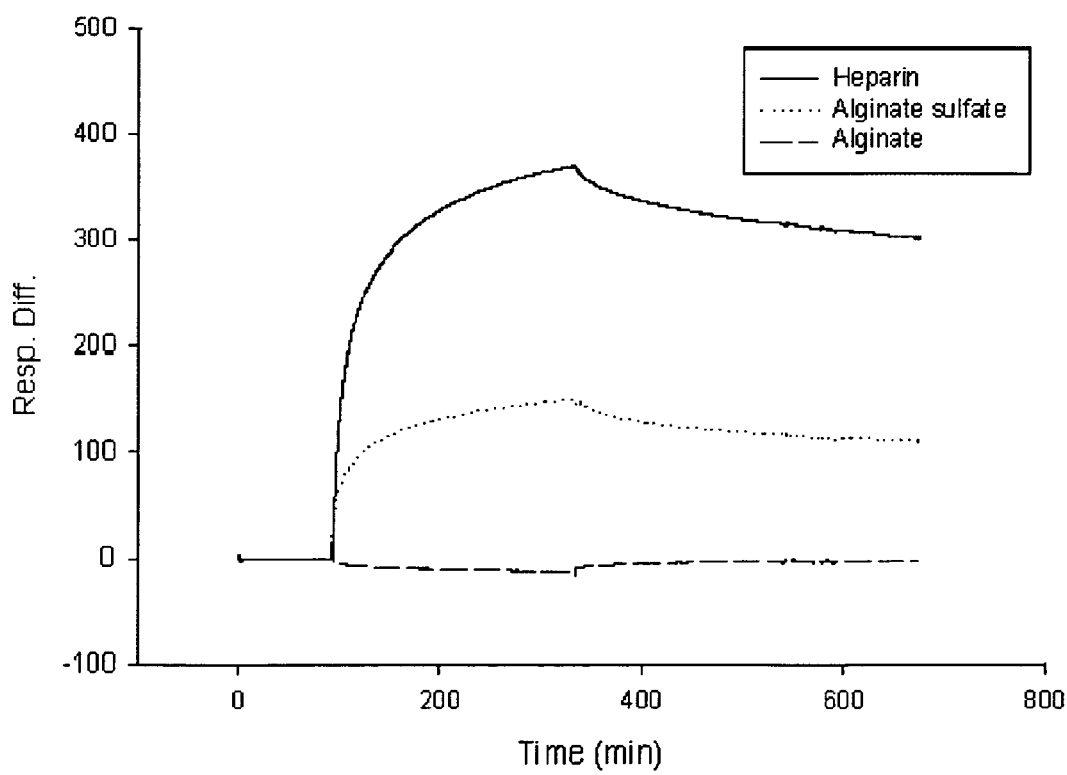

FIGS. 6A-6B show SPR sensorgrams of aFGF binding to alginate sulfate, over a range of peptide concentrations. (6A) aFGF (200 nM) binding to heparin, alginate sulfate and alginate immobilized on sensor chip SA. Binding was specific for heparin and alginate sulfate while no interactions with immobilized biotinylated alginate were seen. (6B) aFGF was injected over immobilized alginate sulfate on sensor chip SA. The SPR sensorgram presents the affinity profile as a function of aFGF concentrations FIGS. 7A-7B show SPR sensorgrams of IL-6 binding to alginate sulfate, over a range of peptide concentrations. (7A) IL-6 (1.4 µM) binding to heparin, alginate sulfate and alginate immobilized on sensor chip SA. Binding was specific for heparin and alginate sulfate while no interactions with immobilized biotinylated alginate were seen. (7B) IL-6 was injected over immobilized alginate sulfate on sensor chip SA. The SPR sensorgram presents the affinity profile as a function of IL-6 concentrations.

Figure 8A:
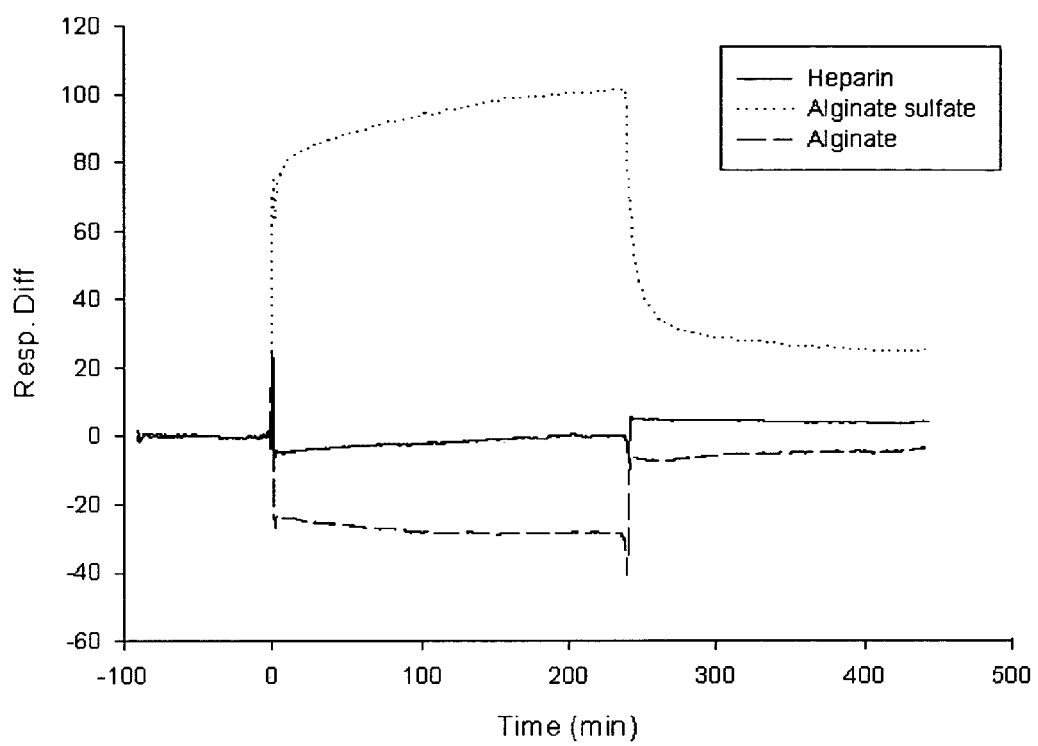
Figure 8B:
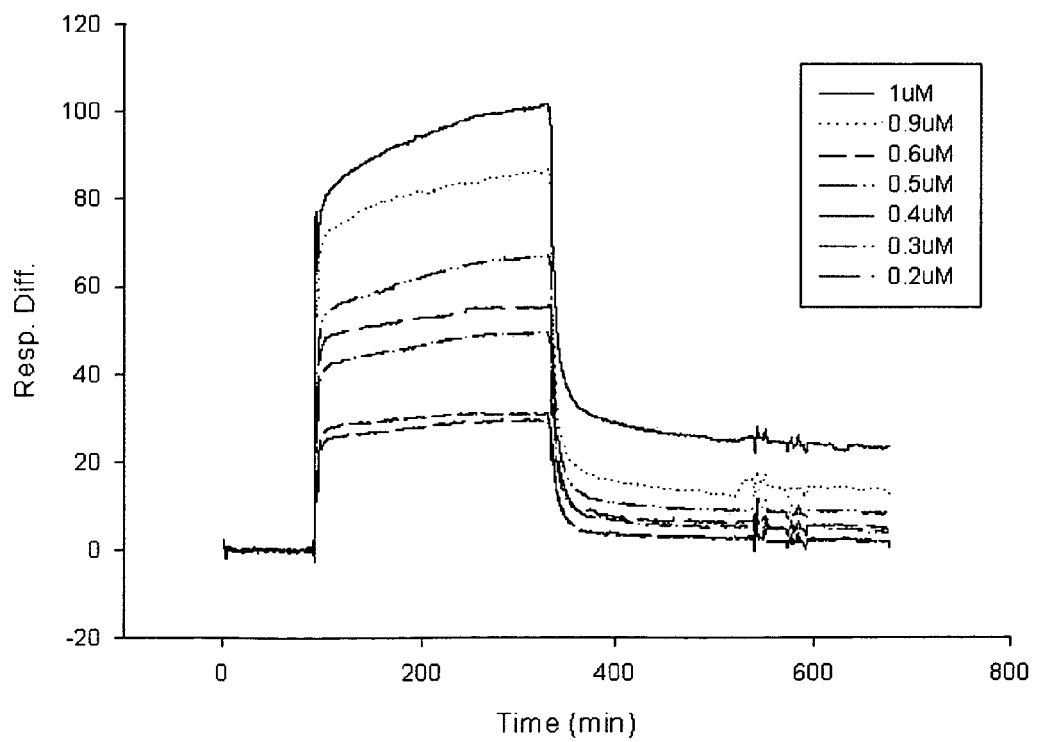

FIGS. 8A-8B show SPR sensorgrams of TPO binding to alginate sulfate, over a range of peptide concentrations. (8A) TPO (1.0 µM) binding to heparin, alginate sulfate and alginate immobilized on sensor chip SA. Binding was specific for heparin and alginate sulfate while no interactions with immobilized biotinylated alginate were seen. (8B)TPO was injected over immobilized alginate sulfate on sensor chip SA. The SPR sensorgram presents the affinity profile as a function of TPO concentrations.

Figure 9A:
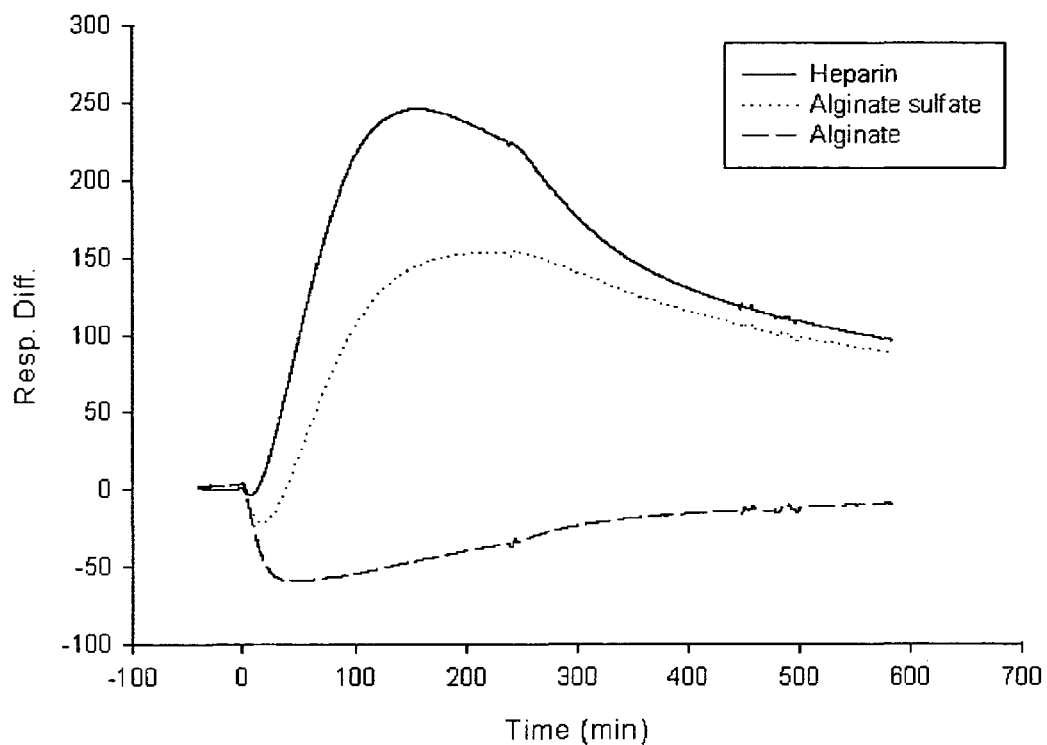
Figure 9B:
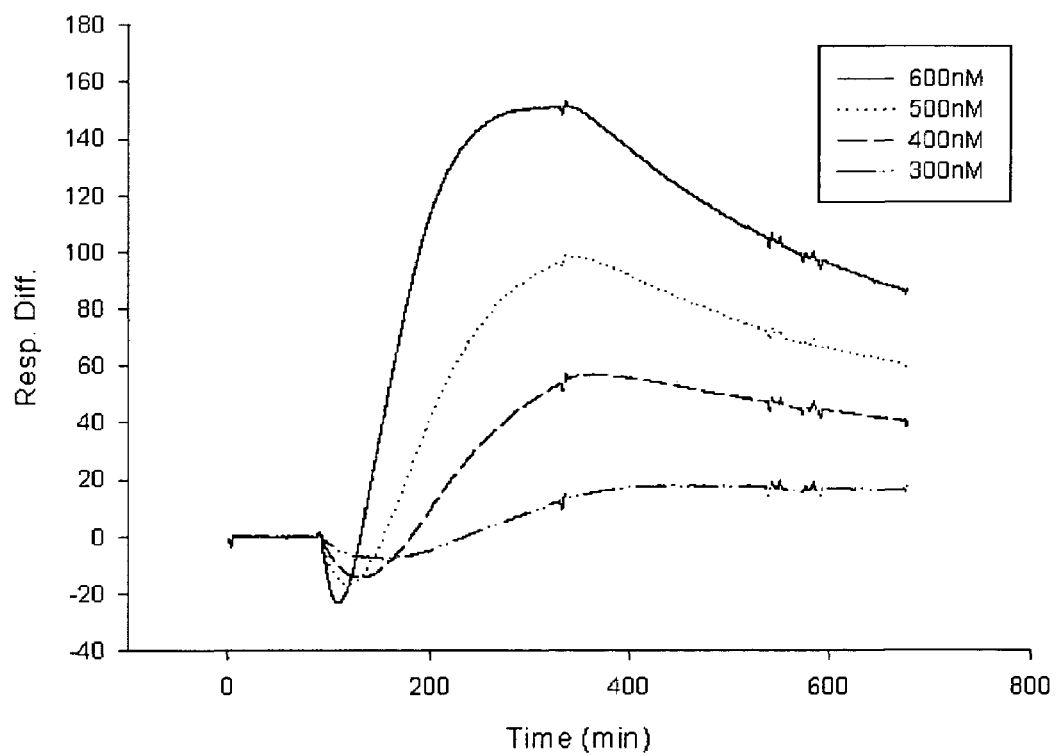

FIGS. 9A-9B show SPR sensorgrams of SDF-1 binding to alginate sulfate, over a range of peptide concentrations. (9A) SDF-1 (600 nM) binding to heparin, alginate sulfate and alginate immobilized on sensor chip SA. Binding was specific for heparin and alginate sulfate while no interactions with immobilized biotinylated alginate were seen. (9B) SDF-1 was injected over immobilized alginate sulfate on sensor chip SA. The SPR sensorgram presents the affinity profile as a function of SDF-1 concentrations.

Figure 10A:
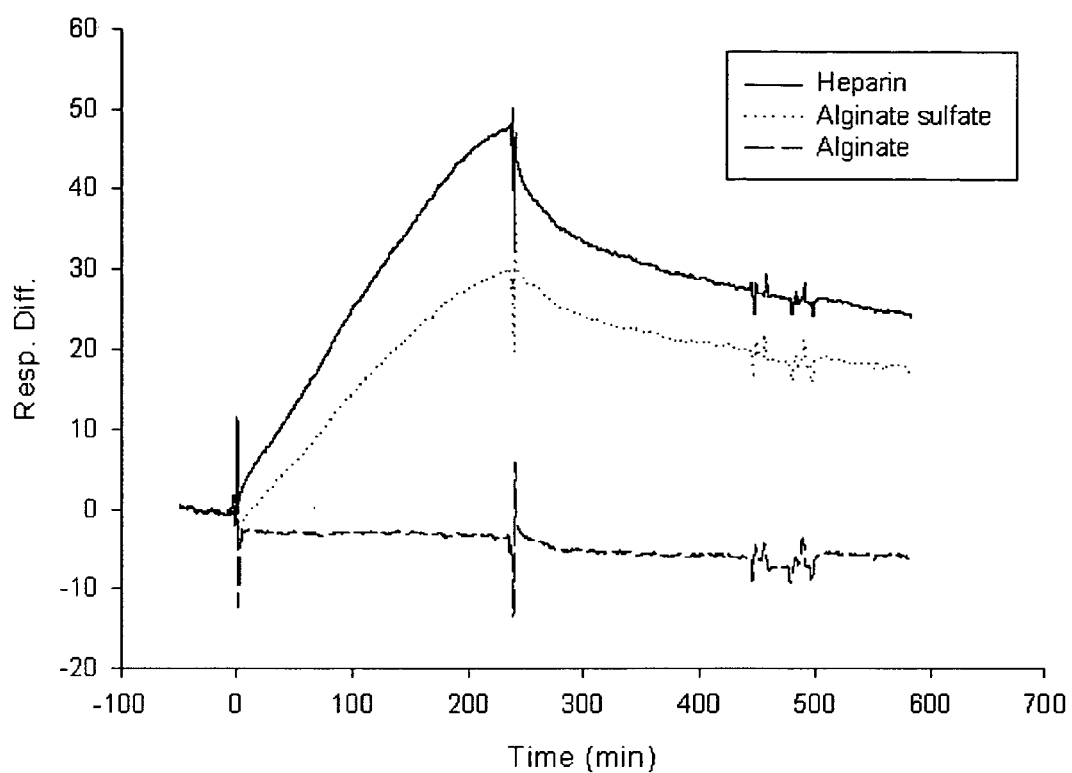
Figure 10B:
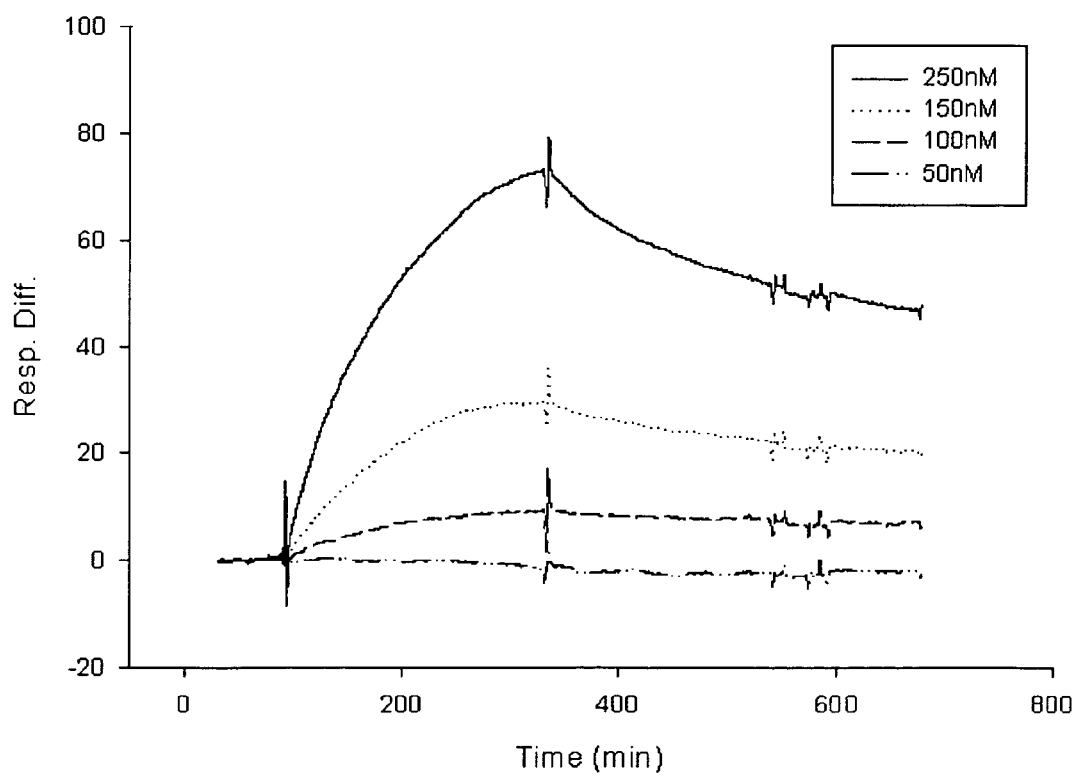

FIGS. 10A-10B show SPR sensorgrams of HGF binding to alginate sulfate, over a range of peptide concentrations. (10A) HGF (250 nM) binding to heparin, alginate sulfate and alginate immobilized on sensor chip SA. Binding was specific for heparin and alginate sulfate while no interactions with immobilized biotinylated alginate were seen. (10B) HGF was injected over immobilized alginate sulfate on sensor chip SA. The SPR sensorgram presents the affinity profile as a function of HGF concentrations.

Figure 11A:
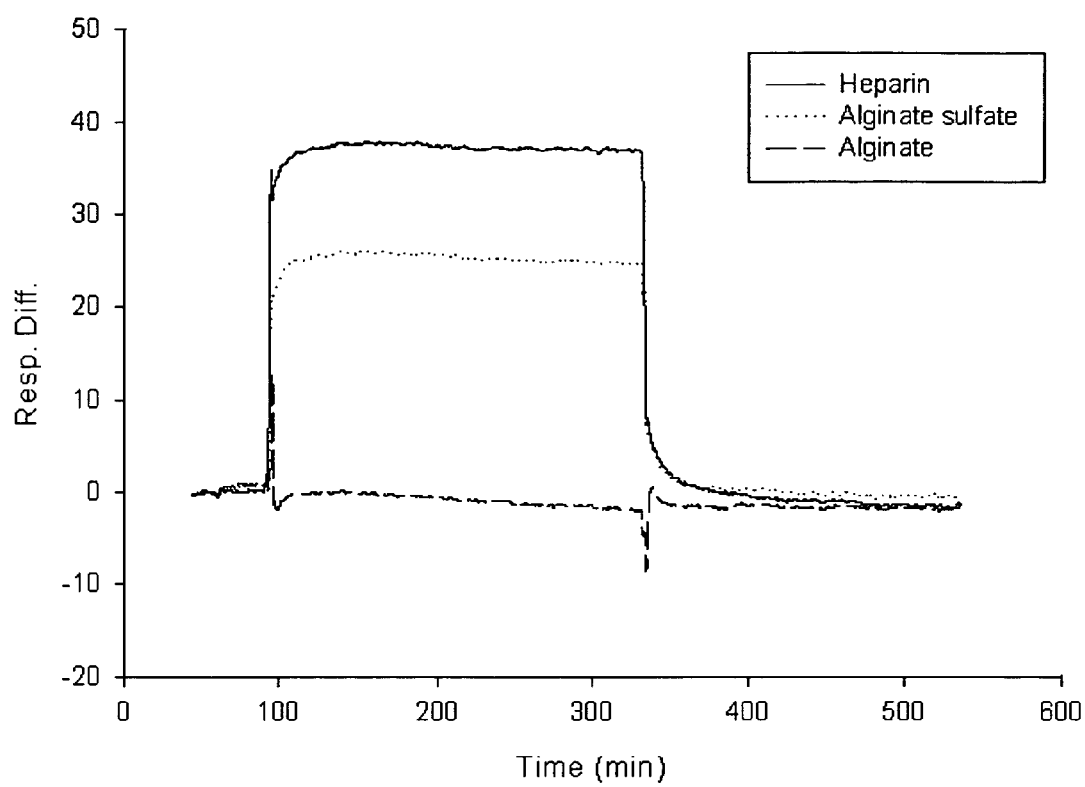
Figure 11B:
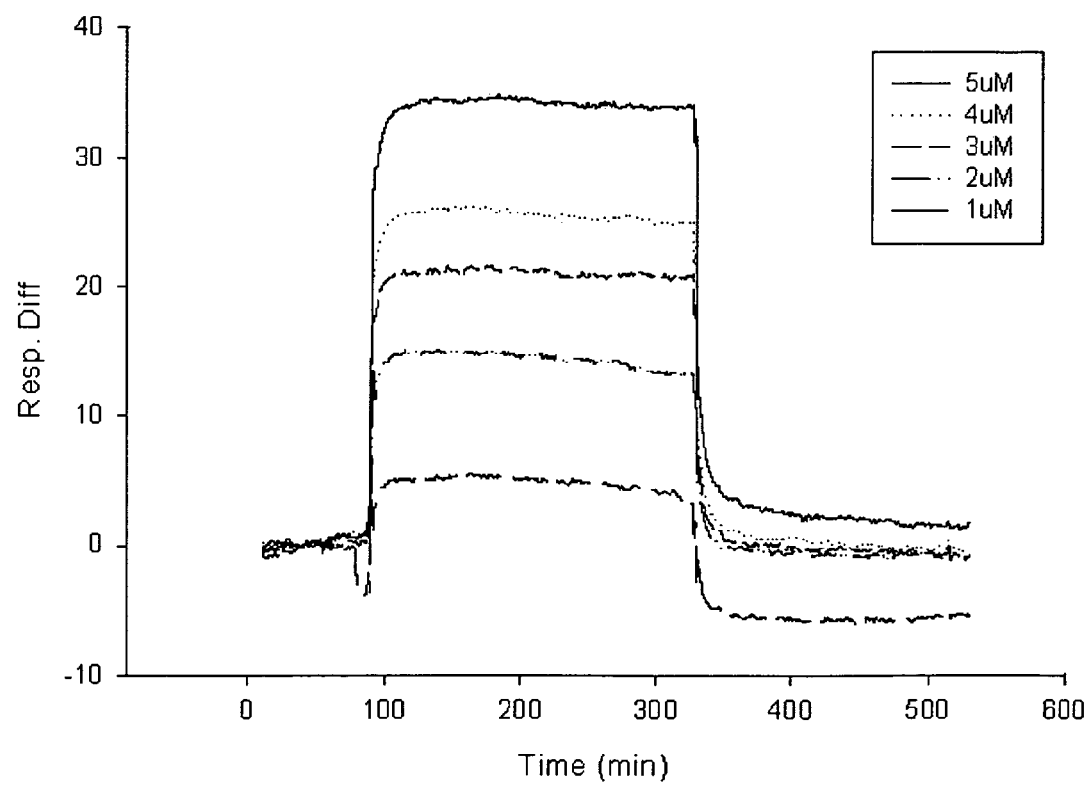

FIGS. 11A-11B show SPR sensorgrams of EGF binding to alginate sulfate, over a range of peptide concentrations. (11A) EGF (5 µM) binding to heparin, alginate sulfate and alginate immobilized on sensor chip SA. Binding was specific for heparin and alginate sulfate while no interactions with immobilized biotinylated alginate were seen. (11B) EGF was injected over immobilized alginate sulfate on sensor chip SA. The SPR sensorgram presents the affinity profile as a function of EGF concentrations.

Figure 12A:
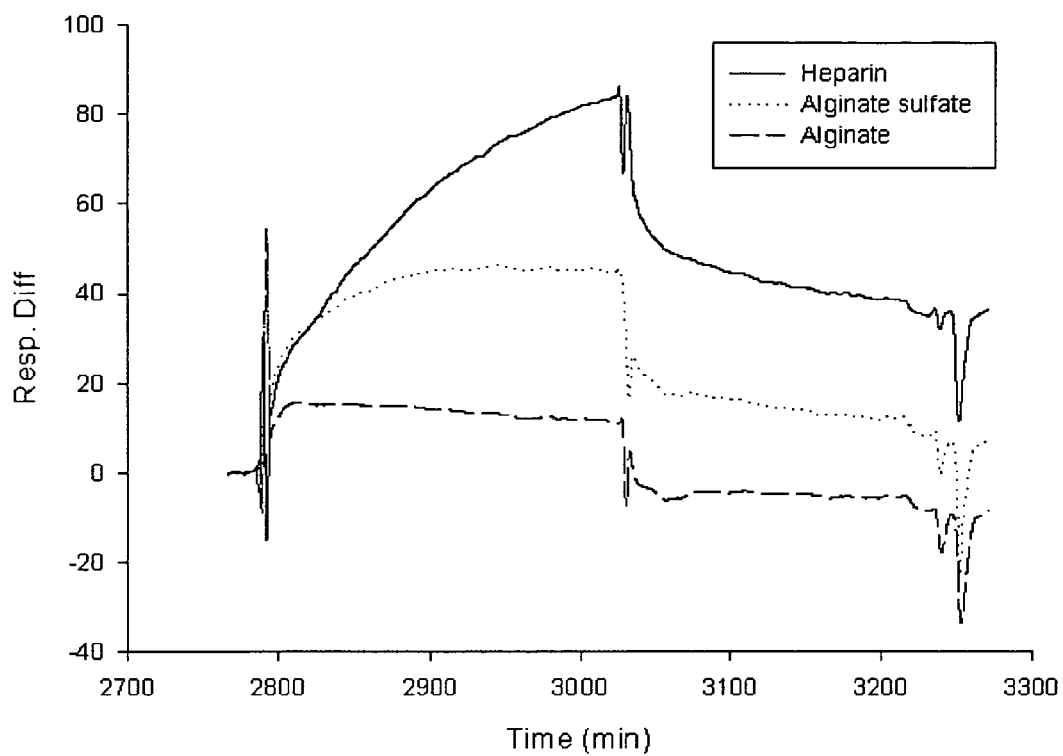
Figure 12B:
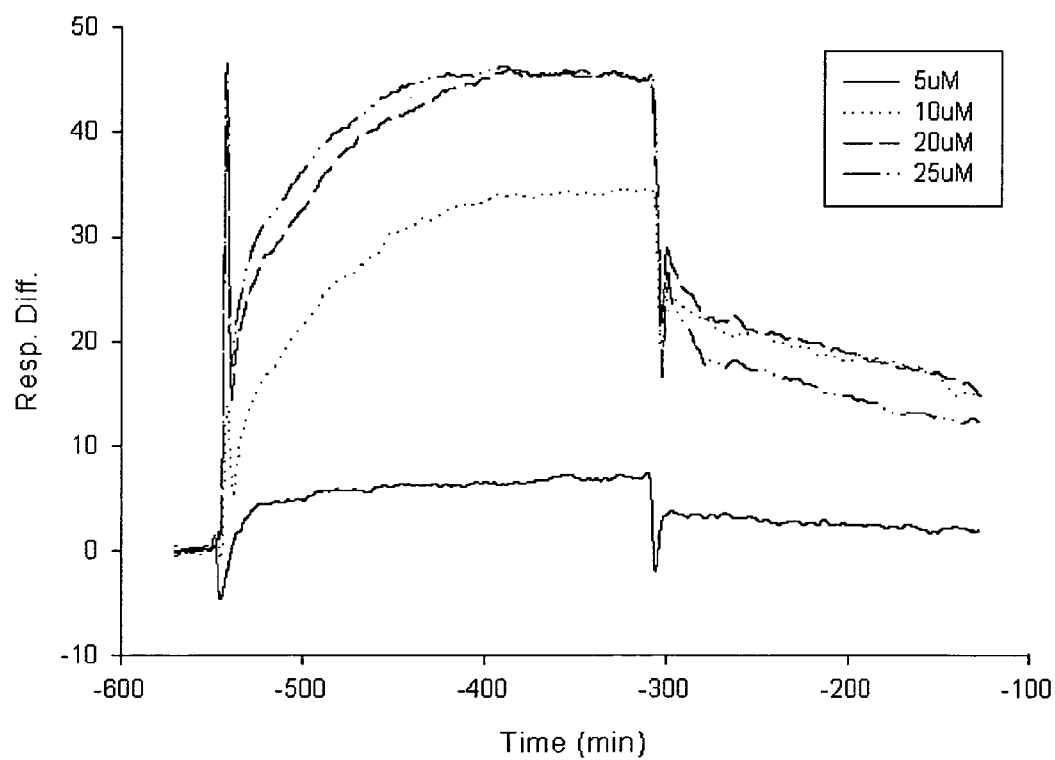

FIGS. 12A-12B show SPR sensorgrams of IGF binding to alginate sulfate, over a range of peptide concentrations. (12A) IGF (5 µM) binding to heparin, alginate sulfate and alginate immobilized on sensor chip SA. Binding was specific for heparin and alginate sulfate while no interactions with immobilized biotinylated alginate were seen. (12B) IGF was injected over immobilized alginate sulfate on sensor chip SA. The SPR sensorgram presents the affinity profile as a function of IGF concentrations.

Figure 13:
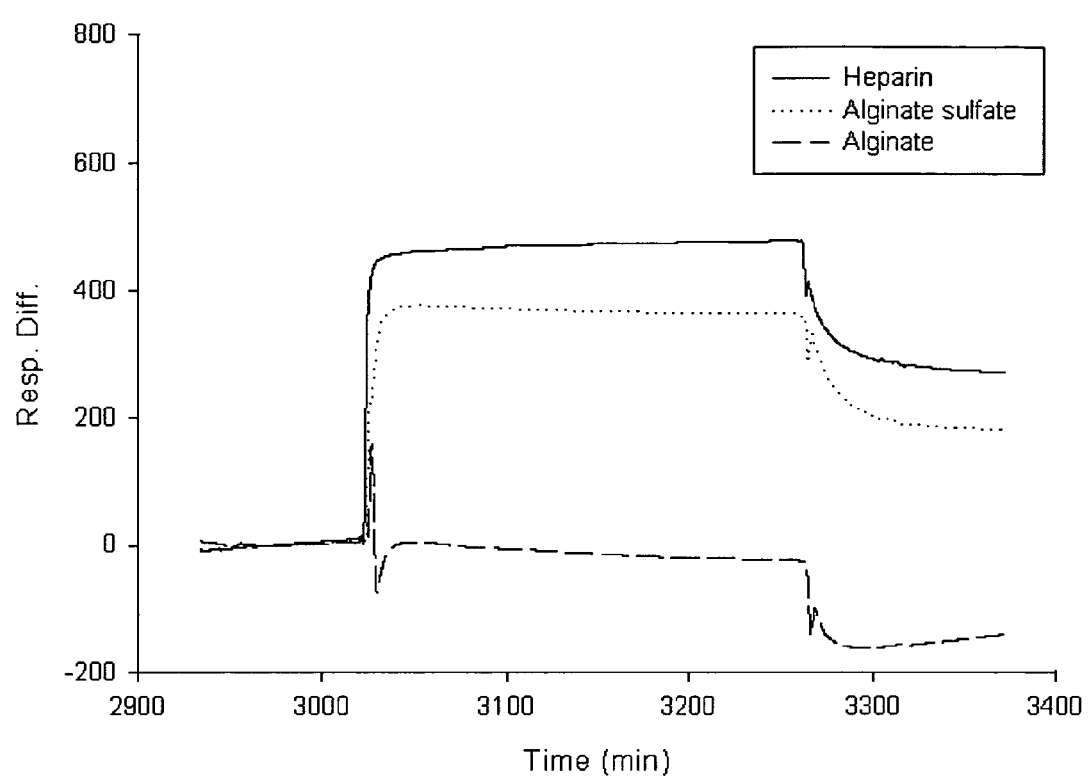

FIG. 13 shows PDGF-AA (550 nM) binding to heparin, alginate sulfate and alginate immobilized on sensor chip SA. Binding was specific for heparin and alginate sulfate while no interactions with immobilized biotinylated alginate were seen.

Figure 14:
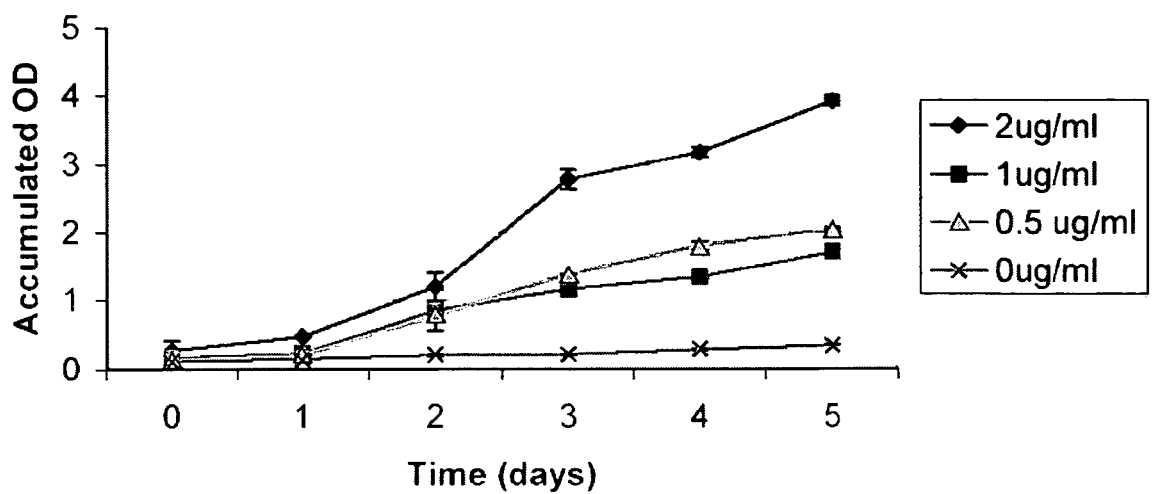

FIG. 14 shows bFGF release profile from alginate capsules fabricated from alginate sulfate. bFGF solutions with a range of concentrations were incubated with alginate/alginate sulfate solution for binding and then the capsules were produced. Released bFGF was analyzed by ELISA.

Figure 15:
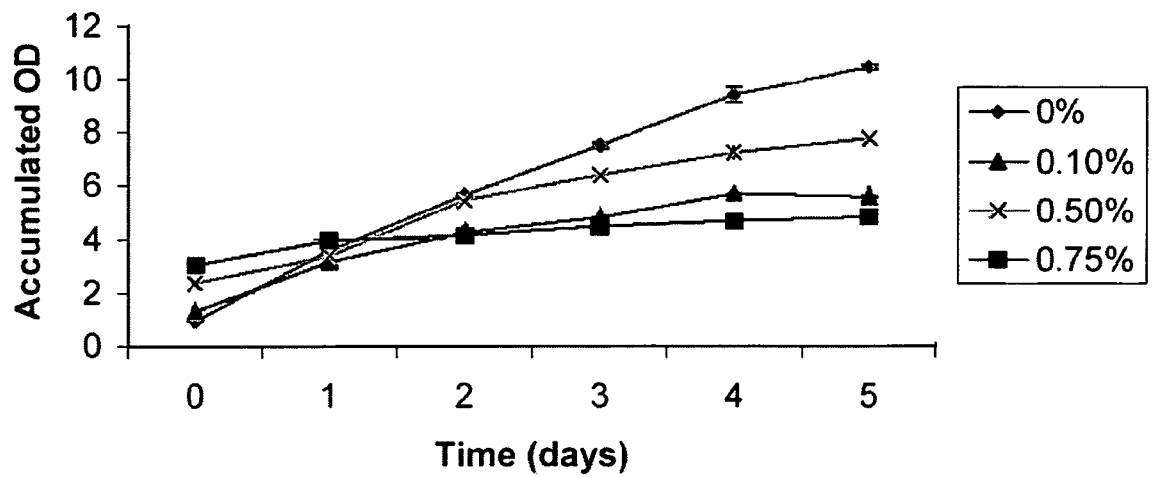

FIG. 15 shows the release profile of bFGF from capsules containing different amounts of alginate sulfate (0, 0.1, 0.5, 0.75, 1% w/v) and the remaining to total of 1% (w/t) was non-modified alginate. bFGF (2 µg/ml) was incubated for binding prior to capsule formation. The released bFGF was analyzed by the direct ELISA method.

Figure 16:
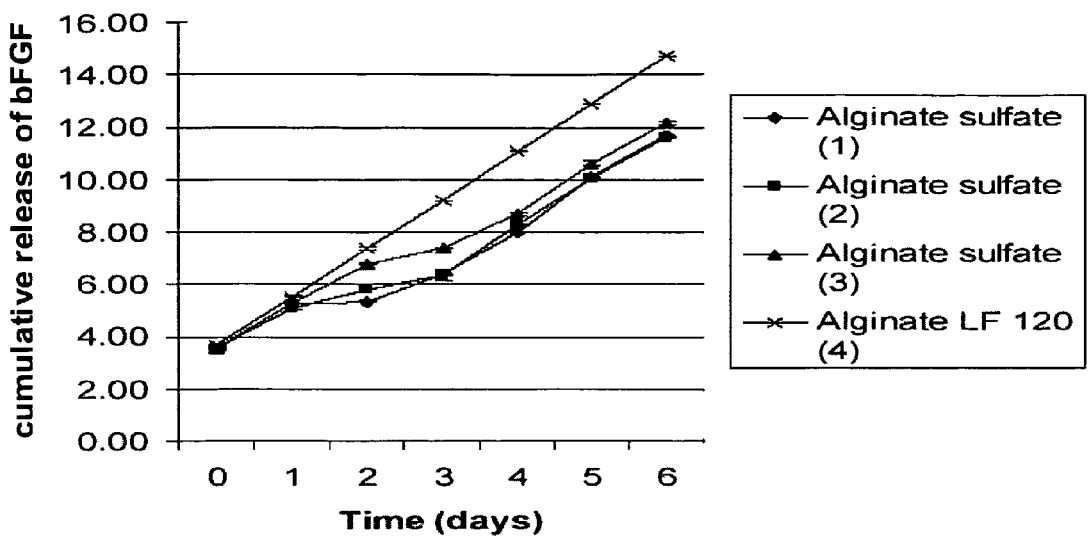

FIG. 16 shows bFGF release from 3 different batches of alginate capsules containing 0.1% alginate sulfate, compared to control capsules. bFGF-containing capsules were placed with medium, incubated at 37° C. for 6 days, and the released bFGF was analyzed by ELISA. The results were interpolated from the calibration curve plotted for known concentrations of bFGF.

Figure 17:
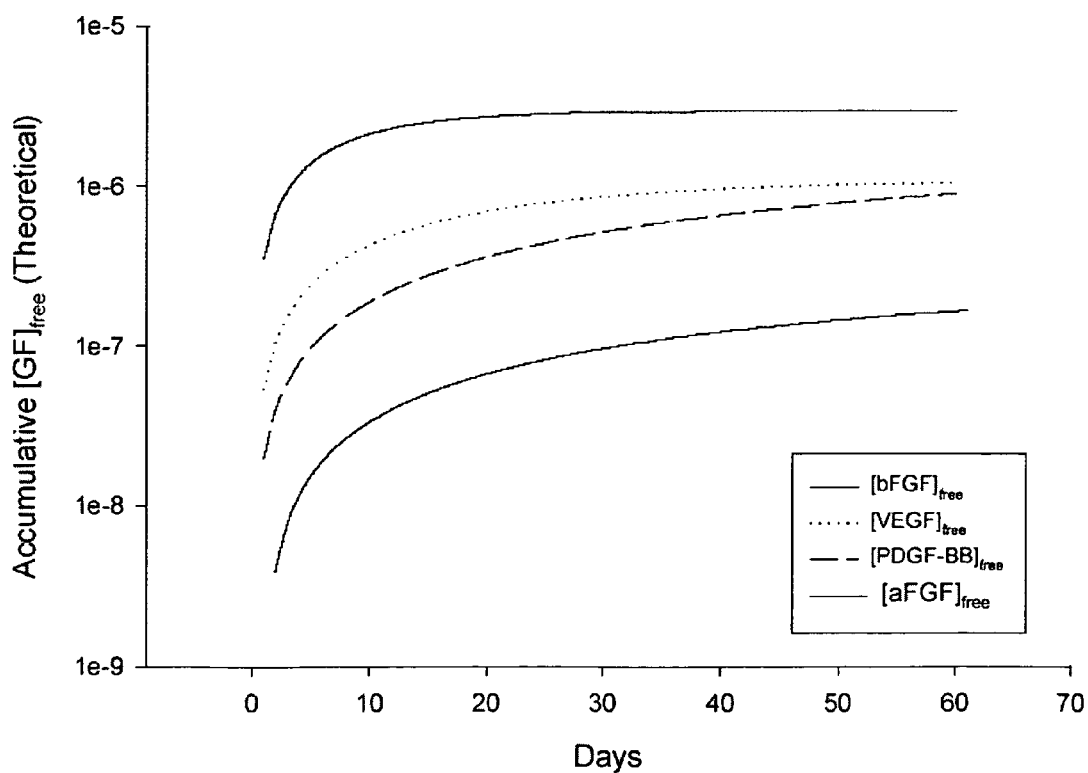

FIG. 17 shows theoretical accumulative (molar concentration) releasing profile of the growth factors: bFGF, VEGF, aFGF, PDGF-BB (for 1 µg loading).

FIGS. 18A-18B show the SEM morphology of alginate/ alginate sulfate scaffolds (18A) versus plain alginate scaffolds 18B): there is no difference in morphology.

FIGS. 19A-19C show the appearance of implanted scaffolds 14 days post-implantation. (19A) In the study group with alginate/alginate sulfate and 10 µg bFG/scaffold, a large capsule full with blood liquid is observed; (19B) in control I group, with alginate and 10 µg bFGF/scaffold, no capsule observed, the scaffolds are partially eroded (arrow); and (19C) in control II with alginate/alginate sulfate without bFGF, the arrow point at scaffold with no capsule. Macroscopic view of hematoxylin and eosin (H&E) stained cross-sections of the scaffold implants and the surrounding tissue, 2 weeks after implantation, are shown on the right: (19A1) Study group, (19B1) Control I and (19C1) Control II (bar indicates 2 mm).

Figure 20A:
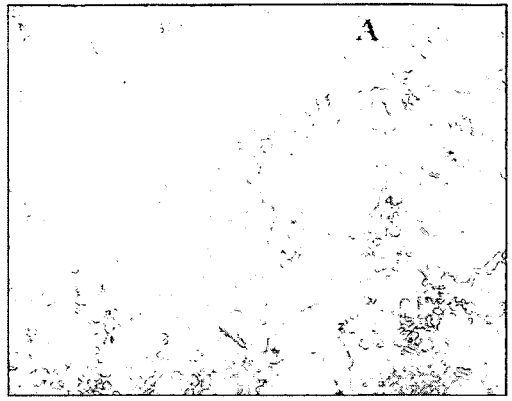
Figure 20B:
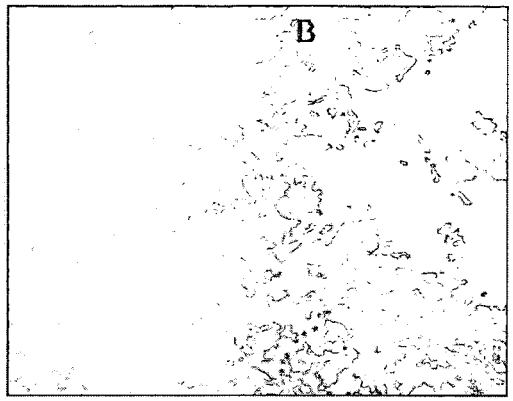
Figure 20C:
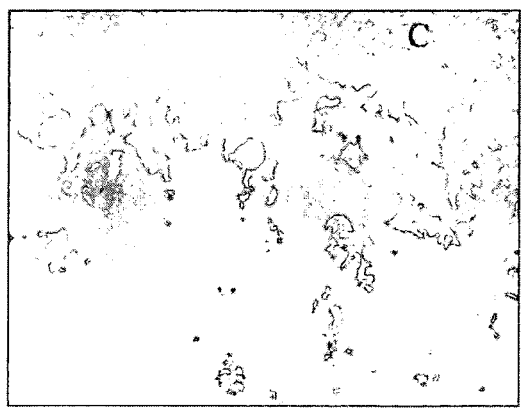

FIGS. 20A-20C show high magnification pictures of H&E stained cross-sections in the scaffold implants, 2 weeks post-implantation. (20A) study group alginate/alginate sulfate/ bFGF; (20B) Control I alginate bFGF; and (20C) Control II alginate/alginate sulfate (bar indicates 100 µm).

Figure 21:
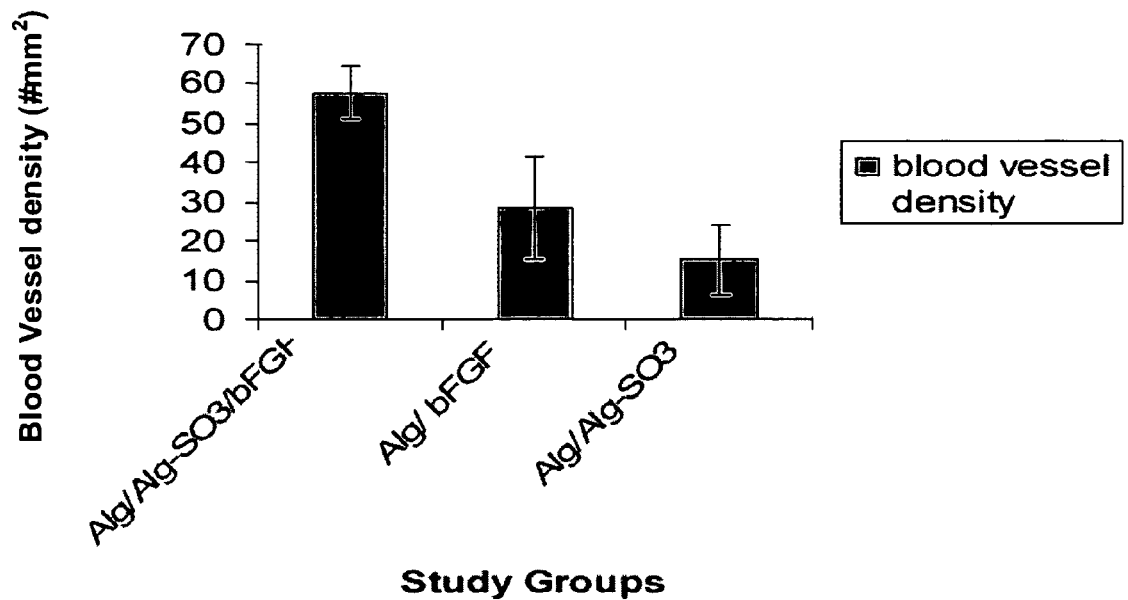

FIG. 21 shows blood vessel density (number per area $mm^2$) in the implanted scaffolds with alginate/alginate sulfate/ bFGF, alginate bFGF, and alginate/alginate sulfate, 14 days post-implantation. P<0.05 (*)

Figure 22:
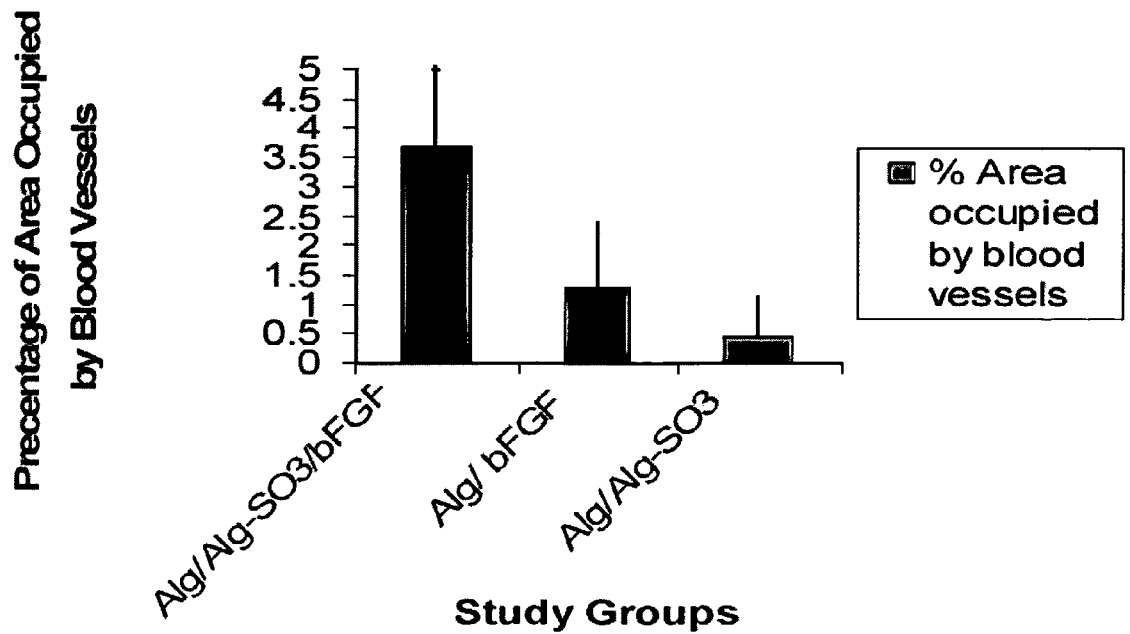

FIG. 22 shows the percentage of area occupied by blood vessels in the implanted scaffolds with alginate/alginate sulfate/bFGF, alginate bFGF, and alginate/alginate, 14 days post-implantation. P<0.05 (*).

Figure 23:
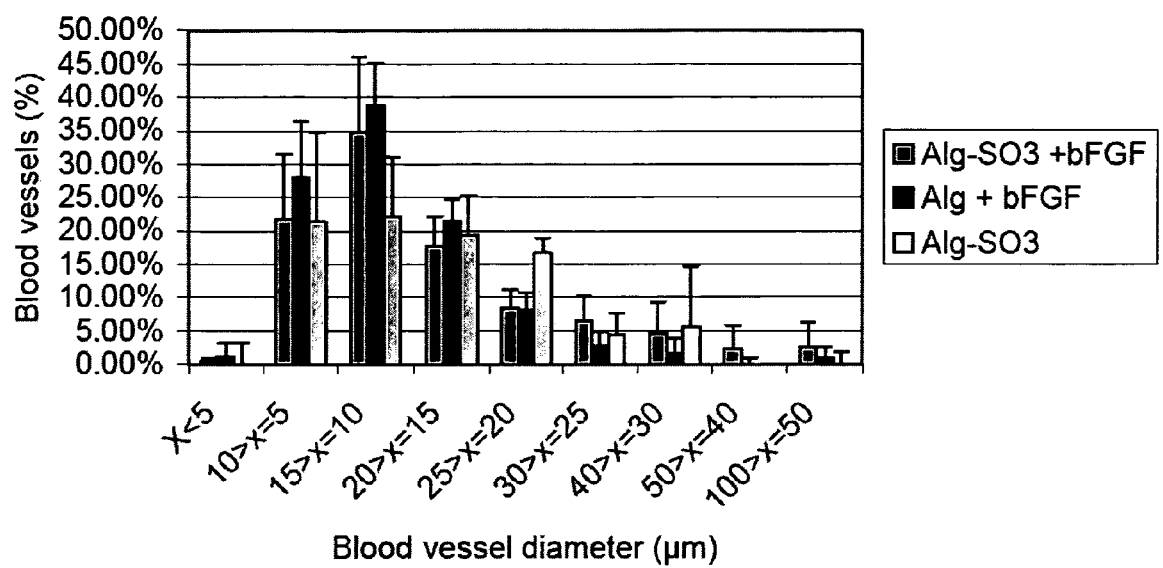
Figure 24A:
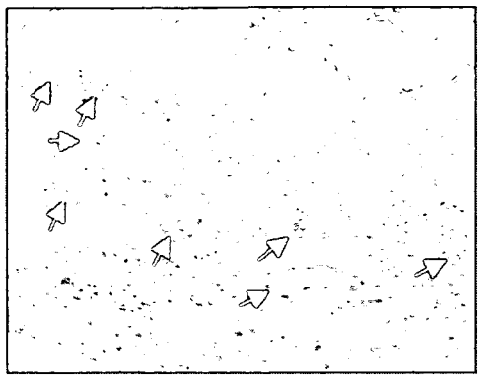
Figure 24B:
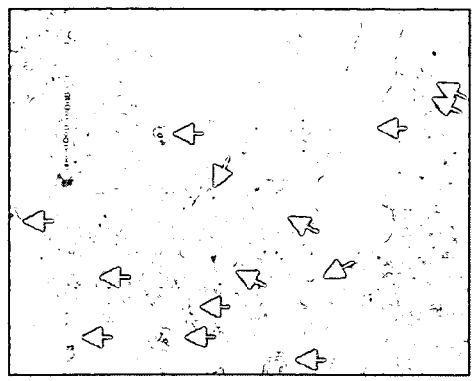
Figure 24C:
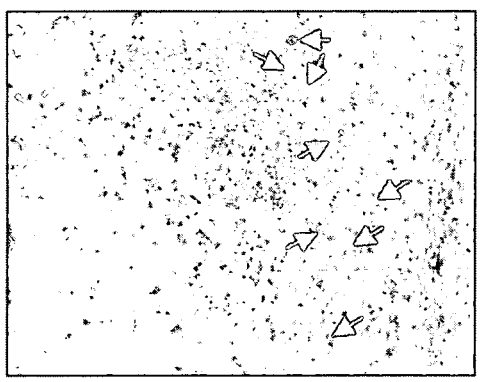
Figure 24D:
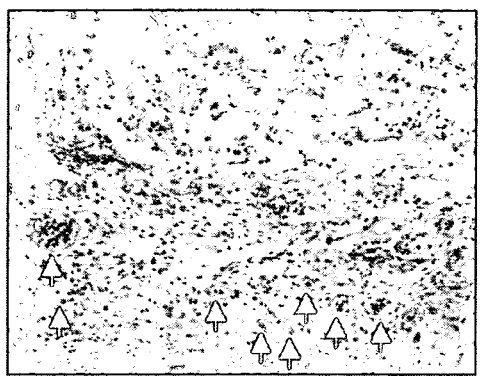
Figure 24E:
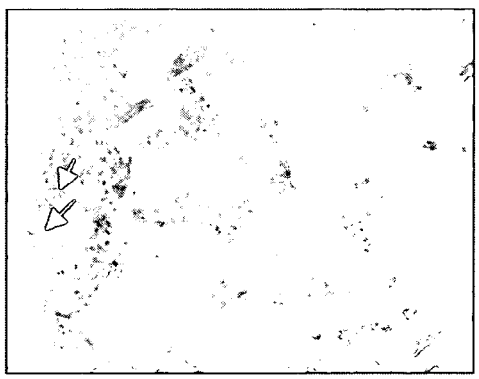
Figure 24F:
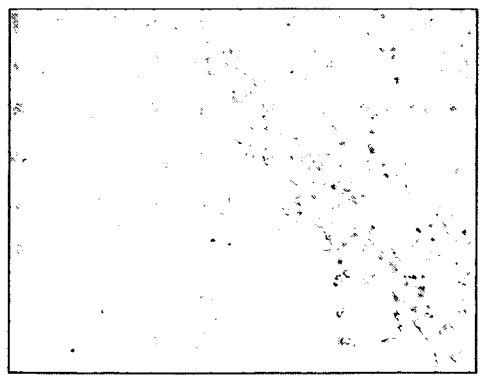

FIG. 23 shows the distribution of blood vessel diameters within the implanted scaffolds with alginate/alginate sulfate/bFGF, alginate bFGF, and alginate/alginate sulfate, 14 days post-implantation. The Y-axis is the % number of blood vessels in each category in every group.

FIGS. 24A-24F show H&E histology of the capsule surrounding the implanted scaffolds. The bFGF-releasing alginate/alginate sulfate scaffolds have high cellular content and the blood vessels are large (24A, 24B). In contrast, the control groups have lower cellular content as well as blood vessels. (24C, 24D) Control I and (24E, 24F) Control II (bar indicates 100 μm).

Figure 1:
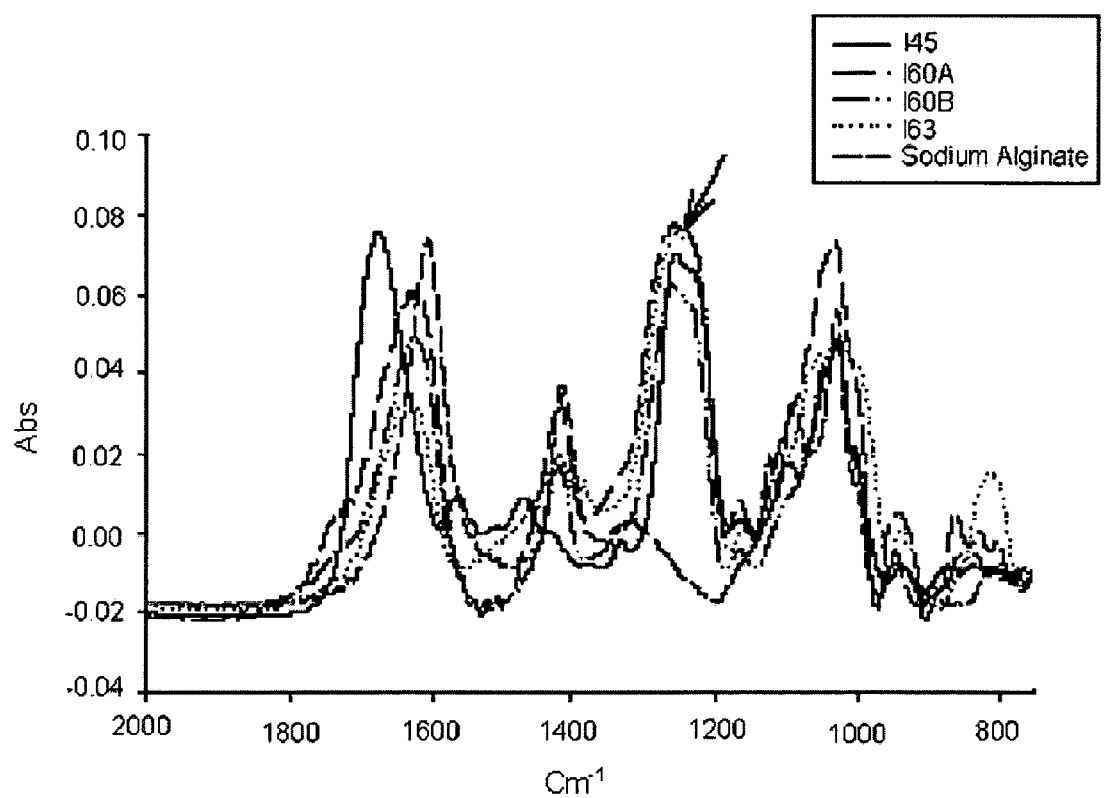
FIG. 1 shows FTIR spectra of alginate sulfate (I-49, I-60A, I-60B and I-63) and raw material sodium alginate. The arrow point towards a new major peak at ~1250 $cm^{-1}$ proves controlled sulfation of alginate.
Figure 2A:
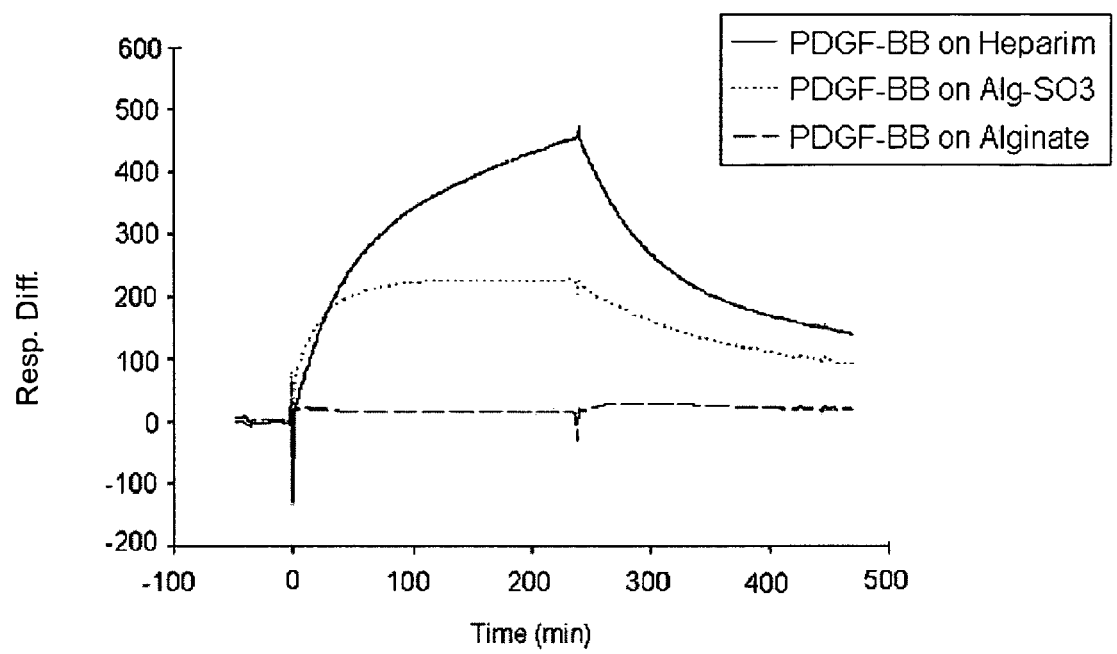
FIGS. 2A-2B show SPR sensorgrams of PDGF-BB binding to alginate sulfate, over a range of peptide concentrations. (2A) PDGF-BB (400 nM) binding to heparin, alginate sulfate and alginate immobilized on sensor chip SA. Binding was specific for heparin and alginate sulfate, while no interactions with immobilized biotinylated alginate were seen. (2B) PDGF-BB was injected over immobilized alginate sulfate. The SPR sensorgram presents the affinity profile as a function of PDGF-BB concentrations.
Figure 2B:
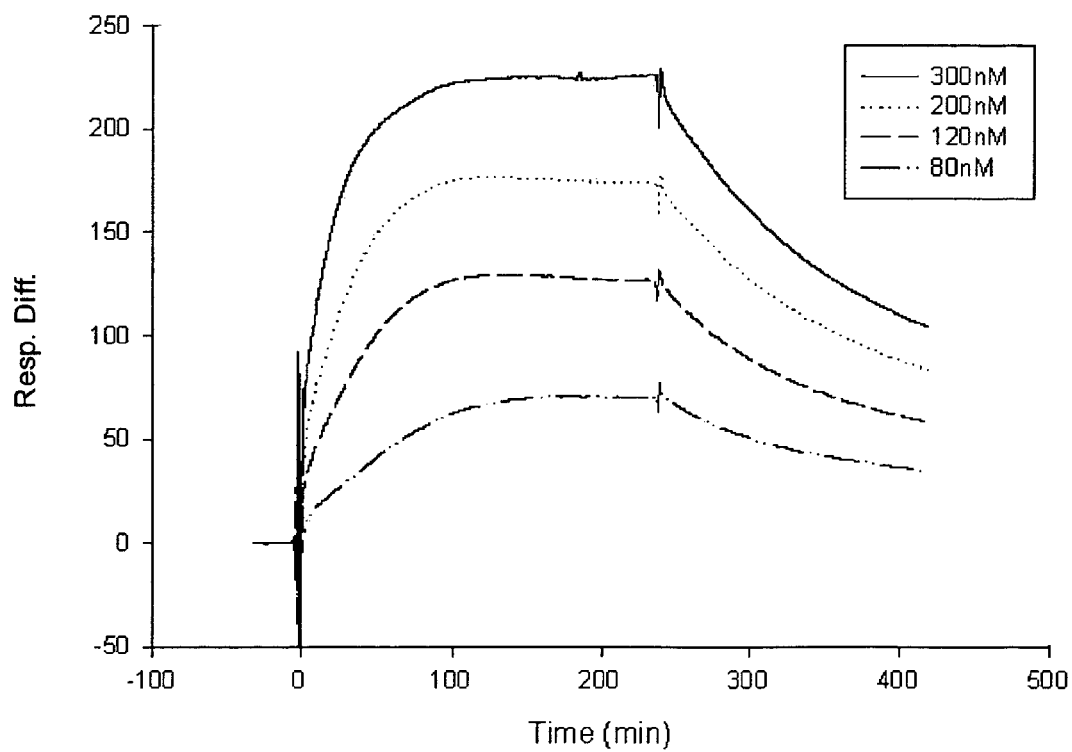
Figure 3A:
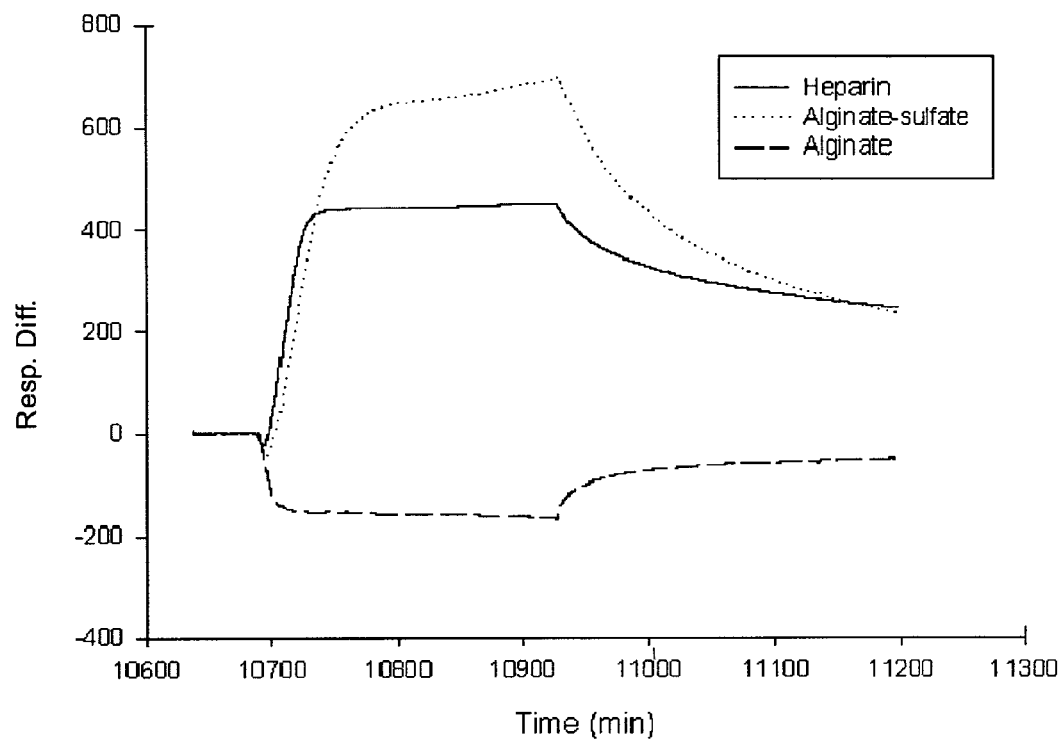
FIGS. 3A-3B show SPR sensorgrams of bFGF binding to alginate sulfate, over a range of peptide concentrations. (3A) bFGF (1 µM) binding to heparin, alginate sulfate and alginate immobilized on sensor chip SA. Binding was specific for heparin and alginate sulfate while no interactions with immobilized biotinylated alginate were seen. (3B) bFGF was injected over immobilized alginate sulfate on sensor chip SA.
Figure 3B:
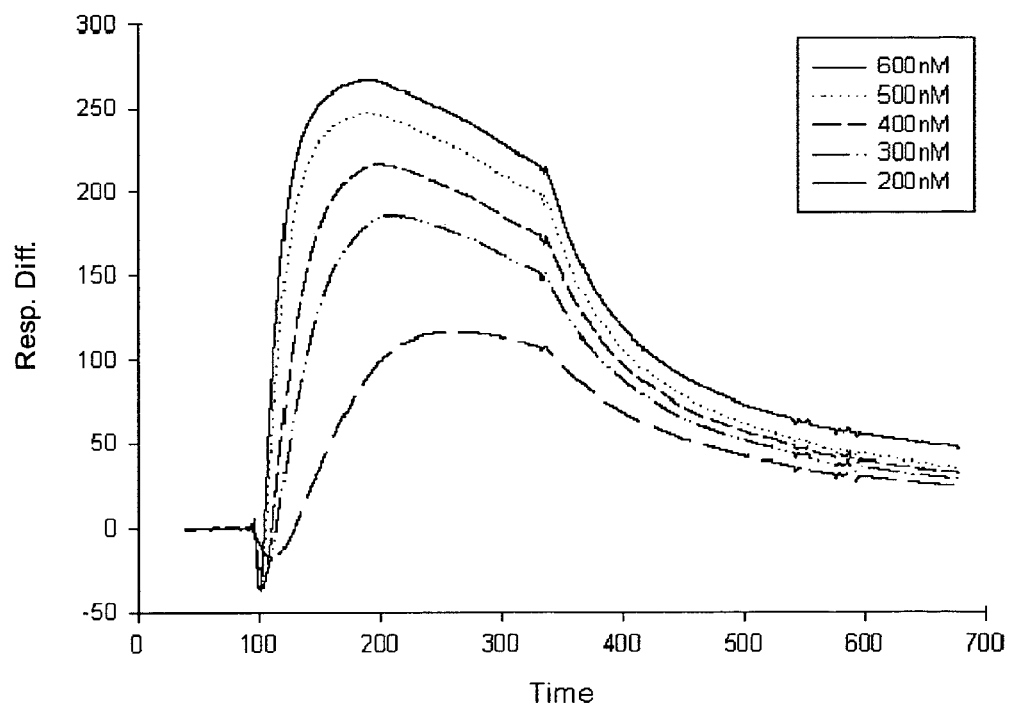

FIGS. 25A1-A3, B1-B3, C1-C3 show immunohistochemistry staining for αSMA (smooth muscle actin) (25A1, 25B1, and 25C1), α-Lectin (endothelial cells) (25A2, 25B2, 25C2), and ED1 (macrophages) (25A3, 25B3, 25C3) of the capsule surrounding the implanted scaffolds. (25A) alginate/alginate sulfate/bFGF. (25B) alginate/bFGF and (25C) alginate/alginate sulfate. (bar indicates 100 μm).

Figure 26:
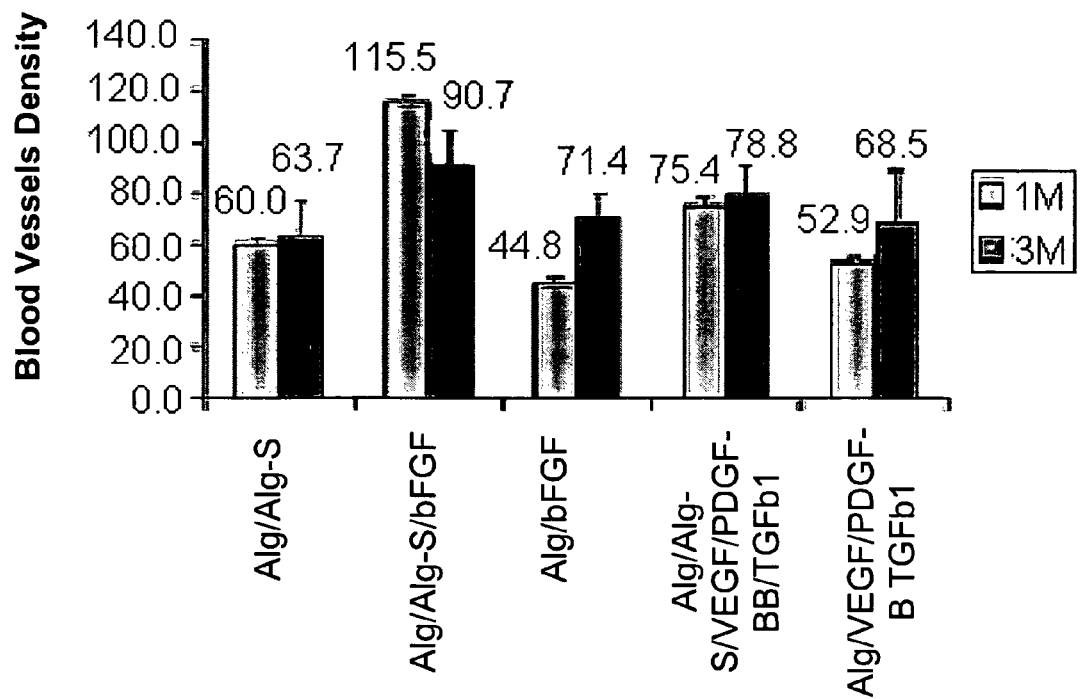

FIG. 26 shows blood vessel density (number per area $mm^2$) in the implanted scaffolds with alginate/alginate sulfate, alginate/alginate sulfate/bFGF, alginate/bFGF, alginate/alginate sulfate/VEGF/PDGF-BB/TGFβ1, or alginate/VEGF/PDGF-BB/TGFβ1, 1 and 3 months post-implantation. P<0.05.

Figure 27:
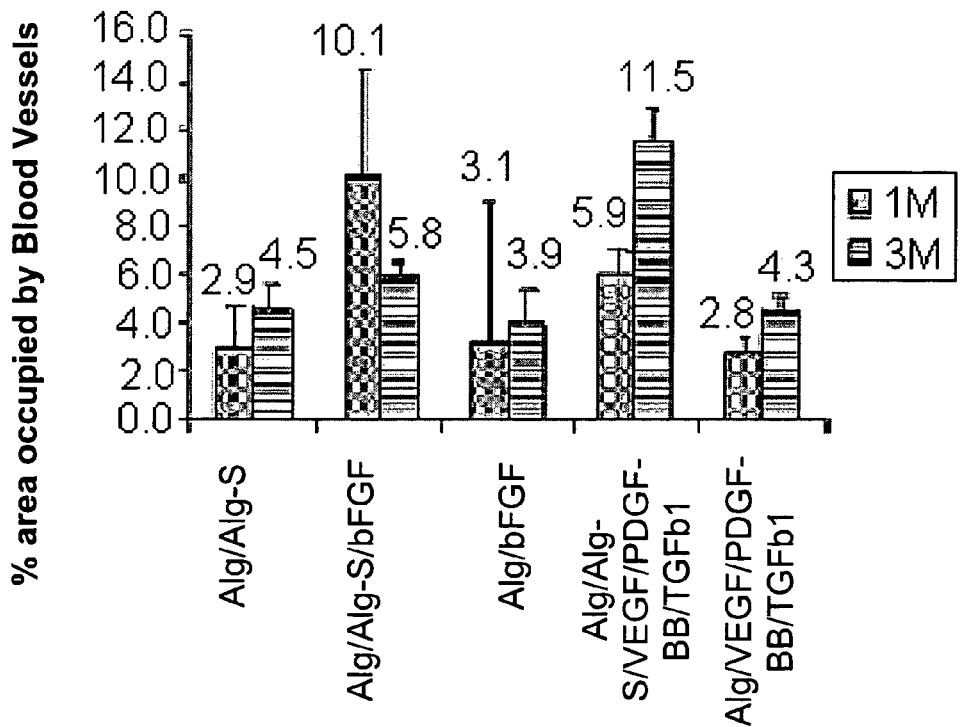

FIG. 27 shows the percentage of the area occupied by blood vessels in the implanted scaffolds, 1 and 3 months post-implantation. P<0.05.

Figure 28:
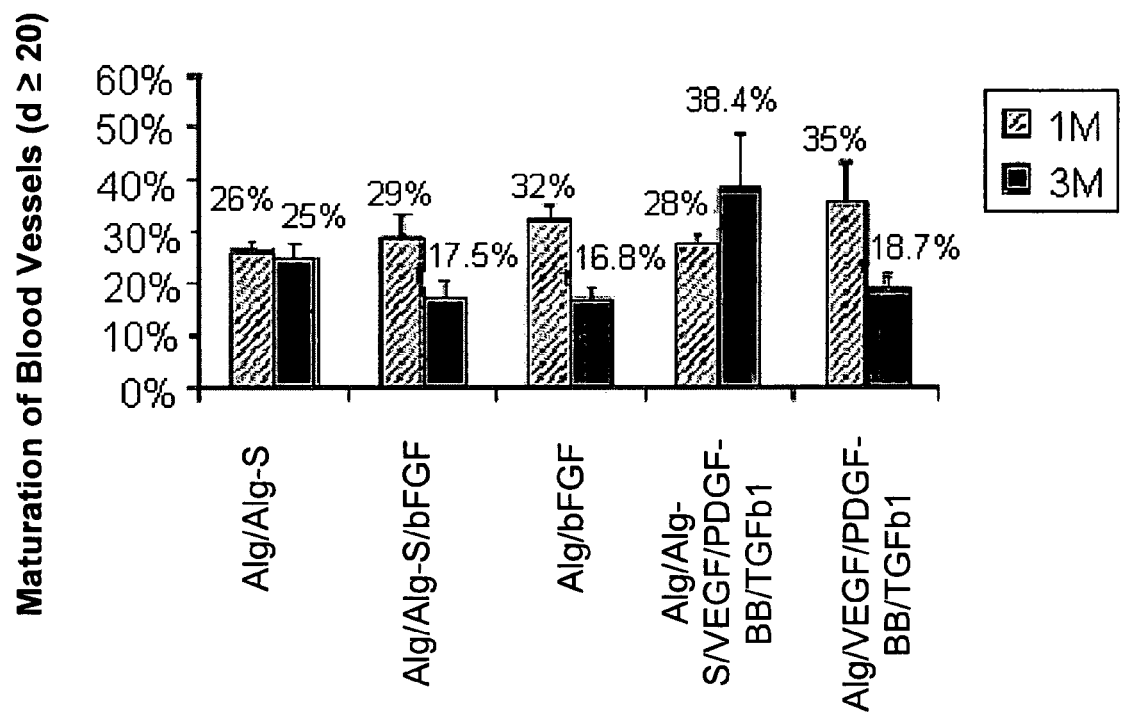

FIG. 28 shows maturation of blood vessels in the implanted scaffolds; 1 and 3 months post-implantation. P<0.05.

FIGS. 29A-29E show immunohistochemistry analysis of the capsule surrounding the implanted scaffolds 1 month post-implantation. A-Lectin staining for endothelial cells (29A-29E 1&2), αSMA staining for smooth muscle actin (29A3-29E3). (29A) alginate/alginate sulfate/VEGF/PDGF-BB/TGFβ1, (29B) alginate/VEGF/PDGF-BB/TGFβ1, (29C) alginate/alginate sulfate/bFGF, (29D) alginate/bFGF, (29E) alginate/alginate sulfate. (bar indicates 100 μm).

FIGS. 30A-30E show immunohistochemistry of the capsule surrounding the implanted scaffolds 3 months-post implantation. A-Lectin staining (30A-30E 1&2), αSMA staining (30A3-30E3). (30A) alginate/alginate sulfate/VEGF/PDGF-BB/TGFβ1, (30B) alginate/VEGF/PDGF-BB/TGFβ1, (30C) alginate/alginate sulfate/bFGF, (30D) alginate/bFGF, and (30E) alginate/alginate sulfate. (bar indicates 100 μm).

Figure 31:
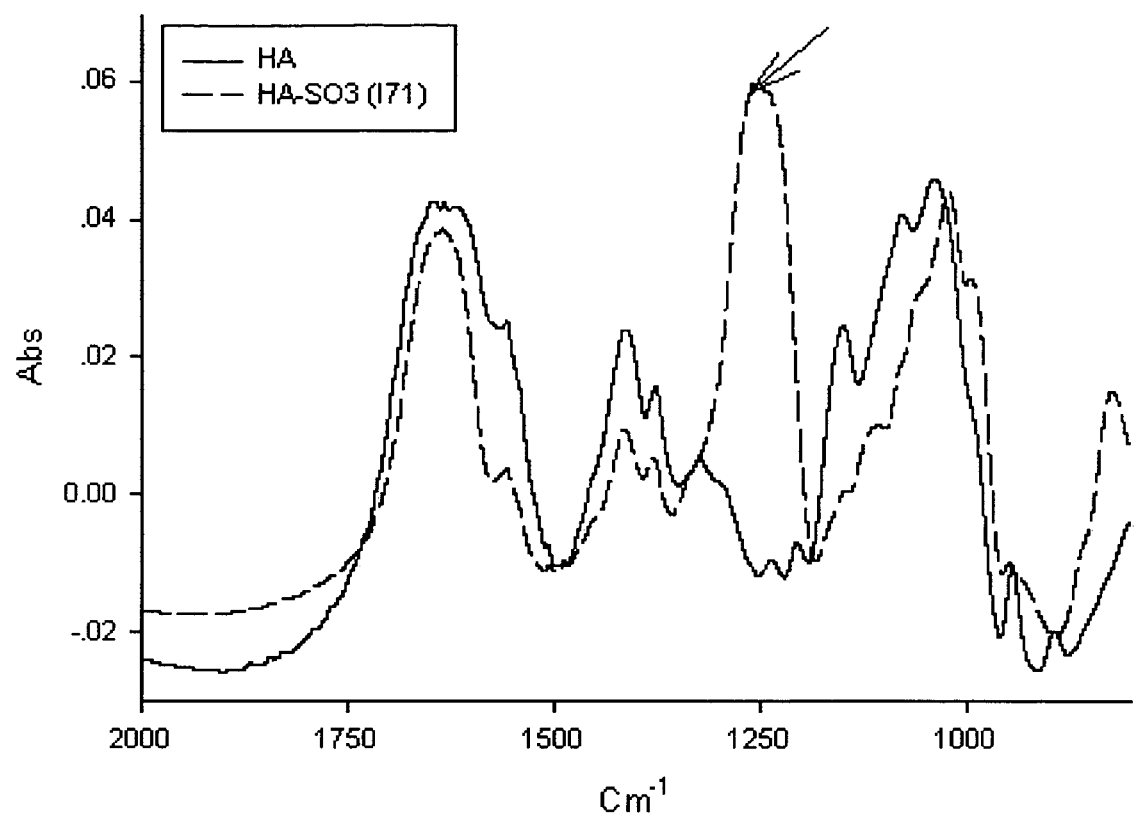

FIG. 31 shows hyaluronan (HA) sulfation and product analysis. FTIR spectra of hyaluronan sulfate (I-71) and raw material hyaluronic acid. The arrow points towards a new major peak at ~1250 cm-1 proving controlled sulfation of HA.

Figure 32A:
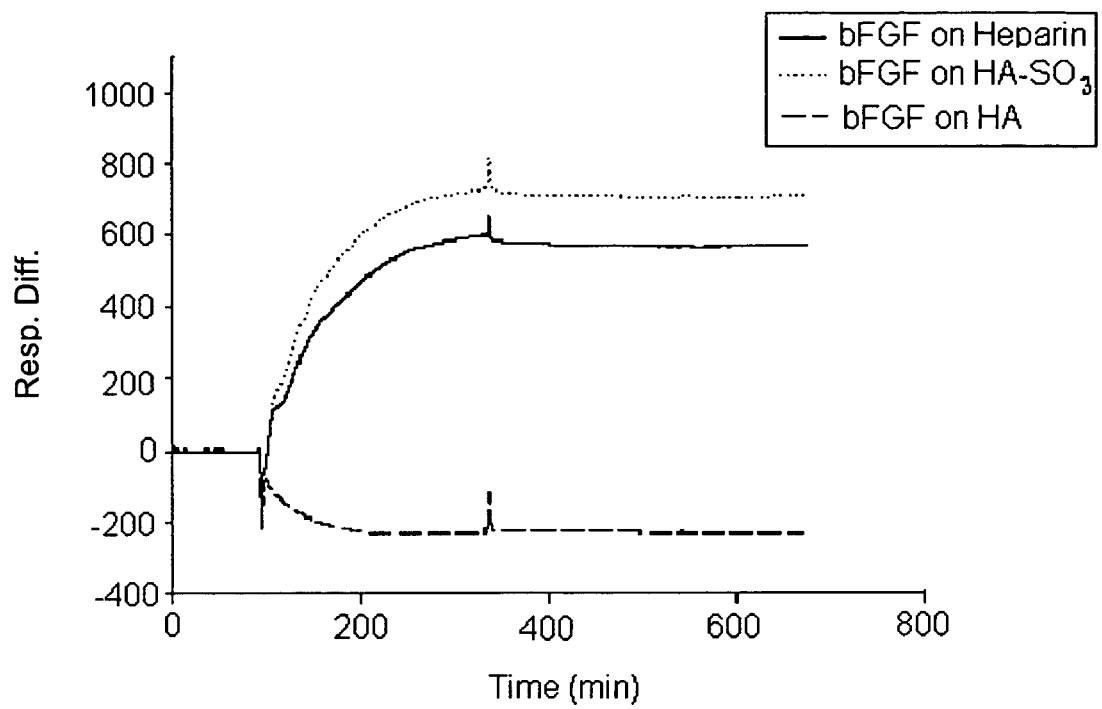
Figure 32B:
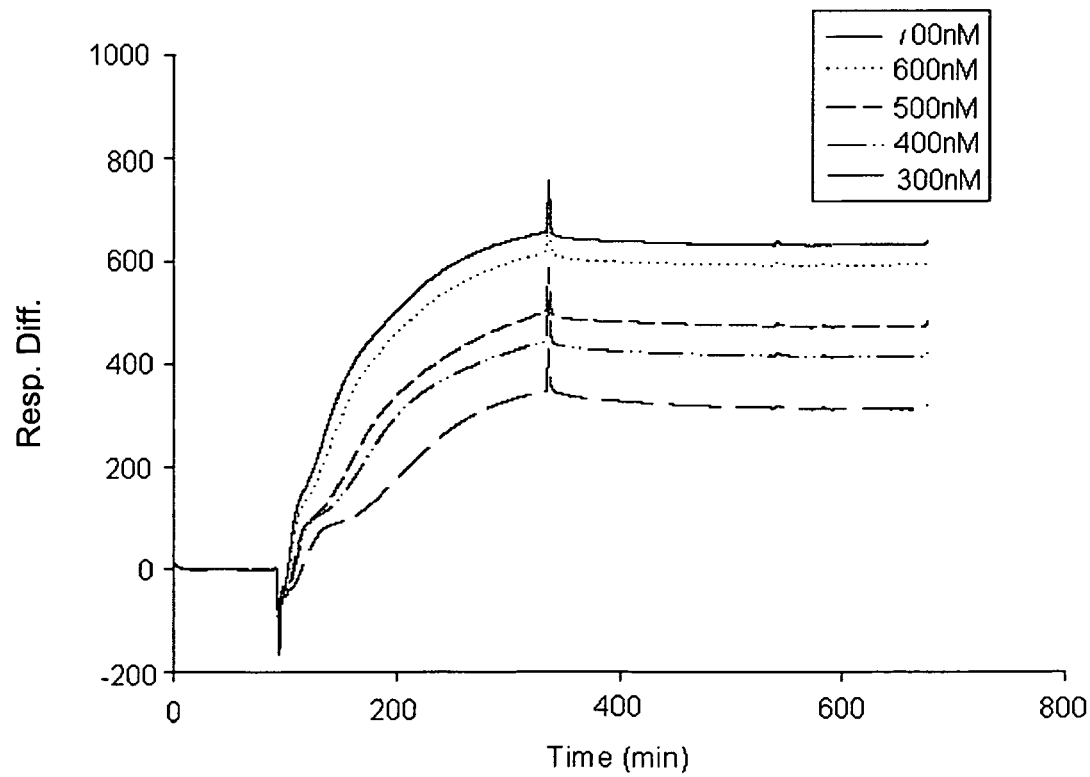

FIGS. 32A-32B show SPR sensorgrams of bFGF binding to hyaluronan-sulfate, over a range of peptide concentrations. (32A) bFGF (700 nM) binding to heparin, HA-sulfate and HA immobilized on sensor chip SA. Binding was specific for heparin and HA sulfate while no interactions with immobilized biotinylated HA were seen. (32B) bFGF was injected over immobilized HA sulfate. The SPR sensorgram presents the affinity profile as a function of bFGF concentrations.

Figure 33A:
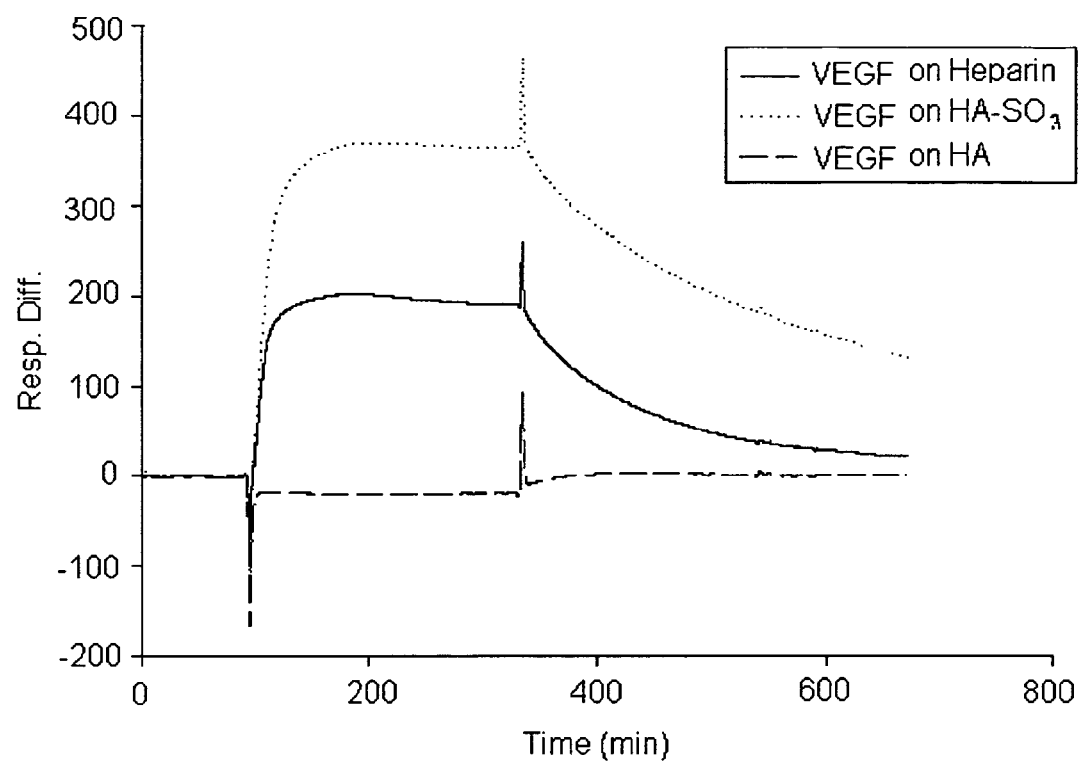
Figure 33B:
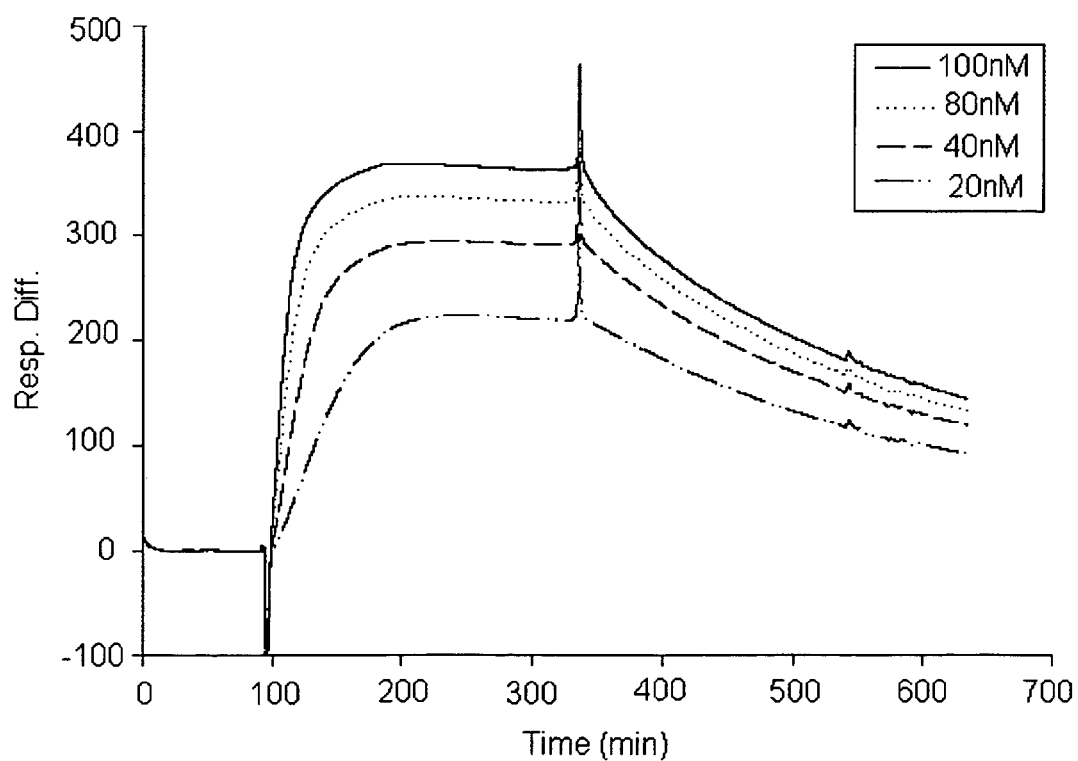

FIGS. 33A-33B show SPR sensorgrams of VEGF binding to HA-sulfate, over a range of peptide concentrations. (33A) VEGF (100 nM) binding to heparin, HA-sulfate and HA immobilized on sensor chip SA. Binding was specific for heparin and HA sulfate while no interactions with immobilized biotinylated HA were seen. (33B) VEGF was injected over immobilized HA. The SPR sensorgram presents the affinity profile as a function of VEGF concentrations.

Figure 34A:
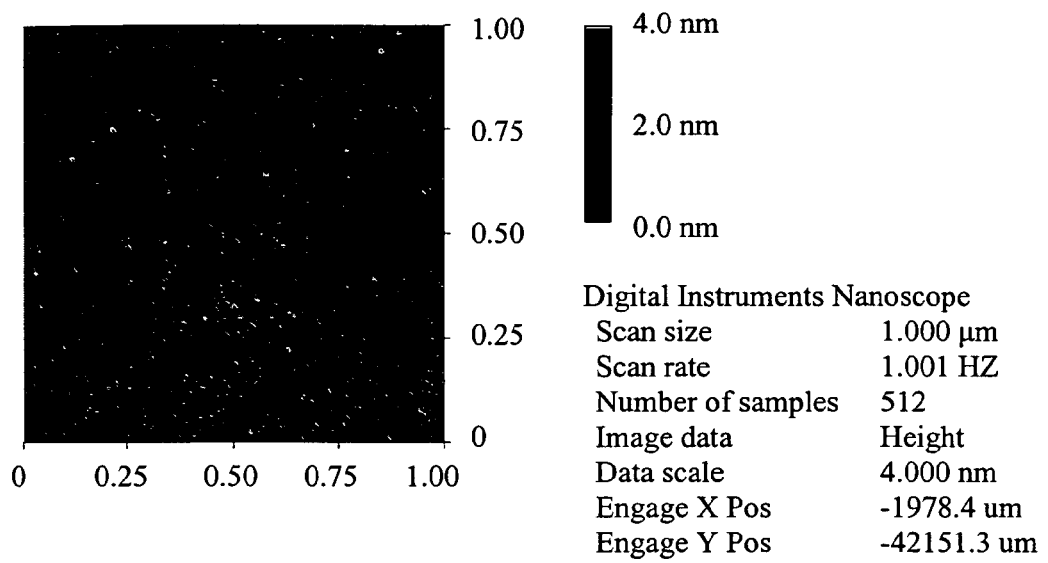
Figure 34B:
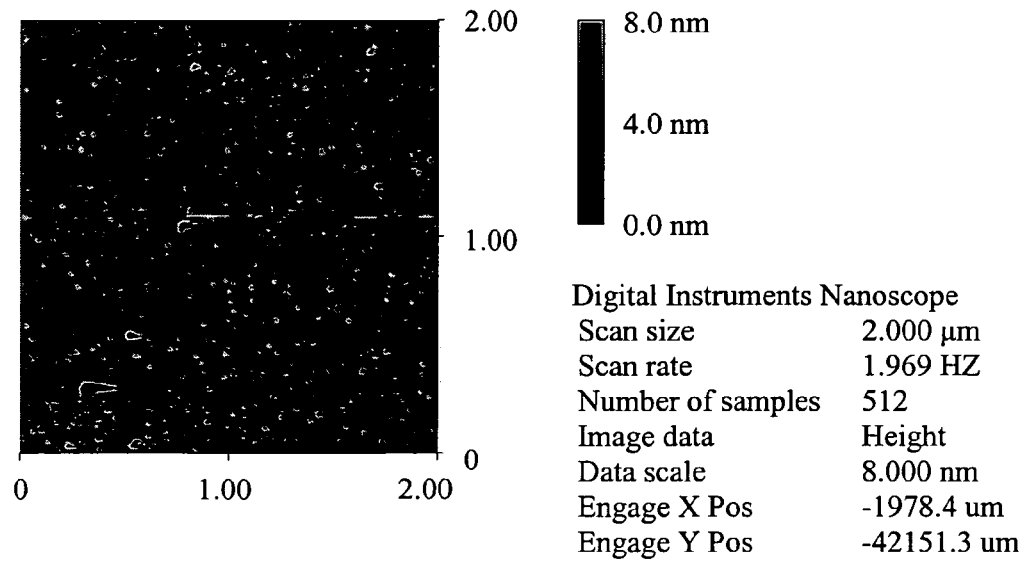

FIGS. 34A-34B show alginate sulfate and alginate sulfate/bFGF, respectively, on mica surface as scanned by atomic force microscope (AFM).

FIG. 35 shows nanoparticles of bioconjugates of alginate sulfate (A) 8 nM, (B) 80 nM, (C) 800 nM and 80 nM bFGF (A1, B1, C1) or VEGF (A2, B2, C2, 80 nM) on mica surface as scanned by AFM. X=0.50 μm/div, Z=10.00 nm/div.

Figure 36:
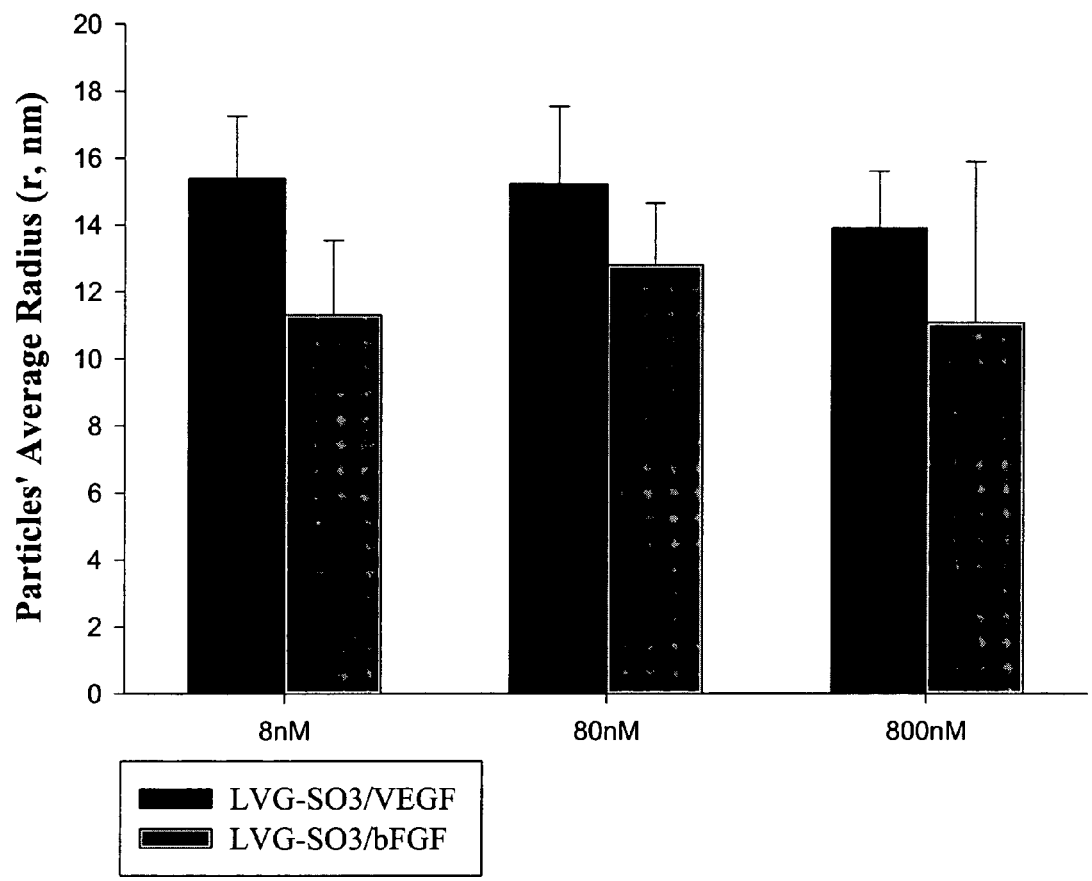

FIG. 36 depicts calculated particles size (r) from AFM pictures of the bFGF or VEGF bioconjugates with alginate sulfate. Alginate sulfate (8, 80 and 800 nM), bFGF or VEGF (80 nM). P<0.01.

Figure 37:
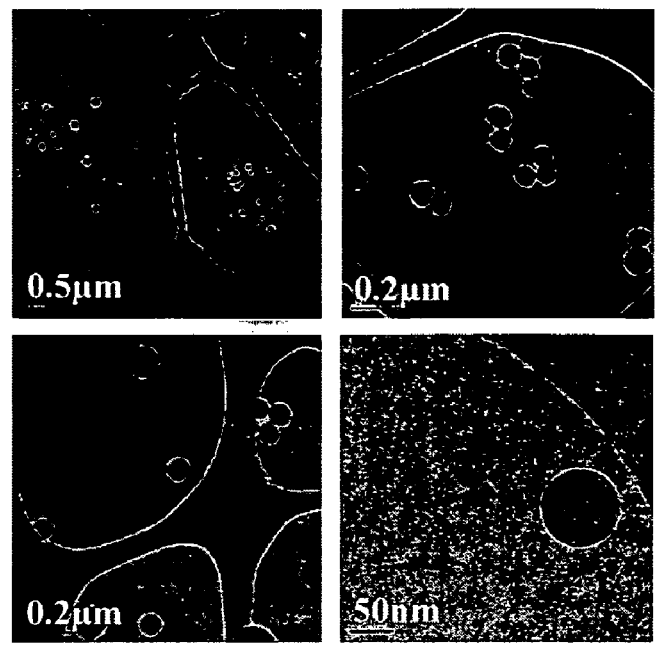

FIG. 37 show nanoparticles of wet samples of bioconjugates of alginate sulfate/bFGF observed by cryo-transmission electron microscope (TEM).

Figure 38:
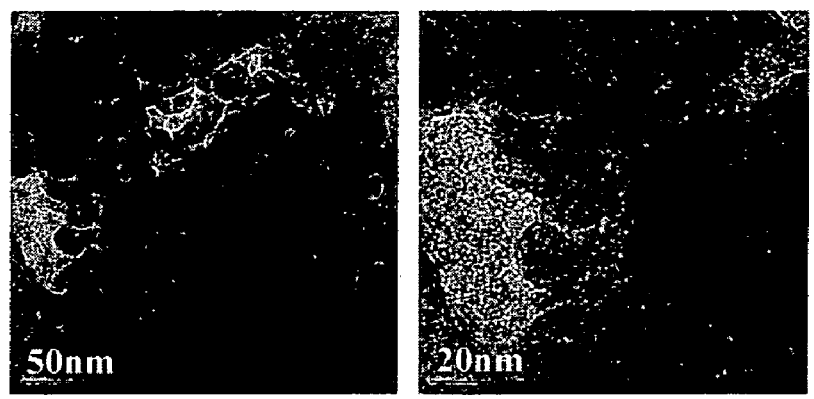

FIG. 38 show dry nanoparticles of bioconjugates of alginate sulfate/bFGF observed by TEM.

DETAILED DESCRIPTION OF THE INVENTION

The present invention relates, in one aspect, to a bioconjugate comprising a sulfated polysaccharide and at least one bioactive polypeptide capable of binding a sulfate group of said sulfated polysaccharide. These bioconjugates are useful for sustained release of said at least one bioactive peptide(s) when the bioconjugate is administered to a mammal, preferably a human.

The at least one bioactive polypeptide may be a positively charged polypeptide, a heparin-binding polypeptide, or both. The term "bioactive polypeptide" as used herein refers to a polypeptide exhibiting a variety of pharmacological activities in vivo and include, without being limited to, growth factors, cytokines, chemokines, angiogenic factors, immunomodulators, hormones, and the like.

In the present application, the terms "polypeptide" and "proteins" are used interchangeably.

The term "positively charged polypeptide" refers to a polypeptide/protein that has a positive net charge at physiological pH of about pH=7.5. Examples of positively charged proteins include, but are not limited to, insulin, glatiramer acetate (also known as Copolymer 1 or Cop 1), antithrombin III, interferon (IFN)-γ (also known as heparin-binding protein), IGF, somatostatin, erythropoietin, luteinizing hormone-releasing hormone (LH-RH) and interleukins such as IL-2 and IL-6.

The term "heparin-binding protein or polypeptide" refers to proteins that have clusters of positively-charged basic amino acids and form ion pairs with specially defined negatively-charged sulfo or carboxyl groups on the heparin chain (See Capila and Linhardt, 2002). Examples of heparin-binding proteins include, but are not limited to, thrombopoietin (TPO); proteases/esterases such as antithrombin III (AT III), serine protease inhibitor (SLP1), C1 esterase inhibitor (C1 INH) and Vaccinia virus complement control protein (VCP); growth factors such as a fibroblast growth factor (FGF, aFGF, bFGF), a FGF receptor, vascular endothelial growth factor (VEGF), insulin-like growth factor (IGF), hepatocyte growth factor (HGF), transforming growth factor β1 (TGF-β1), a platelet-derived growth factor (PDGF, PDGF-AA and PDGF-BB), and epidermal growth factor (EGF); chemokines such as platelet factor 4 (PF-4, now called CXC chemokine ligand 4 or CXCL4), stromal cell-derived factor-1 (SDF-1), IL-6, IL-8, RANTES (Regulated on Activation, Normal T Expressed and Secreted), monocyte chemoattractant protein-1 (MCP-1), macrophage inflammatory peptide-1 (MIP- 1), lymphotactin, and fractalkine; lipid or membrane-binding proteins such as an annexin, apolipoprotein E (ApoE); pathogen proteins such as human immunodeficiency virus type-1 (HIV-1) coat proteins e.g. HIV-1 gp120, cyclophilin A (CypA), Tat protein, viral coat glycoprotein gC, gB or gD of herpes simplex virus (HSV), an envelope protein of Dengue virus, circumsporozoite (CS) protein of *Plasmodium falciparum*, bacterial surface adhesion protein OpaA; and adhesion proteins such as 1- and P-selectin, heparin-binding growth-associated molecule (HB-GAM), thrombospondin type I repeat (TSR), and amyloid P (AP).

In preferred embodiments of the present invention, the at least one heparin-binding polypeptide is selected from PDGF-BB, PDGF-AA, bFGF, aFGF, VEGF, TGFβ1, IL-6, TPO, SDF-1, HGF, EGF or IGF.

In other preferred embodiments of the invention, the at least one bioactive polypeptide is an angiogenic factor or a growth factor exhibiting angiogenic activity such as TGF-β1, VEGF, bFGF, aFGF, PDGF-BB, IGF, and a combination thereof.

In a more preferred embodiment of the invention, said at least one angiogenic factor is bFGF. In yet another more preferred embodiment of the invention, the bioactive polypeptide is VEGF or a combination of VEGF, PDGF-BB and TGF-β1.

In accordance with the present invention, the sulfated polysaccharides forming the bioconjugate may be composed of different recurring monosaccharide units, may be of different lengths, and may have different types of bonds linking said units. The sulfated polysaccharides may be linear as sulfated cellulose, branched as sulfated glycogen, and may vary in length; for example, it may be as small as a sulfated tetra- or tri-saccharide. The sulfated polysaccharide may be a homopolysaccharide including, but not limited to, starch, glycogen, cellulose or chitin or a heteropolysaccharide including, but not limited to, alginic acid (alginate) salts and hyaluronic acid.

In a preferred embodiment of the invention, the polysaccharide comprises uronic acid residues such D-glucuronic, D-galacturonic, D-mannuronic, L-iduronic, and L-guluronic acids. Examples of polysaccharides comprising uronic acid residues include, but are not limited to, alginic acid salts, preferably sodium alginate, pectin, gums and mucilages from plant sources; and glycosaminoglycans (GAGs) from animal sources including hyaluronic acid (hyaluronan). The sulfated polysaccharides comprising uronic acid can be chemically sulfated or may be naturally sulfated polysaccharides.

In one preferred embodiment of the present invention, the sulfated polysaccharide in the bioconjugate is alginate sulfate. In another embodiment the sulfated polysaccharide is hyaluronan sulfate.

Alginic acid is a linear polysaccharide obtained from brown algae and seaweed and consist of β-1,4-linked glucuronic and mannuronic acid units. As used herein, the term "alginate" refers to a polyanionic polysaccharide copolymer derived from sea algae (e.g., *Laminaria hyperborea, L. digitata, Eclonia maxima, Macrocystis pyrifera, Lessonia nigrescens, Ascophyllum codosum, L. japonica, Durvillaea antarctica,* and *D. potatorum*) and which includes β-D-mannuronic (M) and α-L-guluronic acid (G) residues in varying proportions.

An alginate suitable for use in the present invention has a ratio between α-L-guluronic acid and β-D-mannuronic preferably ranging between 1:1 to 3:1, more preferably between 1.5:1 and 2.5:1, most preferably about 2, and has a molecular weight ranging preferably between 1 to 300 kDa, more preferably between 5 to 200 kDa, more preferably between 10 to 100 kDa, preferably between 20 to 50 kDa.

Hyaluronic acid is composed of repeating dimeric units of glucuronic acid and N-acetyl glucosamine and forms the core complex proteoglycans aggregates found in the extracellular matrix.

In preferred embodiments, the bioconjugate of the invention is selected from the group consisting of aFGF-alginate sulfate, bFGF-alginate sulfate, PDGF-BB-alginate sulfate, PDGF-AA-alginate sulfate, VEGF-alginate sulfate, TGFβ 1-alginate sulfate, IL-6-alginate sulfate, TPO-alginate sulfate, SDF-1-alginate sulfate, HGF-alginate sulfate, EGF-alginate sulfate, IGF-alginate sulfate, bFGF-hyaluronan sulfate and VEGF-hyaluronan sulfate.

In a most preferred embodiment, the bioconjugate is bFGF-alginate sulfate.

The present invention is illustrated by the results obtained with the sulfated polysaccharides alginate sulfate and sulfated hyaluronan. We show herein that alginate and hyaluronic are sulfated and converted into reactive polymers capable of specifically interacting with at least one positively-charged polypeptide and/or heparin-binding polypeptide, forming a bioconjugate capable of sustaining the release of said at least one polypeptide. By sulfating the polysaccharides, we endowed them with properties which allowed binding and controlled release of important signal proteins such as various cytokines and growth factors. Alginate sulfate and hyaluronan sulfate were both found to mimic the biological specificities of heparan sulfate and heparin when forming the bioconjugates.

We prepared herein sulfated alginate and hyaluronan with different sulfation degrees and showed, by SPR technology, the interaction of the alginate sulfate and hyaluronan sulfate with various bioactive polypeptides. We determined that various positively-charged proteins and heparin-binding proteins bound specifically to the sulfated alginates and the sulfated hyaluronans with particular affinity-binding constants. Said proteins bound alginate sulfate and hyaluronan sulfate with high affinity and some of them exhibited superior binding to alginate sulfate and hyaluronan sulfate than to heparin (see, for example, bFGF, SDF-1, TGFβ1, and PDGF-BB binding in Table 3 hereinafter). We found that the pattern and kinetics of release of positively-charged proteins and heparin-binding proteins from these bioconjugates are dependent on the relative affinity of said proteins to the sulfated polysaccharide.

We have characterized the bioconjugates of the invention by different spectral and microscopic techniques and show herein that they create nanoparticles. We found that the sulfated alginate is a random coil polymer and, after interaction with the peptide growth factors, nanoparticles with about 53 nm diameter are obtained. This is important since it may provide protection for the peptide growth factor.

Thus, the invention further provides pharmaceutical compositions comprising nanoparticles of a bioconjugate comprising sulfated alginate and a bioactive polypeptide capable of binding to sulfate group(s) of the sulfated alginate. In preferred embodiments, the bioactive polypeptide is a growth factor, preferably bFGF or VEGF.

A bioconjugate according to the present invention can be injected to any part of the human body and serve as a delivery system for said bioactive polypeptide(s). For example, we show herein that administration of a bioconjugate comprising sulfated alginate and bFGF or a mixture of the three angiogenic factors VEGF, TGFβ1 and PDGF-BB to animals, promoted sustained release of the factors and lead to superior vascularization and more mature blood vessels than when the same factors were administered with non-modified alginate.

The experiment with the three angiogenic factors demonstrate that the angiogenic factors work in a complementary and coordinated manner to form mature and high density blood vessels.

Thus, in another aspect, the invention provides a pharmaceutical composition comprising a bioconjugate according to the invention and a pharmaceutically acceptable carrier. In a preferred embodiment, the pharmaceutical composition is useful as a delivery system for sustained release of at least one bioactive polypeptide.

For its use as a delivery system for the sustained release of the bioactive polypeptide(s), the bioconjugate of the invention may be injected or implanted in a mammal, optionally in association with or provided in a supporting matrix. The bioconjugate can further be used as scaffold for cell transplantation and tissue engineering. In the examples below, we show the successful sustained release of bioactive peptides from the bioconjugate of the invention present in capsules or in scaffolds formed by alginate.

Thus, in a preferred embodiment of the invention, the pharmaceutical composition further comprises a supporting matrix.

The matrix may serve as support or as a carrier for the bioconjugate and may be made up of particles or porous materials. The matrix material may be flexible and amenable to be fixed in place preventing its migration to an unintended location. The polymer matrix materials can be either natural or synthetic and include, but are not limited to, synthetic polymers such as polyethylene glycol (polyethylene oxide), poly(vinyl alcohol), polylactic acid, polyglycolic acid, and polyhydroxybutyrate, or natural polymers like collagen, fibrin, and gelatin, or polysaccharides like chitosan and alginate.

The matrix material is preferably biodegradable. Thus, physical removal of the matrix material from patient's tissue following drug delivery is not necessary and there is no concern about effects of the residual matrix in the long term. Of advantage is the use of a matrix material which does not provoke a significant inflammatory or proliferative tissue response or which does not alter or interfere with the patient's natural defense systems and healing processes.

The matrix may be in any form appropriate to the mode of delivery, for example, hydrogel, beads, microspheres (microbeads), hydrogel microcapsules, sponges, scaffolds, foams, colloidal dispersions, suspensions, and the like. Thus, a sustained release dosage form based on bioconjugates of sulfated polysaccharides and bioactive peptides may be fashioned as liquids, meshes, sponges, fibers and hydrogels.

In certain embodiments of the invention, the supporting matrix is selected from a polysaccharide, a protein, an extracellular matrix component, a synthetic polymer or a mixture thereof.

In one preferred embodiment of the invention, the supporting matrix is a polysaccharide, preferably alginate hydrogel or hyaluronan hydrogel. Thus, in one preferred embodiment, the invention provides alginate/alginate sulfate scaffolds. In another preferred embodiment, the invention provides hyaluronan/hyaluronan sulfate scaffolds. The binding and release from the these scaffolds can be controlled by the degree of alginate sulfation and by the extent of alginate sulfate incorporation into the delivery system.

The term "pharmaceutically acceptable carrier" refers to a vehicle which delivers the active components to the intended target and which will not cause harm to humans or other recipient organisms. As used herein, "pharmaceutical" will be understood to encompass both human and veterinary pharmaceuticals. Useful carriers include, for example, water, acetone, ethanol, ethylene glycol, propylene glycol, butane-1,3-diol, isopropyl myristate, isopropyl palmitate, mineral oil and polymers composed of chemical substances like polyglycolic acid or polyhydroxybutyrate or natural polymers like collagen, fibrin or polysaccharides like chitosan and alginate. The carrier may be in any form appropriate to the mode of delivery, for example, solutions, colloidal dispersions, emulsions (oil-in-water or water-in-oil), suspensions, creams, lotions, gels, foams, mousses, sprays and the like. Methodology and components for formulation of pharmaceutical compositions are well known and can be found, for example, in Remington's Pharmaceutical Sciences, Eighteenth Edition, A. R. Gennaro, Ed., Mack Publishing Co. Easton Pa., 1990.

In one embodiment of the invention, the carrier is an aqueous buffer. In another embodiment, the carrier is a polysaccharide and is preferably alginate hydrogel or hyaluronic acid.

The composition of the invention can be administered in a variety of ways. The routes of administration include, but are not limited to, intraliver, intradermal, transdermal (e.g. in slow release formulations), intramuscular, intraperitoneal, intravenous, intracoronary, subcutaneous, oral, epidural, topical, and intranasal routes. Any other therapeutically efficacious route of administration can be used.

In a further aspect, the invention provides a method for the sustained released administration of at least one bioactive polypeptide which is capable of binding a sulfate group of a sulfated polysaccharide to a patient in need of treatment with said at least one bioactive polypeptide, wherein the method comprises administering to a patient in need thereof an effective amount of a bioconjugate of the invention comprising a sulfated polysaccharide and said at least one bioactive polypeptide.

The delivery system of the present invention offers several advantages: (i) the release pattern and rate of the biactive polypeptide are dependent on the affinity binding constant and can be controlled; (ii) relatively long-term degradability-sustained release of therapeutically relevant molecules; (iii) formulation of the delivery system is an all aqueous method; (iv) the material is cheap in comparison to heparan sulfate or heparin; (v) the bioconjugates form nanoparticles; and (vi) the delivery system can be presented in the form of hydrogel microspheres (microbeads), hydrogel microcapsules, sponges, foams and injectable biomaterials.

Cochran et al., 2003, studied the binding interactions of the phosphosulfo-mannan anticancer agent PI-88 and derivatives thereof with the angiogenic growth factors FGF-1, FGF-2 and VEGF. PI-88 is a mixture of highly sulfated, monophosphorylated mannose oligosaccharides ranging in size from di- to hexasaccharide. The derivatives of the PI-88 which were studied had defined carbohydrate chain length (2 to 5 saccharide units) and lacked a phosphate group. The results obtained in this binding study indicated that the two dominant components of the PI-88 mixture, namely, the penta- and tetrasaccharide components, have increased affinity for the angiogenic factors and therefore are responsible for the bulk of the antiangiogenic activity of PI-88. The binding studies demonstrated that PI-88 had greater affinity for FGF-1 and VEGF than heparin, heparan sulfate or polyanionic drugs such as sucrose octasulfate. The binding was highly dependent on the degree of sulfation and the chain length tested.

Alginate and hyaluronan are polysaccharides and not short oligosaccharide as PI-88, and are of different composition than PI-88. It was thus unexpected that their sulfated form would exhibit high affinity for angiogenic factors and in general for heparin-binding polypeptides and/or positively-charged bioactive polypeptides. Moreover, we found that alginate sulfate and hyaluronan bound bFGF, SDF-1, TGFβ1, and PDGF-BB with higher affinity than heparin (Tables 3 and 6).

In view of the high affinity of alginate sulfate and hyaluronan sulfate to the bioactive polypeptides capable of binding sulfated polysaccharides, said sulfated polysaccharides themselves may be exploited for the elimination of said bioactive polypeptides in diseases or disorders caused by or associated with the activity of said bioactive polypeptides. For example, alginate sulfate or sulfated hyaluronan can be used for the treatment of: cancer which is known to be associated with growth factors and angiogenic factors; inflammatory diseases such as rheumatoid arthritis and bowel inflammatory diseases (e.g. Crohn's disease) associated with IL-6 activity; proliferative diabetic retinopathy associated with VEGF activity; myelodysplastic syndrome with myelofibrosis associated with TGFb and TPO activity; diabetic peripheral neuropathy associated with IFG activity; pulmonary arterial hypertension associated with PDGF-BB activity; and arteriosclerosis associated with PDGF-AA activity.

Thus, in another aspect, the invention provides a pharmaceutical composition comprising a sulfated polysaccharide selected from sulfated alginate and/or sulfated hyaluronan and a pharmaceutically acceptable carrier, for treatment or inhibition of a disease or disorder caused by, or associated with, the activity of at least one bioactive polypeptide capable of binding a sulfate group of said sulfated polysaccharide. For example, the composition can be useful for treatment of diseases or disorders caused by, or associated with, the activity of a bioactive polypeptide selected from PDGF-BB, bFGF, VEGF, TGFβ, aFGF, IL-6, TPO, SDF-1, HGF, EGF, IGF, PDGF-AA, and a combination thereof.

In a preferred embodiment, the invention provides a pharmaceutical composition comprising a sulfated alginate and/or sulfated hyaluronan and a pharmaceutically acceptable carrier for the treatment of cancer.

In another aspect, the invention relates to a method for treatment of a patient suffering from a disease or disorder caused by, or associated with, the activity of at least one bioactive polypeptide capable of binding a sulfate group of a sulfated polysaccharide, which comprises administering to said patient an effective amount of a sulfated alginate, sulfated hyaluronan, or both.

In a preferred embodiment, the invention relates to a method for the treatment of a patient suffering from cancer.

The invention will now be described with reference to some non-limiting examples.

EXAMPLES

Example 1

Method of Alginate Sulfation and Product Analysis

To confer specificity on the alginate for its use as a delivery system, we developed the bioconjugate concept of alginate sulfate. The properties of alginate sulfate such as biocompatibility, hydrophilicity, and the simple method of its formulation (physical cross-linking) as well as its low cost (of production and sulfation) are advantageous to its application for the controlled delivery of cytokines, growth factors and heparin-binding polypeptides, as well as a scaffold for tissue engineering.

1(i). Preparation of Alginate Sulfate

Alginate sulfation was conducted by the sulfuric acid/carbodiimide method for sulfation of uronic acid-containing polysaccharides, essentially as described in U.S. Pat. No. 6,388,060, hereby incorporated by reference in its entirety as if fully described herein. In brief, the reaction is comprised of two steps: first, converting sodium alginate to alginic acid by batch ion exchange and then titration with an amine such as a tertiary amine, for example, tributylamine (TBA), yielding alginate-TBA. The second step consists of O-sulfating the amine salt of alginate by treatment with sulfuric acid and addition of a N,N'-carbodiimide, e.g., N,N'-dicyclohexylcarbodiimide (DCC), with various molar ratios of the components: DCC: $H_2SO_4$: uronic acid. The degree of alginate sulfation was evaluated by Fourier-Transformed Infrared Spectroscopy (FTIR) and microanalysis.

Table 1 summarizes the different component molar ratios used for alginate sulfation and the resulting degree of alginate sulfation.

TABLE 1

Sulfation of alginate

| Uronic acid:DCC:$H_2SO_4$ (Molar Ratio) | Sulfation Degree (Uronic Acid:Sulfor) |
|---|---|
| 1:20:30 | 1:0.8 |
| 1:10:20 | 1:0.4 |
| 1:20:20 | 1:0.6 |

1(ii) Determination of Sulfation Degree

The sulfated alginate product was characterized by FTIR. Homogeneous pellets of the lyophilized product (0.0035 g) with potassium bromide (0.100 g; Fluka, Switzerland) were prepared by applying pressure (4.5 metric tons, Carver, Inc., Wabash, India).

Quantitative microanalysis was conducted for estimation of the ester sulfate content within the alginate sulfate product after its acid hydrolysis (Dodgson and Price, 1962). The liberated inorganic sulfur was estimated turbidimetrically as insoluble barium sulfate, at wavelength 360 nm, using a spectrophotometer and its amount was interpolated from a calibration curve for known concentrations of $K_2SO_4$.

1(iii) FTIR Analysis

Alginate sulfate was characterized by FTIR to reveal the changes in product versus the raw material, sodium alginate. The IR spectrum of alginate sulfate shows a new major peak at ~1250 $cm^{-1}$ and a minor peak at ~800 $cm^{-1}$ (FIG. 1). The peak at ~1250 $cm^{-1}$ is assigned to S=O symmetric stretching, while the one at ~800 $cm^{-1}$ for S—O—C stretching. The degree of sulfation on sodium alginate was determined by analyzing the area under the peak (1325-1186 $cm^{-1}$).

Example 2

Biomolecular Interactions of Alginate Sulfate and Heparin-binding Polypeptides by SPR Technology Real-time biomolecular interaction analysis was performed using the BIAcore 3000 instrument (Pharmacia Biosensor AB, Sweden), operated with BIA evaluation version 3.2 software. All experiments were performed at 25° C., using HBS (10 mM HEPES, 0.15M NaCl, 3 mM EDTA, 0.005% surfactant P20, pH 7.4) as a running and dilution buffer.

2(i) Immobilization of the Ligands to Sensor Chip

The different polysaccharide samples were immobilized onto the sensor chip via biotin-avidin chemistry. Biotinylated sample of heparin-albumin was purchased (Sigma-Aldrich Chemicals, St Lewis, Mich.) and biotinylated samples of alginate and alginate sulfate were prepared using the method described in Polyak et al (2004). The biotinylated samples of the polysaccharides were immobilized onto streptavidin sensor chip (SA, Pharmacia Biosensor AB) as follows: the sensor chip was pulsed three times with 1 min-injections of 50 mM NaOH, 1M NaCl at flow rate of 10 μl/min, to remove non-covalently bound streptavidin from the sensor surface. Flow-cell 1 (FC-1) remained with no immobilized ligand for reduction of non-specific interactions of the analyte with the sensor chip SA. The positive control, biotinylated heparin-albumin (10 μg/ml in HBS buffer) was injected to FC-2 for 1 min, at a flow rate of 10 μl/min, to achieve covalent immobilization of 300 RU (resonance units) on the biosensor surface. In FC-3, a similar amount of biotinylated alginate sulfate (10 μg/ml in HBS buffer) was immobilized to the surface. The injection was stopped after 5 μl after achieving RU similar to the positive control. In FC-4, immobilization of the negative control, biotinylated alginate, was done in the same way.

2(ii) Binding of Heparin-binding Polypeptides

Binding assays were performed over a range of polypeptide concentrations (Table 2) (in increments of 100 nM). The protein was diluted with HBS buffer immediately prior to injection (flow rate of 20 μl/min, 4 min, dissociation time was 3 min). The sensor chip was regenerated by injections of NaCl (1M, 1 min, 20 μl/min).

2(iii) Data Analysis

The real-time reference curve obtained from a nonligand coated flowcell exposed to HBS buffer (FC-1) was subtracted from binding curves obtained from the flowcells with immobilized ligands. Association and dissociation rate constants were calculated by nonlinear curve fitting of the primary sensorgram data using the (Langmuir) binding model available in the BIAevaluation 3.1 software (Biacore). The affinity constants (K) were calculated from the association and dissociation rate constants using the software.

TABLE 2

Peptide type and concentration range in SPR studies

| # | Peptide | Peptide (abbreviated) | Concentration Range (nM) |
|---|---------|----------------------|--------------------------|
| 1 | Platelet-derived growth factor BB | PDGF-BB | 50-300 |
| 2 | Basic fibroblast growth factor | bFGF | 200-600 |
| 3 | Vascular endothelial growth factor | VEGF | 500-5000 |
| 4 | Transforming growth factor β1 | TGFβ1 | 80-300 |
| 5 | Acidic fibroblast growth factor | aFGF | 10-50 |
| 6 | Interleukin 6 | IL-6 | 100-1400 |
| 7 | Thrombopoietin | TPO | 200-1000 |
| 8 | Stromal Cell Derived Factor-1 | SDF-1 | 100-600 |
| 9 | Hepatocyte growth factor | HGF | 50-250 |
| 10 | Epidermal growth factor | EGF | 500-5000 |
| 11 | Insulin growth factor | IGF | 5000-25000 |
| 12 | Platelet-derived growth factor AA | PDGF-AA | 450-700 |
| 13 | FLT | FLT-3 | No specific binding to alginate sulfate |
| 14 | Stem cell factor | SCF | No specific binding to alginate sulfate |
| 15 | Oncostatin | OCM | No specific binding to alginate sulfate |

Of the molecules studied in Table 2, peptides 1-12, which are known to be heparin-binding peptides according to published literature, showed specific binding to alginate sulfate, while no such interactions were observed with non-modified alginate (FIGS. 2A-13A). The SPR sensorgrams (FIGS. 2B-12B) for peptide binding to alginate sulfate, over a range of peptide concentrations (Table 2), showed that the interactions fit the Langmuir 1:1 binding model, with the equilibrium binding constants detailed in Table 3.

The specificity of interactions can also be seen in the finding that peptides, which do not belong to the heparin-binding peptides class (peptides 13-15 in Table 2) did not interact with alginate sulfate or with heparin.

Sulfation of unsulfated uronic acid-containing alginates converted these polysaccharides into a biologically active species. The monomer β-D-mannuronic acid in alginate differs from the uronic acid in heparan sulfate (HS) at positions C2 or C3, in which positions heparan sulfate has sulfate groups while mannuronic acid has hydroxyl groups. This structure similarity has lead us to the hypothesis that alginate sulfate may substitute HS in terms of its interactions with heparin-binding growth factors such as bFGF. The heparin-binding peptides interact with heparin or heparan sulfate via regions containing 2-O-sulfated L-iduronic acid [IdoA (-2-$SO_3$)] and N-sulfated glucosamine ($GlcNSO_3$) residues, wherein the sulfate groups play central role in binding.

Table 3 below depicts binding of different peptides to alginate sulfate compared to heparin and shows data obtained according to the present invention or disclosed in the literature.

TABLE 3

Binding to Alginate Sulfate compared to Heparin (this work and literature)

| | Peptide | Ligand | $K_A$ ($M^{-1}$) | $K_D$ (M) | $X^2$ | $K_D$ (M) (Literature) |
|---|---------|--------|------------------|-----------|-------|------------------------|
| 1 | PDGF-BB | Heparin | $1.33*10^6$ | $7.51*10^{-7}$ | 10.1 | — |
| | | Alginate-sulfate | $35.3*10^6$ | $0.28*10^{-7}$ | 9.09 | |
| 2 | bFGF | Heparin | $1.7*10^7$ | $6.0*10^{-8}$ | 19.9 | $7.13*10^{-8}$ (Xiao-feng, Ya-xiang et al. 2003) |
| | | Alginate-sulfate | $9-20*10^7$ | $0.5-1.11*10^{-8}$ | 17.1 | |
| 3 | VEGF | Heparin | $9.68*10^7$ | $1.03*10^{-8}$ | 15.8 | $~2*10^{-8}$ (Cochran et al, 2003) |
| | | Alginate-sulfate | $2.2-3.2*10^7$ | $3.2-4.5*10^{-8}$ | 11.4 | |
| 4 | TGFβ1 | Heparin | $2.38*10^7$ | $4.2*10^{-8}$ | 13.9 | — |
| | | Alginate-sulfate | $2.31*10^{12}$ | $7.32*10^{-13}$ | 8.03 | |

TABLE 3-continued

Binding to Alginate Sulfate compared to Heparin (this work and literature)

| | Peptide | Ligand | $K_A$ ($M^{-1}$) | $K_D$ (M) | $X^2$ | $K_D$ (M) (Literature) |
|---|---|---|---|---|---|---|
| 5 | aFGF | Heparin | $7.9*10^7$ | $1.26*10^{-8}$ | 9.66 | $18 \pm 3.0*10^{-8}$ (Kamei, Wu et al. 2001) $16.0*10^{-8}$ (Zhang, Fath et al. 2002) |
| | | Alginate-sulfate | $2.8*10^7$ | $3.59*10^{-8}$ | 5.84 | |
| 6 | IL-6 | Heparin | $1.12*10^7$ | $8.91*10^{-8}$ | 6.86 | — |
| | | Alginate-sulfate | $1.38*10^7$ | $7.27*10^{-8}$ | 5.32 | |
| 7 | TPO | Heparin | — | — | — | — |
| | | Alginate-sulfate | $1.81*10^6$ | $5.53*10^{-7}$ | 0.679 | |
| 8 | SDF-1 | Heparin | $1.65*10^7$ | $6.06*10^{-8}$ | 11.9 | $3.84*10^{-8}$ (Amara, Lorthioir et al. 1999) |
| | | Alginate-sulfate | $20.6*10^7$ | $0.485*10^{-8}$ | 12.7 | |
| 9 | HGF | Heparin | $1.19*10^8$ | $8.42*10^{-9}$ | 4.64 | $1.00*10^{-9}$ (Rahmoune, Rudland et al. 1998) |
| | | Alginate-sulfate | $0.536*10^8$ | $18.7*10^{-9}$ | 1.88 | |
| 10 | EGF | Heparin | $8.38*10^6$ | $1.19*10^{-7}$ | 0.794 | — |
| | | Alginate-sulfate | $9.93*10^6$ | $1.01*10^{-7}$ | 0.354 | |
| 11 | IGF | Alginate-sulfate | $1.01*10^8$ | $1*10^{-8}$ | 0.86 | |
| 12 | PDGF-AA | Alginate-sulfate | $2.35*10^{11}$ | $4.26*10^{-12}$ | 25 | |

Example 3

Sustained Release from Alginate/Alginate Sulfate Capsules

This example examines the capability of alginate sulfate to sustain the release of the angiogenic heparin-binding peptide, bFGF, from microspheres compared to microspheres composed of only unmodified alginate.

3(i) Microsphere Preparation and bFGF Encapsulation

Sodium alginate (high G content, FMC Biopolymers) solution 1% (w/v DDW) was mixed in different volume proportions with alginate sulfate solution 1% (w/v DDW). bFGF (0, 0.2, 0.5, 1, 2 µg/ml) was added to alginate/alginate sulfate mixture, and incubated for 1 h, 37° C. The mixture was collected into a syringe (18G) and was dropped into stirred $CaCl_2$ solution (10-12 ml, 0.15M). The capsules were allowed to stir at room temperature for 0.5 h until gelation is complete and centrifuged (1500 RPM, 25° C., 10 min). The supernatant was removed and a sample (1 ml) from the capsules containing bFGF was suspended in 1 ml culture medium (CM) DMEM (1% Pen-Strep Biological Industries, Israel). Release studies were conducted by incubating the capsules on a rotating incubator at 37° C. The CM was semi-replaced daily (0.5 ml) and the amount of bFGF in releasing media was determined by ELISA. All the experiments were performed in a sterile environment.

3(ii) Analysis of Released bFGF by ELISA

Samples from releasing medium were diluted 1:10 with PBS buffer (pH=7.4, NaCl 137 mM, $Na_2HPO_4$ 8 mM, KCl 2.7 mM, $KH_2PO_4$ 1.5 mM, Sigma) and placed (100 µl/well) in 96-well polyvinylchloride (PVC) plate overnight, at 4° C. After washing twice with 300 µl/well PBST (PBS buffer, pH 7.4, 0.05% Tween 20), residual protein-binding sites in the wells were saturated by incubating with 250 µl/well of blocking solution (PBS, 2% BSA), either at 4° C. overnight or for 2 h at 37° C. (shaking). After three washes with PBST (300 µl/well), 100 µl of the growth factor-specific detection antibody (2 µg/ml goat polyclonal anti-bFGF in PBS, 1% BSA, R&D systems Inc.), was allowed to incubate in the wells for 1 h, at 37° C. (shaking). After another round of washing (PBST 300 µl/well X8), 100 µl of streptavidin-horseradish peroxidase (HRP) conjugated (1 µg/ml PBS 1% BSA, Chemicon International) was added and incubated for 1 h at room temperature in dark. Wells were then washed and bound HRP was detected by addition of 100 µl of 3,3',5,5'-tetramethylbenzidine (TMB; Chemicon International) as a peroxidase substrate. The reaction was stopped after 5 min by addition of 50 µl 0.5M $H_2SO_4$. The absorbance of the yellow reaction product was then measured at 450 nM on a plate reader (Bio-Tek Instruments, EL808). Standard bFGF solutions (6.25, 3.125, 1.56, 0.8, 0 ng/ml) were used for calibration.

In this example, the study rationale was to verify whether capsules containing alginate sulfate can sustain bFGF release and presentation. Two initial studies were performed to optimize the amounts of alginate sulfate and bFGF within the capsules. In the first, the amount of alginate sulfate in alginate/alginate sulfate solution was maintained constant (0.9%/0.1%, w/v, respectively) while bFGF concentrations were varied (0, 0.2, 0.5, 1, 2 µg/ml of alginate/alginate sulfate solution). The polymer mixture solution and the bFGF solution were incubated at 37° C., 1 h, for binding before capsulation. During release study, the capsules were incubated in 1 ml culture medium for 5 days at 37° C. and the medium was partially (0.5 ml) replaced daily with a fresh one. The collected medium with the liberated bFGF was analyzed by ELISA. The results in FIG. 14 are presented as accumulated OD vs. time. As seen, the release rate is fairly constant and proportional to bFGF concentrations initially encapsulated in the capsules. The second study was aimed at optimizing the amount of lginate sulfate added (0, 0.1, 0.5, 0.75, 1% w/v) into the mixture alginate/alginate sulfate with excess of bFGF (2 µg/ml). After binding and capsule formation, release studies were performed. We found that a 0/1 (% wt ratio) mixture of alginate/alginate sulfate did not form stable capsules in the presence of $CaCl_2$, while the other mixtures did form. The samples were analyzed by ELISA and the results are presented as accumulated OD (FIG. 15). It is shown that alginate sulfate in the capsules sustained bFGF release to the medium. As the amount of alginate sulfate in the capsules increased, less bFGF was released. to the external medium.

Based on these studies, an optimal formulation was developed. It consisted of a mixture of alginate/alginate sulfate (9:1 wt ratio) at a final polymer concentration of 1% (w/v), and incorporated 0.2 µg/ml bFGF. bFGF release from three batches of such capsules was evaluated over a 6-day period. Control capsules were made of only sodium alginate (LF-120, Nova Matrix, high G) 1% (w/v) and adsorbed bFGF (0.2 µg/ml). The formulations were incubated as described above and the released bFGF was analyzed by ELISA. bFGF content was interpolated from a calibration curve of known bFGF concentrations. The results are presented as accumulated bFGF concentrations in medium (FIG. 16).

The release rate of bFGF from the alginate/alginate sulfate composite capsules was fairly constant, after an initial burst of 30%, showing a nearly linear release pattern. Faster release rates were seen from the capsules with no alginate sulfate. By day 6, approx 90% of the encapsulated growth factor in control capsules was released to the external medium, while in the composite alginate sulfate containing capsules approximately 70% release was seen.

Example 4

Release of Multiple Angiogenic Factors

We tested the capability of the alginate sulfate-based delivery system to co-encapsulate 4 important angiogenic factors and release them at a sustained manner, depending on their $K_A$ equilibrium binding to alginate sulfate and the initial concentration of encapsulated peptide. The four factors included VEGF, bFGF, aFGF and PDGF-BB, which are responsible for inducing blood vessel formation and maturation. The concentration of free peptide (correlates to released peptide) was calculated according to the following equation (derived from the equilibrium binding equation assuming that alginate concentration is well above that of the peptide, so that total alginate concentration is considered equal to that of free one):

$$[GF]_{free} = \frac{[GF]_{Total}}{(1 + K_A \cdot [AlgSO_3]_{Total})}$$

The results shown herein in FIG. 17 reveal that VEGF is released at a faster rate compared with PDGF-BB. Such pattern will be suitable for blood vessel growth and maturation. At earlier stages of blood formation, the presence of VEGF is necessary for forming the vessel, and later, PDGF-BB stabilizes the vessels by recruiting mural cells.

Example 5

In-vivo Angiogenesis and Scaffold Vascularization

In this example, we show that the novel alginate/alginate sulfate system is capable of sustaining the release and presentation of the heparin-binding peptides also in vivo. For a proof of concept, we tested this system for the sustained delivery of a single angiogenic factor (bFGF) and for the co-delivery of multiple angiogenic factors (VEGF, PDGF-BB and TGF-β). We compared the kinetics and extent of in vivo angiogenesis compared with peptides delivered from non-modified alginate systems (through instant release).

To enable a simple determination of blood vessels in the in vivo set up, the delivery systems were fabricated as macroporous (~100 µm pore size) scaffolds, which enable blood vessel penetration without obstructions. Another advantage of the scaffold system is its potential application for tissue engineering and regeneration.

5(i) Preparation of Porous Scaffolds and Characterization

Alginate/alginate sulfate scaffolds, diameter 11 mm, thickness 3 mm, were prepared from a mixture of alginate with high guluronic acid (G) content (>65% G; FMC Biopolymers) and alginate sulfate (9:1 wt ratio) by freeze-dry technique as previously described (Shapiro and Cohen, 1997). In brief, alginate and alginate sulfate were dissolved separately in DDW to obtain 1.25% (w/v) solutions. Sterilization of sodium alginate was achieved by filtration through 0.2 µm filter under $N_2$ pressure. Cross-linking was achieved by adding D-gluconic acid hemi-calcium ion solution (1% w/v, Sigma, Israel) to the mixture while being homogenized (26,000 rpm, DIAX 900 Heidolph, Germany). The mixtures were pulled into 48-well plates (250 µl/well), chilled to 2°-8° C. over night, frozen at −20° C. for 24 h and then lyophilized. Scaffolds sterilization was achieved by ethylene oxide or with ultraviolet (UV) light (1 h, 25° C.).

FIG. 18 shows a picture of the alginate/alginate sulfate scaffold and its SEM (scanning electron microscope) morphology. When compared to a scaffold made of non-modified alginate, there is no measurable difference in morphology.

5(ii) Feasibility Studies with Basic FGF Incorporated into Alginate/Alginate Sulfate Composite Scaffolds (Single Peptide System).

Composite scaffolds of alginate/alginate sulfate (9:1, wt ratio, total of 1% w/t solution) were implanted subcutaneously in the dorsal area in Sprague Dawley (SD) rats, two scaffolds in each rat. Prior to implantation, the scaffolds were incubated for 1 h, at 37° C., in 80 µl culture medium with or without bFGF. Additional control group was implanted with alginate scaffolds incorporating bFGF by adsorption (Table 4).

TABLE 4

Experimental and control groups in the study

| Group | Scaffold type | bFGF (µg/scaffold) | n |
|---|---|---|---|
| Study | alginate/alginate sulfate | 10 | 4 |
| Control I | Alginate | 10 | 4 |
| Control II | alginate/alginate sulfate | 0 | 2 |

At day 14 post-implantation, the rats were sacrificed and the implanted scaffolds and surrounding tissues were removed together, fixed in formalin, paraffin embedded, sectioned and stained with hematoxylin and eosin (H&E). In the study group implanted with bFGF-composite scaffolds, the implants were surrounded by a large capsule. All capsules were thick and full with serotic blood liquid, with no sign of infection (FIG. 19). In both the control groups I and II, no capsules were found. In control group I, implanted with alginate scaffolds with adsorbed bFGF, disassembled scaffolds were found attached to the subcutaneous tissue with no sign of infection. In control group II, implanted with alginate/alginate sulfate with no bFGF, whole scaffolds were found with no sign of infection as well.

Lower magnification pictures of cross-sections in the implant, stained with H&E, are shown on the right side of FIG. 19. Cross-sections in the bFGF incorporating alginate/alginate sulfate composite scaffolds (FIG. 19A) show a thick capsule surrounding the scaffold and significant tissue penetration into scaffold. Lesser extent of tissue penetration was found in alginate scaffold adsorbed with 10 µg bFGF (FIG. 19B). In alginate/alginate sulfate scaffolds, with no bFGF supplementation (FIG. 19C), tissue ingrowth was minimal. Higher magnification pictures (FIG. 20) show that the penetrating tissue is confined within the scaffold pore walls that were not degraded at this time point. In the control groups (I and II), most of the scaffold pores had no tissue.

Blood vessel density (number per mm$^2$) (FIG. 21) and the percentage area occupied by them (FIG. 22), were determined in 10 different fields/slide, randomly selected from H&E cross sections slides, using Scion image NIH software. The focus of analysis was on the capsule membrane surrounding the implants since our intention was to examine release outside the scaffold. Collectively, theses results show that controlled release of bFGF from alginate/alginate sulfate scaffolds enhanced scaffold vascularization. On day 14 post-implantation, 57.6±6.8 blood vessels/mm$^2$ were counted in bFGF-releasing scaffolds made of alginate/alginate sulfate, while only 28.2±13.2 and 15.1±8.8/mm$^2$ were found in the FGF-adsorbed alginate scaffolds and alginate sulfate (with no bFGF), respectively. The difference between the study/control I and study/control II group is significant (analysis of variance, ANOVA single factor, P<0.05) while the difference between the two control groups is not significant (P>0.05).

The percentage of area occupied by blood vessels was also analyzed on sections of the implanted scaffolds. This analysis takes into account the size of the blood vessels. FIG. 22 shows that the area occupied by blood vessels is 2.9 times larger in the bFGF-releasing alginate/alginate sulfate scaffolds than in groups implanted with bFGF-adsorbed alginate scaffolds and 8.3 times higher than similar scaffolds without bFGF supplementation. These results indicate that controlled bFGF delivery enhances scaffold vascularization.

The distribution of blood vessel size was also analyzed by measuring their median diameter, using Scion image NIH software. Due to variations in vessel shape, the smaller diameter assuming elliptic shape for the vessels was taken as a representative diameter. The blood vessels were divided randomly according to their size, into 9 groups: x<5, 10>x≧5, 15>x≧10, 10>x≧15, 25>x≧20, 30>x≧25, 40>x≧30, 50>x≧40, 100>x≧50 µm. FIG. 23 shows the diameter distribution of the newly formed blood vessels in the implanted scaffolds. Most of the blood vessels in all groups had diameter size of 5 to 20 µm. In the bFGF-releasing alginate/alginate sulfate scaffolds, blood vessels with larger diameters (>50 µm) were also found.

Next, the fibrotic capsule surrounding the scaffold was scanned, to evaluate differences between the different groups. The pictures presented in FIG. 24 revealed that the bFGF releasing alginate/alginate sulfate scaffolds were surrounded by a thick cellular capsule that was enriched with large blood vessels (FIG. 24 A, B). In the group implanted with bFGF-adsorbed to alginate scaffold, the surrounding capsule was thinner (FIGS. 24 C, D) and in those implanted with alginate/alginate sulfate scaffolds, but no bFGF, the capsule was minimal (FIGS. 24 E, F). As seen, there is an effect of bFGF on angiogenesis; however, this effect is magnified by the controlled delivery of the growth factor over time.

We further performed immunohistochemistry, examining the maturity state of the blood vessel (staining for isolectin and smooth muscle actin). In addition, we stained for the marker ED-1, which is expressed on macrophages (FIG. 25).

FIG. 25 shows high magnification pictures of immunostained cross-sections in the implant, 14 days after implantation. The presence of smooth muscle cells indicates the maturation of the formed blood vessels [blood vessels are composed of three main layers: an internal layer, called tunica intima, composed of endothelium that lines the lumen of all vessels; a middle layer, called tunica media, composed of smooth muscles cells and elastic fibers; and an external layer, called tunica adventitia, comprising collagen fibers]. FIGS. 25A-C1 show positive staining for smooth muscle actin (αSMA), indicating the presence of smooth muscle cells that are surrounding the newly formed blood vessels and their maturation. Most of the blood vessels in the capsule of the alginate/alginate sulfate/bFGF group (A1) are surrounded by smooth muscle cells, while those in the control groups are less stained, showing much less angiogenesis and matured blood vessels. Endothelial cells are stained with anti-lectin α-lectin) (FIGS. 25A-C2). Staining with α-lectin marks the formed blood vessels surrounding the implant. ED1 staining of the macrophages suggests host immune reaction to the implant (FIGS. 25A-C3), probably as part of a wound healing process. The staining is minimal for the scaffold with no bFGF, while it is intense in the group wherein bFGF is adsorbed to the alginate scaffold and thus is released rapidly. Thus, the presence of large amount of bFGF at implant site, at a given time point, causes increased inflammation, while sustained delivery of bFGF over time diminishes this effect.

Example 6

Multiple Angiogenic Factor System Based on Alginate/Alginate Sulfate Composite Scaffolds Composite scaffolds of alginate/alginate sulfate (9:1, wt ratio, total of 1% w/t solution) were implanted subcutaneously in the dorsal area in SD rats, two scaffolds in each rat. Prior to implantation, the scaffolds were incubated for 1 h, at 37° C., in 80 µl culture medium with a single factor bFGF or a mixture of angiogenic growth factors (according to Table 5). Two control groups were implanted with alginate scaffolds incorporating bFGF or the mixture of the factors by adsorption (Table 5). Additional control group consisted of implanting the alginate/alginate sulfate scaffold, with no growth factor.

TABLE 5

Experimental and control groups in the study

| Group | Scaffold type | Angiogenic Factor (total of 100 ng/scaffold) | n |
|---|---|---|---|
| Study I | alginate/alginate sulfate | bFGF | 6 |
| Study II | alginate/alginate sulfate | VEGF, PDGF-BB, TGF-β 0.6:1:1 molar ratio | 6 |
| Control I | Alginate | bFGF | 6 |
| Control II | Alginate | VEGF, PDGF-BB, TGF-β 0.6:1:1 molar ratio | 6 |
| Control III | alginate/alginate sulfate | 0 | 6 |

At 1 and 3 months post-implantation, the rats were sacrificed and the implanted scaffolds and surrounding tissues were removed together, fixed in formalin, paraffin embedded, sectioned and stained with Hematoxylin and Eosin (H&E) or immunostained for lectin (L-3759, Sigma, Germany). Blood vessel density (number per mm$^2$) (FIG. 26) and the percentage area occupied by them (FIG. 27) were determined from different fields in each slide, randomly selected from the lectin-immunostained cross-sections slides, using Scion Image NIH software. Collectively, theses results show that sustained delivery of growth factors from alginate/alginate sulfate scaffolds enhanced angiogenesis at the implant site. One month post-implantation, 115.52±32.52 blood vessels/mm$^2$ was counted in the capsules surrounding the implants of bFGF-bound alginate/alginate sulfate scaffolds. The density of the blood vessels is twice the number found in Experiment #1 (in vivo), although it should be reminded that the amount of bFGF used in Experiment #2 is 100-fold less (0.1 vs 10

μg/scaffold). Blood vessel density was less, 75.40±12.44 blood vessels/mm² in the group implanted with VEGF/PDGF-BB/TGFβ1 bound alginate/alginate sulfate scaffolds. Vessel density was less in the groups wherein the growth factors were adsorbed to the matrix (and not bound). As shown also in FIG. 26, vessel density was maintained for at least 3 months. According to the percentage area occupied by the blood vessels in cross section (FIG. 27), it is seen that the group receiving the multiple angiogenic factors bound to alginate sulfate, had significant larger blood vessels and most of the vessels were mature (d>20 mm) (FIG. 28). FIGS. 29-30 show immunostaining for lectin and SMA. The positive response indicates the presence of mature blood vessels encased by smooth muscle cells.

Example 6

Sulfation of Hyaluronan (Hyaluronic Acid) and Bioconjugation with Bioactive Peptides Hyaluronan (HA), the only non-sulfated glycosaminoglycan (GAG) and a major component of ECM (extracellular matrix), was sulfated in order to convert it into a reactive polymer capable of specifically interacting and releasing positively-charged peptides (polypeptides, proteins) and heparin-binding peptides, to form a bioconjugate.

For this purpose, we used relatively low molecular HA fragments that have reduced viscosity in solution, thus enabling a better manipulation with the polymer modification as well as better homogeneity in the results. The fragments obtained were characterized by Gel Permeation Chromatography (GPC). Next, we proceeded to sulfation of HA low MW fragments and characterization of degree of sulfation by FTIR (as described above for alginate sulfation). The interaction of HA sulfate and heparin-binding peptides was characterized by SPR technology using the BIAcore 3000 instrument as described above for heparan sulfate. For characterization of the bioconjugates of HA-sulfate and bioactive proteins by SPR, biotinylated HA and biotinylated HA-sulfate immobilized onto streptavidin sensor chip were used.

6(i) Obtaining Low Molecular HA Fragments by Heating

Three glass vessels (100 ml Erlenmeyer flasks) containing hyaluronan (1% w/v, 10 ml, Sigma, Cat#53747) were heated at 121° C. for 30', 60 and 90'. Molecular weight (Mw) and number-average molecular mass (Mn) analysis and polydispersity (PDC) were performed by GPC. The results are shown in Table 6,

TABLE 6

Molecular weight, molecular mass and and polydispersity

| Treatment | Mw (Dalton) | Mn (Dalton) | PDC (Mw/Mn) |
| --- | --- | --- | --- |
| No treatment | $8.612 \times 10^5$ | $8.366 \times 10^5$ | $1.029 \pm 0.005$ |
| 30', 121° C. | $3.403 \times 10^5$ | $3.203 \times 10^5$ | $1.063 \pm 0.003$ |
| 60', 121° C. | $2.019 \times 10^5$ | $1.860 \times 10^5$ | $1.086 \pm 0.003$ |
| 90' 121° C. | $1.202 \times 10^5$ | $1.099 \times 10^5$ | $1.094 \pm 0.003$ |

Further experiments were carried out with the 120 kDa HA fragments (data not shown).

6(ii) Sulfation of HA Low Mw Fragments and Characterization by FTIR

HA sulfation was conducted by the sulfuric acid/carbodiimide method, essentially as described in US patent U.S. Pat. No. 6,388,060 (as described in Example 1).

HA-sulfate was characterized by FTIR versus the raw material, low MW HA. The IR spectrum of sulfated HA (FIG. 31) shows a new major peak at ~1250 cm$^{-1}$, which is assigned to S=O symmetric stretching, whiles the one at ~800 cm$^{-1}$ for S—O—C stretching.

For the SPR characterization of the bioconjugates, sulfated and unsulfated HA were biotinylated as described for alginate (as described in Example 2).

Table 6 summarizes the results obtained in SPR sensorgrams (FIGS. 32 and 33) of peptide binding to sulfated HA, over a range of peptide concentrations. The results show specific binding of sulfated HA to bFGF and sulfated HA to VEGF, while no interactions were found with the nonmodified HA. The SPR sensorgrams (FIG. 32B-33B) of peptide binding to HA-sulfate, over a range of peptide concentrations showed that the interactions fit the Langmuir 1:1 binding model, with equilibrium binding constants as detailed in Table 6. We found that the binding of VEGF and bFGF to sulfated HA was stronger than their binding to heparin.

TABLE 7

Bioconjugate Formation. Characterization by SPR

| | Peptide | Ligand | $K_A$ (M$^{-1}$) | $K_D$ (M) | $X^2$ | KD (M) (Literature) |
| --- | --- | --- | --- | --- | --- | --- |
| 1 | BFGF | Heparin | $1.34*10^7$ | $7.46*10^{-8}$ | 87.4 | $7.13*10^{-8}$ (Xiao-Feng, Ya-xiang et al., 2003) |
| | | Ha sulfate | $1.36*10^8$ | $7.33*10^{-9}$ | 76.5 | |
| 2 | VEGF | Heparin | $9.68*10^7$ | $1.03*10^{-8}$ | 15.8 | |
| | | Ha sulfate | $2.11*10^8$ | $4.47*10^{-9}$ | 23.4 | |

Example 7

Characterization of the Particles of the Bioconjugates

In this example, we characterize the physical nature of the bioconjugate of alginate sulfate and the bioactive peptide using spectral and microscopic methods.

The methods used herein were as follows:

Atomic Force Microscope (AFM) Analysis. Alginate sulfate (5 kDa) was dissolved in HEPES buffer (HEPES, 1 mM containing NiCl$_2$ 10 mM). VEGF or bFGF aqueous solutions were mixed with alginate sulfate solution, producing bioconjugates consisting of 80 nM of VEGF or bFGF and either 8, 80 or 800 nM alginate sulfate (calculated per molecular weight of uronic acid, unless specified otherwise). The bioconjugates were allowed to equilibrate at 37° C. for 1 h. Thirty μl of each sample was placed on mica surface for 1 min, then rinsed with DDW, and dried under N$_2$ (g). The surface was scanned by AFM (Veeco Dimension 3100 Scanning Probe Microscope, SPM). As control, a sample of alginate sulfate with the growth factor was used.

Particle size measurement. The scanned surfaces were analyzed as follows: each picture was divided to 4 sections. At each section, approximately 40 particles were analyzed to give their average radius (One way Anova, Fisher test, P<0.01).

Transmission Electron Microscope (TEM) Analysis:

Cryo-TEM—Wet analysis: Alginate sulfate dissolved in DDW was mixed with bFGF, producing bioconjugate with 11 μM bFGF and 5.05 mM alginate sulfate. The bioconjugate was allowed to equilibrate at 37° C. for 1 h. A drop of the bioconjugate solution was deposited on a TEM grid (300- mesh Cu grid) coated with a holey carbon film (Lacey-substrate, made by Ted Pella, Redding, Calif.), which was mounted on a controlled environment apparatus maintained at 40° C. with very high humidity. Excess liquid was blotted and the specimen was vitrified by a rapid plunging into liquid ethane pre-cooled with liquid $N_2$, in a controlled environment vitrification system. The samples were examined at –178° C. using a FEI Tecnai 12 G2 TWIN TEM equipped with a Gatan 626 cold stage, and the images were recorded (Gatan model 794 charge-coupled device camera) at 120 kV in low-dose mode.

TEM—Dry analysis: Alginate sulfate dissolved in DDW was mixed with bFGF, producing bioconjugate with 11 µM bFGF and 5.05 mM alginate sulfate. The bioconjugate was allowed to equilibrate, at 37° C. for 1 h. A drop of the bioconjugate solution was deposited on a TEM grid (300-mesh Cu grid) coated with a holey carbon film (Lacey-substrate, Ted Pella, Redding, Calif.). The sample was allowed to dry over night at room temperature and then analyzed by TEM.

Dynamic Light Scattering (DLS). The bioconjugate was prepared from 20 mM aqueous alginate sulfate and 29.4 mM bFGF. The particle size was determined by DLS (ALV-NIBS/HPPS High Performance Particle Sizer), at a scattering angle of 90° at room temperature. Some of the samples were filtered with 0.2 µm filters before the analysis.

The results were as follows: The AFM analysis provides quantitative, three-dimensional images and surface analysis with spatial resolution of a few µm down to few Angstroms. The AFM probes the sample surface with a sharp tip (cantilever) and forces between the tip and the analyzed surface cause the cantilever to bend or deflect. A detector measures the tip deflection as the sample is scanned under the tip. The measured cantilever deflection allows the computer to generate a map of the analyzed surface topography. The surface topographical data may be greatly enhanced by other AFM modes such as phase or lateral force imaging.

We used the AFM analysis to characterize the physical nature and morphology of bioconjugates of alginate sulfate and its bound ligand, as well as their particle size. As a control, a solution of alginate sulfate without the bound ligand, has been used. The results of AFM scanning for the control alginate sulfate, with no bound ligand, show linear molecules placed on the mica surface (FIG. 34A), while with the bioconjugate sample, for example of alginate sulfate and bFGF, spherical nanoparticles are seen while the linear ones are no longer seen (FIG. 34B—similar to that of 34A). This indicates that the molecular interactions between alginate sulfate and the growth factor drive self-assembly and creation of nanoparticles. The radius of the bioconjugate particles was measured by AFM, using 3-D reconstructed pictures of the particles on the mica surface (FIG. 35). FIG. 36 depicts the results of particle size analysis as a function of different concentrations of alginate sulfate used for creating the bioconjugate (A-8 nM, B-80 nM and C-800 nM), and of bioconjugates created with bFGF (left images) or VEGF (right images) (80 nM). Taken together, bioconjugates from VEGF and alginate sulfate created larger nanoparticles than the bioconjugates of bFGF, on average by a factor of 1.5. There is no apparent effect of the alginate sulfate concentration in use on bioconjugate size, for both VEGF and bFGF. The different particle size can be explained by the different molecular weight of VEGF (45 kDa) and bFGF (17 kDa). Ka (the equilibrium of growth factor binding to alginate sulfate) is on the same order of magnitude (bFGF-9-20×$10^7$, VEGF-2-3× $10^7$) and assumably has no effect on particle size.

The cryo-TEM technique is suitable for identifying local microstructures in complex fluids, with high water content. When used for polymeric aggregates, the size of which is nearly an order of magnitude greater than several nanometers in cross-sectional dimension, cryo-TEM is a good quantitative probe that does not require any model-dependent analysis. Cryo-TEM for wet samples of the bioconjugate bFGF-alginates sulfate revealed the creation of nanoparticles upon conjugation (FIG. 37). No such particles were observed with only alginate sulfate solution. These results agree with the AFM studies on the particulate nature of the bioconjugates. The particles had a diameter of 64.2+9.8 nm. Dry samples of the same nanoparticles in TEM pictures showed a smaller diameter for the dried nanoparticle, 23.4+2.2 nm (FIG. 38) very similar to the value found by AFM, 24.6+2.1 nm (FIGS. 35, 36). AFM was also performed on dry sample. The difference in nanoparticle size between the wet and dry state of the bioconjugates indicates that the nanoparticles contain a significant amount of water. This is in agreement with the capability of crosslinked alginate to form hydrogels (over 90% of water).

DLS is a well-established technique for measuring particle size over the size range from a few nanometers to a few microns. The concept uses the idea that small particles in a suspension move in a random pattern. We measured the particle size of bioconjugates in suspension and found that 35% of them had a mean particle size of 65.88 nm.

The results above show that conjugation between alginate sulfate and its bound ligand results in self-assembly and the creation of nanoparticles; the nanoparticles have average wet size of 65 nm, and at dry state of 23 nm. The factor affecting particle size is the constituting macromolecules forming the bioconjugate. In addition, the nanoparticles have a hydrogel nature, containing high percentage of water.

REFERENCES

Akashi, M., and Sakamoto N., et al. (1996). Synthesis and Anticoagulant Activity of Sulfated Glucoside-Bearing Polymer. Bioconjugate Chemistry 7(4): 393-395.

Amara, A., Lorthioir O., et al. (1999). Stromal Cell-derived Factor-1a Associates with Heparan Sulfates through the First b-Strand of the Chemokine. The Journal of Biological Chemistry 274(34): 23916-23925.

Capila I., and Linhardt R. J. (2002). Heparin-Protein Interactions. Angewandte Chem Int. Ed., 41, 390-412.

Cochran S., Caiping L., Fairweather, J K, Kett, W C, Coombe D R, Ferro, V. (2003). Probing the Interactions of Phosphosulfomannans with Angiogenic Growth Factors by Surface Plasmon Resonance. J. Med. Chem. 46: 4601-4608.

Dodgson, K S and Price, R G (1962). A note on the determination of the ester sulphate content of sulfated polysaccharides. Biochem. J. 84:106-110.

Freeman I., Kedem A., Geresh S., Cohen S. (2004), Abstract Book of the Joint Meeting of the Tissue Engineering Society International and the European Tissue Engineering Society, Lausanne, Switzerland, Oct. 10-13, 2004.

Kamei, K., Wu X., et al. (2001). The Analysis of Heparin-Protein Interactions Using Evanescent Wave Biosensor with Regioselectivity Desulfated Heparins as the ligand. Analytical Biochemistry 295: 203-213.

Polyak, B., Geresh, S., and Marks, R. S., (2004). Synthesis and characterization of a biotin-alginate conjugate and its application in a biosensor construction. Biomacromolecules. March-April; 5(2):389-96.

Rahmoune, H., Rudland, P. S., et al. (1998). Hepatocyte Growth Factor/Scatter Factor Has Distinct Classes of Binding Site in Heparan Sulfate from Mammary Cells. Biochemistry 37(17): 6003-6008.

Shapiro, L., and Cohen, S., (1997) Novel alginate sponges for cell culture and transplantation. Biomaterials, 18: 583-590.

Xiao-feng, W., Ya-xiang, X., et al. (2003). Surface Plasmon Resonance Analysis To Evaluate The Importance of Sulfate Groups in Heparin for the Binding with Human aFGF and bFGF. Journal of Zhejiang University Science 1(4): 86-94.

Zhang, F., Fath, M., et al. (2002). A Highly Stable Covalent Conjugated Heparin Biochip for Heparin-Protein Interaction Studies. Analytical Biochemistry 304: 271-273.

The invention claimed is:

1. A bioconjugate nanoparticle, comprising a sulfated polysaccharide selected from the group consisting of alginate sulfate and hyaluronan sulfate and at least one bioactive polypeptide selected from the group consisting of a positively-charged polypeptide, a heparin-binding polypeptide or both, wherein the bioactive polypeptide non-covalently associates with a sulfate group of the sulfated polysaccharide, thereby allowing sustained release of the bioactive polypeptide from the bioconjugate.

2. The bioconjugate nanoparticle according to claim 1, wherein said at least one bioactive polypeptide is a heparin-binding polypeptide.

3. The bioconjugate nanoparticle according to claim 2, wherein said at least one heparin-binding polypeptide is selected from the group consisting of antithrombin III (AT III), thrombopoietin (TPO), serine protease inhibitor (SLP1), C1 esterase inhibitor (C1 INH), Vaccinia virus complement control protein (VCP), a fibroblast growth factor (FGF), a FGF receptor, vascular endothelial growth factor (VEGF), hepatocyte growth factor (HGF), transforming growth factor β1 (TGF-β1), insulin-like growth factor (IGF), a platelet-derived growth factor (PDGF), epidermal growth factor (EGF), CXC chemokine ligand 4 (CXCL4), stromal cell-derived factor-1 (SDF-1), interleukin-6 (IL-6), interleukin-8 (IL-8), Regulated on Activation, Normal T Expressed and Secreted (RANTES), monocyte chemoattractant protein-1 (MOP-1), macrophage inflammatory peptide-1 (MIP-1), lymphotactin, fractalkine, an annexin, apolipoprotein E (ApoE), immunodeficiency virus type-1 (HIV-1) coat protein gp120, cyclophilin A (CypA), Tat protein, viral coat glycoprotein gC, gB or gD of herpes simplex virus (HSV), an envelope protein of Dengue virus, circumsporozoite (CS) protein of *Plasmodium falciparum*, bacterial surface adhesion protein OpaA, l-selectin, P-selectin, heparin-binding growth-associated molecule (HB-GAM), thrombospondin type I repeat (TSR), and amyloid P (AP).

4. The bioconjugate nanoparticle according to claim 3, wherein said at least one heparin-binding polypeptide is selected from the group consisting of PDGF-BB, PDGF-AA, aFGF, bFGF, VEGF, TGFβ1, IL-6, TPO, SDF-1, HGF, EGF, and IGF.

5. The bioconjugate nanoparticle according to claim 4, wherein said at least one heparin-binding polypeptide is at least one polypeptide exhibiting angiogenic activity.

6. The bioconjugate nanoparticle according to claim 5, wherein said at least one polypeptide exhibiting angiogenic activity is selected from TGF-β1, VEGF, aFGF, bFGF, PDGF-BB, IGF, and a combination thereof.

7. The bioconjugate nanoparticle according to claim 6, wherein said at least one polypeptide is bFGF.

8. The bioconjugate nanoparticle according to claim 6, wherein said at least one polypeptide is VEGF or a combination of VEGF, PDGF-BB and TGF-β1.

9. The bioconjugate nanoparticle according to claim 1, wherein said at least one bioactive polypeptide is a positively-charged polypeptide.

10. The bioconjugate nanoparticle according to claim 9, wherein said positively-charged polypeptide is selected from the group consisting of insulin, glatiramer acetate, antithrombin III, interferon-γ, IGF, somatostatin, erythropoietin, luteinizing hormone-releasing hormone, IL-2 and IL-6.

11. The bioconjugate nanoparticle according to claim 1, wherein the bioconjugate is selected from the group consisting of bFGF-alginate sulfate, aFGF-alginate sulfate, PDGF-BB-alginate sulfate, PDGF-BB-alginate sulfate, VEGF-alginate sulfate, TGFβ1-alginate sulfate, IL-6-alginate sulfate, TPO-alginate sulfate, SDF-1-alginate sulfate, HGF-alginate sulfate, EGF-alginate sulfate, IGF-alginate sulfate, bFGF-hyaluronan sulfate and VEGF-hyaluronan sulfate.

12. A pharmaceutical composition comprising a bioconjugate nanoparticle according to claim 1, and a pharmaceutically acceptable carrier.

13. The pharmaceutical composition according to claim 12, wherein said bioconjugate nanoparticle is provided in a supporting matrix.

14. The pharmaceutical composition according to claim 13, wherein the supporting matrix is a polymer selected from the group consisting of a polysaccharide, a protein, an extracellular matrix component, a synthetic polymer, or and a mixture thereof.

15. The pharmaceutical composition according to claim 14, wherein said supporting matrix polymer is alginate hydrogel or hyaluronan hydrogel.

16. The pharmaceutical composition according to claim 12, comprising a alginate hydrogel/alginate sulfate or hyaluronan hydrogel/sulfated hyaluronan scaffold.

17. The pharmaceutical composition according to claim 12, in the form of hydrogel, beads, microspheres, microbeads, hydrogel microcapsules, sponges, scaffolds, foams, colloidal dispersions, suspensions, liquids, or meshes.

18. The bioconjugate nanoparticle according to claim 1, wherein the sulfated polysaccharide is alginate sulfate.

19. The pharmaceutical composition according to claim 17, comprising a bioconjugate nanoparticle of bFGF-sulfated alginate.

20. The pharmaceutical composition according to claim 17, comprising a bioconjugate nanoparticle of VEGF-sulfated alginate.

21. A method of sustained released administration of at least one bioactive polypeptide capable of non-covalently associating with a sulfate group of a sulfated polysaccharide to a patient in need of treatment with said polypeptide, wherein the method comprises administering to said patient an effective amount of the pharmaceutical composition according to claim 12.

* * * * *